United States Patent
Bjornsson et al.

(10) Patent No.: US 10,246,498 B2
(45) Date of Patent: Apr. 2, 2019

(54) GENETICALLY ENCODED HISTONE REPORTER ALLELE CONSTRUCTS

(71) Applicant: THE JOHNS HOPKINS UNIVERSITY, Baltimore, MD (US)

(72) Inventors: Hans Tomas Bjornsson, Baltimore, MD (US); Harry Dietz, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/315,137

(22) PCT Filed: May 29, 2015

(86) PCT No.: PCT/US2015/033179
§ 371 (c)(1),
(2) Date: Nov. 30, 2016

(87) PCT Pub. No.: WO2015/184258
PCT Pub. Date: Dec. 3, 2015

(65) Prior Publication Data
US 2017/0114108 A1    Apr. 27, 2017

Related U.S. Application Data

(60) Provisional application No. 62/005,582, filed on May 30, 2014.

(51) Int. Cl.
| | |
|---|---|
| C07K 14/47 | (2006.01) |
| A01K 67/027 | (2006.01) |
| G01N 33/542 | (2006.01) |
| G01N 33/58 | (2006.01) |
| A61K 31/165 | (2006.01) |
| A61K 31/167 | (2006.01) |
| G01N 33/50 | (2006.01) |
| G01N 33/68 | (2006.01) |

(52) U.S. Cl.
CPC .......... *C07K 14/47* (2013.01); *A01K 67/0275* (2013.01); *A01K 67/0276* (2013.01); *A61K 31/165* (2013.01); *A61K 31/167* (2013.01); *G01N 33/5008* (2013.01); *G01N 33/542* (2013.01); *G01N 33/582* (2013.01); *G01N 33/6893* (2013.01); *A01K 2217/072* (2013.01); *A01K 2227/105* (2013.01); *A01K 2267/0356* (2013.01); *C07K 2319/09* (2013.01); *C07K 2319/60* (2013.01); *C07K 2319/61* (2013.01); *C07K 2319/90* (2013.01); *C07K 2319/91* (2013.01); *C07K 2319/915* (2013.01); *C07K 2319/95* (2013.01); *G01N 2500/04* (2013.01); *G01N 2500/10* (2013.01); *G01N 2800/50* (2013.01); *G01N 2800/52* (2013.01)

(58) Field of Classification Search
CPC .......................... C07K 14/47; C07K 2319/70
See application file for complete search history.

(56) References Cited

U.S. PATENT DOCUMENTS

| | | | |
|---|---|---|---|
| 7,056,683 B2 * | 6/2006 | Ting | C07K 14/47 435/194 |
| 7,960,144 B2 | 6/2011 | Waldo et al. | |
| 8,372,635 B2 | 2/2013 | Waldo et al. | |
| 2003/0134865 A1 | 7/2003 | Adcock et al. | |
| 2004/0091967 A1 | 5/2004 | Kohler | |
| 2004/0265906 A1 | 12/2004 | Ting | |

FOREIGN PATENT DOCUMENTS

| | | |
|---|---|---|
| EP | 1524262 A1 | 4/2005 |
| WO | 2001067107 A1 | 9/2001 |
| WO | 2002036783 A2 | 5/2002 |
| WO | 2004044168 A2 | 5/2004 |
| WO | 2005059167 A1 | 6/2005 |
| WO | 2007053114 A1 | 5/2007 |
| WO | 2008033992 A2 | 3/2008 |
| WO | 2013148189 A1 | 10/2013 |

OTHER PUBLICATIONS

Chiang et al. 2012; Histone methylation sensing reporter for development of in vitro high throughput screening and in vivo pharmacodynamics imaging. On the web at wmis.org/abstracts/2012/data/papers/P340.html.*
International Search Report and Written Opinion dated Aug. 5, 2015, from related PCT Patent Application No. PCT/US15/033179.
Sato et al., 'Genetically encoded system to track histone modification in vivo' Scientific Reports, vol. 3 Article No. 2436 (internal pp. 1-7) (2013).
Hertel et al., 'Monitoring of post-translational modification dynamics with genetically encoded fluorescent reporters' Biopolymers, vol. 101, No. 2, pp. 180-187 (Epub. Apr. 10, 2013).
Tallini et al., Propagated endothelial Ca2+ waves and arteriolar dilation in vivo: measurements in Cx40BAC GCaMP2 transgenic mice., 2007 Circ Res 101:1300.
Brind'Amour et al., An ultra-low-input native ChIP-seq protocol for genome-wide profiling of rare cell populations., 2015 Nat Commun 21;6:6033.
Gilfillan et al., Limitations and possibilities of low cell number ChIP-seq., 2012 BMC Genomics Nov. 21;13:645.

(Continued)

*Primary Examiner* — Karen Cochrane Carlson
(74) *Attorney, Agent, or Firm* — Casimir Jones, S.C.; Jeffrey W. Childers

(57) ABSTRACT

Non-FRET-based fusion protein reporter molecules are provided that can be used to monitor histone modifications in living cells. Transgenic animals, particularly non-human mammals, whose genomes comprise an expression cassette encoding a non-FRET-based fusion protein reporter, are also provided. Methods of using the fusion reporter molecules for diagnosing histone-modification-associated disorders and to identify candidate pharmaceutical agents that effect histone modification in cells and tissues are also provided.

27 Claims, 34 Drawing Sheets

Specification includes a Sequence Listing.

(56) References Cited

OTHER PUBLICATIONS

Buenrostro et al., ATAC-seq: A Method for Assaying Chromatin Accessibility Genome-Wide., 2015 Curr Protoc Mol Biol 109:21.29.1-9.
Souslova et al., Single fluorescent protein-based Ca2+ sensors with increased dynamic range., 2007 BMC Biotechnol 7:37.
Loeys et al., Mutations in fibrillin-1 cause congenital scleroderma: stiff skin syndrome., 2010 Sci Transl Med 23:23ra20.
Adamcyk et al., GluA3-deficiency in mice is associated with increased social and aggressive behavior and elevated dopamine in striatum., 2012 Behav Brain Res 229:265.
Kesner., An analysis of the dentate gyrus function., 2013 Behav Brain Res 254:1-7.
Morris et al., Selective Lesions of the Dentate Gyrus Produce Disruptions in Place Learning for Adjacent Spatial Locations., 2012 Neurobiol Learn Mem 97:326.
Epp et al., Activation and survival of immature neurons in the dentate gyrus with spatial memory is dependent on time of exposure to spatial learning and age of cells at examination., 2011 Neurobiol Learn Mem.
Langmead et al., Fast gapped-read alignment with Bowtie 2., 2012 Nat Methods 9:357-9.
Zhang et al., Model-based analysis of ChIP-Seq (MACS)., 2008 Genome Biol 9:R137.
Quinlan et al., Bedtools: a flexible suite of utilities for comparing genomic features., 2010 Bioinformatics 26:841-2.
McCarthy et al., Differential expression analysis of multifactor RNA-Seq experiments with respect to biological variation., 2012 Nucleic Acids Res. 40:4288.
Robinson et al., edgeR: a Bioconductor package for differential expression analysis of digital gene expression data., 2010 Bioinformatics 26:139-40.
Hunter et al., InterPro in 2011: new developments in the family and domain prediction database., 2012 Nucleic Acids Res 40: 306-12.
Kerimoglu et al., Histone-Methyltransferase MLL2 (KMT2B) Is Required for Memory Formation in Mice., 2013 J Neurosci 33:3452.
Bogershausen et al., Skirting the pitfalls: a clear-cut nomenclature for H3K4 methyltransferases., 2013 Clin Genet 83:212.
Guan et al., Integration of long-term-memory-related synaptic plasticity involves bidirectional regulation of gene expression and chromatin structure., 2002 Cell 111:483.
Gupta et al., Histone methylation regulates memory formation., 2010 J Neurosci 30:3589.
Cohen-Armon et al., Long-term memory requires polyADP-ribosylation., 2004 Science 304:1820.
Rao et al., Efficacy of doublecortin as a marker to analyse the absolute number and dendritic growth of newly generated neurons in the adult dentate gyrus., 2004 Eur J of Neurosci 19:234-246.
Lea et al., Induction of reporter gene expression by inhibitors of histone deacetylase., Anticancer Research 1998:2717-2721.
Razin et al., DNA methylation and gene function., 1980 Science 210:604.
Zuckerkandl., A possible role of "inert" heterochromatin in cell differentiation. Action of and competition for "locking" molecules., 1974 Biochimie 56:937.
Liu et al., Metabolic modulation of chromatin: implications for DNA repair and genomic integrity., 2013 Front Genet 4:182.
Wolffe et al., Epigenetics: Regulation Through Repression., 1999 Science 286:481-86.
Zentner et al., Regulation of nucleosome dynamics by histone modifications., 2013 Nat Struct Mol Bio 20:259-86.
Baylin et al., A decade of exploring the cancer epigenome—biological and translational implications., 2011 Nat Rev Cancer 11:726.
Feinberg., Phenotypic plasticity and the epigenetics of human disease., 2007 Nature 447:433-40.
Barlow., Genomic Imprinting: A Mammalian Epigenetic Discovery Model., 2011 Annu Rev Genet 45:379-403.
Phiel et al., Histone deacetylase is a direct target of valproic acid, a potent anticonvulsant, mood stabilizer, and teratogen., 2011 J Biol Chem 276:36734.
Meeran et al., Epigenetic targets of bioactive dietary components for cancer prevention and therapy., 2010 Clin Epigenetics 1:101.
Berdasco et al., Genetic syndromes caused by mutations in epigenetic genes., 2013 Hum Genet 132:359.
Wolffe., Nucleosome positioning and modification: chromatin structures that potentiate transcription., 1994 Trends Biochem Sci 19:240-44.
Jaenisch et al., Epigenetic regulation of gene expression: how the genome integrates intrinsic and environmental signals., 2003 Nat Genet 33(suppl.):245.
Lu et al., Metabolic regulation of epigenetics., 2012 Cell Metab 16:9-77.
Ficz et at., Polycomb group protein complexes exchange rapidly in living Drosophila., 2005 Development 132:3963.
Mito et al., Histone Replacement Marks the Boundaries of cis-Regulatory Domains., 2007 Science 315:1408.
Petrij et al., Rubinstein-Taybi syndrome caused by mutations in the transcriptional co-activator CBP., 1995 Nature 376:348.
Roelfsema et al., Genetic Heterogeneity in Rubinstein-Taybi Syndrome: Mutations in Both the CBP and EP300 Genes Cause Disease., 2005 Am J Hum Genet 76:572.
Lederer et al., Deletion of KDM6A, a Histone Demethylase Interacting with MLL2, in Three Patients with Kabuki Syndrome., 2012 Am J Hum Genet 90:119.
Ng et al., Exome sequencing identifies MLL2 mutations as a cause of Kabuki syndrome., 2010 Nat Genet 42:790.
Jones et al., De Novo Mutations in MLL Cause Wiedemann-Steiner Syndrome., 2012 Am J Hum Genet 91:358.
Gibson et al., Mutations in EZH2 Cause Weaver Syndrome., 2012 Am J Hum Genet 90:110.
Tatton-Brown et al., Germline mutations in the oncogene EZH2 cause Weaver syndrome and increased human height., 2011 Oncotarget 2:1127.
Kurotaki et al., Haploinsufficiency of NSD1 causes Sotos syndrome.., 2002 Nat Genet 30:365.
Williams et al., Haploinsufficiency of HDAC4 Causes Brachydactyly Mental Retardation Syndrome, with Brachydactyly Type E, Developmental Delays, and Behavioral Problems., 2010 Am J Hum Genet 87:219.
Kleefstra et al., Loss-of-Function Mutations in Euchromatin Histone Methyl Transferase 1 (EHMT1) Cause the 9q34 Subtelomeric Deletion Syndrome., 2006 AM J Hum Genet 79:370.
Jensen et al., Mutations in the JARID1C Gene, Which Is Involved in Transcriptional Regulation and Chromatin Remodeling, Cause X-Linked Mental Retardation., 2005 Am J Hum Genet 76:227.
Hadjantonakis et al., Dynamic in vivo imaging and cell tracking using a histone fluorescent protein fusion in mice., BMC Biotechnology 2004:33.
Lin et al., A genetically encoded fluorescent reporter of histone phosphorylation in living cells., 2004 Angew Chem Int Ed Engl 24; 43(22):2940.
Lin et al., Genetically encoded fluorescent reporters of histone methylation in living cells., 2004 J Am Chem Soc 126(19):5982.
Baird et al., Circular permutation and receptor insertion within green fluorescent proteins.,1999 Proc Natl Acad Sci USA 96(20):11241.
Zeng et al., Bromodomain: an acetyl-lysine binding domain., FEBS lett 513(1):124-8 2002.
Horn et al., The Bromodomain: A Regulator of ATP-Dependent Chromatin Remodeling?, Front Biosci 6:D1019-23(2001).
Winston et al., The bromodomain: a chromatin-targeting module?, Nat Struct Biol 6(7):601-4(1999).
Akhtar et al., Chromodomains are protein—RNA interaction modules., Nature 407(6802):405-9(2000).
Fu et al., 14-3-3 proteins: structure, function, and regulation., 2000 Annu Rev Pharmacol Toxicol 40, 617.
Brickman et al., Hippocampal subregions differentially associate with standardized memory tests., 2011 Hippocampus 21:923.
Yaffe et al., Phosphoserine/threonine-binding domains., 2001 Curr Opin Cell Biol 13:131:138.

(56) References Cited

OTHER PUBLICATIONS

Ward et al., Spectral Perturbations of the Aequorea Green-Fluorescent Protein., 1982 Photochem Photobiol 35:803:808.
Levine et al., Isolation and Characterization of a Photoprotein, "Phialidin", and a Spectrally Unique Green-Fluorescent Protein From the Bioluminescent Jellyfish Phialidium Gregarium*., 1982 Comp Biochem Physiol 72B:77-85.
Huston et al., Protein engineering of antibody binding sites: recovery of specific activity in an anti-digoxin single-chain Fv analogue produced in *Escherichia coli*., 1988 PNAS 85:5879.
Whitlow et al., An improved linker for single-chain Fv with reduced aggregation and enhanced proteolytic stability., 1993 Protein Engineering 6:989-995.
Newton et al., Angiogenin Single-Chain Immunofusions: Influence of Peptide Linkers and Spacers between Fusion Protein Domains., 1996 Biochemistry 35:545-553.
Kunkel., Rapid and efficient site-specific mutagenesis without phenotypic selection., 1985 Proc Nat Acad Sci USA 82:488-492.
Hohenstein et al., High-efficiency Rosa26 knock-in vector construction for Cre-regulated overexpression and RNAi., 2008 Pathogenetics 3; 1(1):3.
Munshi et al., Vorinostat, a histone deacetylase inhibitor, enhances the response of human tumor cells to ionizing radiation through prolongation of gamma-H2AX foci., 2006 Mol Cancer Ther 5:1967-74.
Huang et al., Histone Deacetylase Inhibitors Stimulate Histone H3 Lysine 4 Methylation in Part Via Transcriptional Repression of Histone H3 Lysine 4 Demethylases., 2011 Mol Pharmacol 79:197.
Vermeulen et al., Selective Anchoring of TFIID to Nucleosomes by Trimethylation of Histone H3 Lysine 4., 2007 Cell 131:58-69.
Van Ingen et al., Structural Insight into the Recognition of the H3K4me3 Mark by the TFIID Subunit TAF3., 2008 Structure 16:1245-56.
Chong et al., Modifiers of epigenetic reprogramming show paternal effects in the mouse., 2007 Nat Genet 39:614.

\* cited by examiner

FIG. 5A

H4ac indicator quantifies the activity of acetylation of H4

Wild-type H4ac indicator:

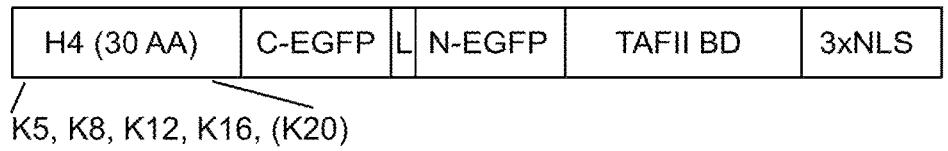

K5, K8, K12, K16, (K20)

Mutant H4ac indicator (all potentially acetylated lysines (K) changed to arginines):

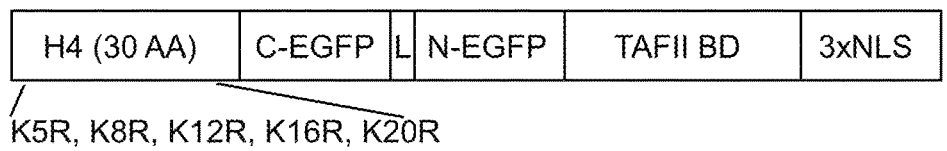

K5R, K8R, K12R, K16R, K20R

TAFII BD = TAFII bromodomain, NLS = Nuclear Localization Signal;
TAFII bromodomain only binds to acetylated H4 (K5, K8, K12, K16).

FIG. 5B

H3K4me3 indicator quantifies activity of H3K4me3:

Wild-type H3K4me3 indicator:

K4

Mutant H3K4me3 indicators carry either H3K4Q or reader domain mutation:

K4Q          D890A/W891A
                                 or
                               M882A

TAF3 PHD = TAF3 PHD domain, NLS = Nuclear Localization Signal;
TAF3 PHD domain only binds to trimethylated H3K4me3.

FIG. 7A

*Exact integration site:*
CTGTGTGGAACCGCATCATTGAGCCTGTGGCTGCCATGAGAAAAGAAGCC
GACATGCTGAGACTCTTCCCCGAGTACCTGAAAGGCGAAGAACTCTTTGG
GCTGACAGTGCATGCAGTGCTTCGCATAGCTGAATCGGTAAGCAAGCGGC
AAGGAGCTGGGGCCAAGGTGGGAATACTTACTGTATGGCGTGCGGGTGT
GTGTGACCGTGGGTACACTTAAAACACCGGTTTTGGATCTGCACTGTCCC
GGATGTCCTCTGGTGCTCAAAGACCCTTTTGGGTTTGCCCTTTGGTAAGA
GCGCCGGGATCTACTTGTCTGGAGGCCAGGGAGTCCTCAGCCGAGGCTT
GCCGCCCCTGACTGCACTGCACTGAGTAGT (SEQ ID NO: 7)

FIG. 7B

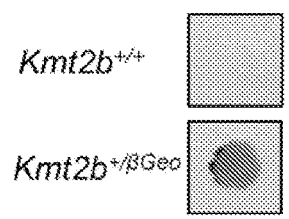

FIG. 18G
FIG. 18H
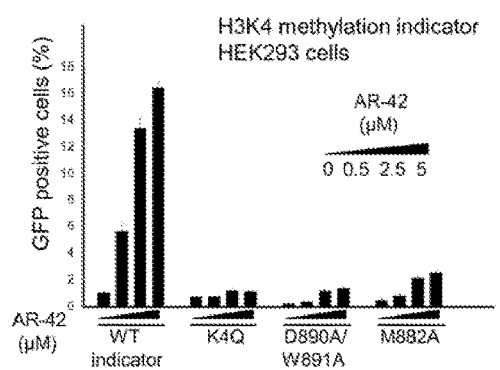
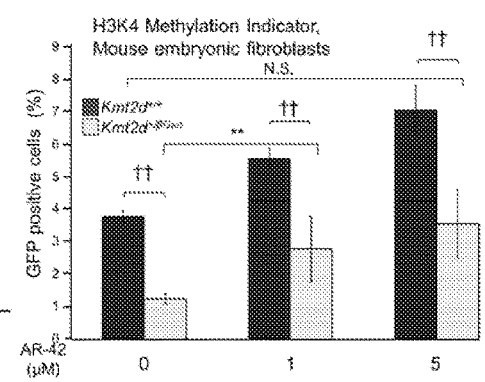
FIG. 18I
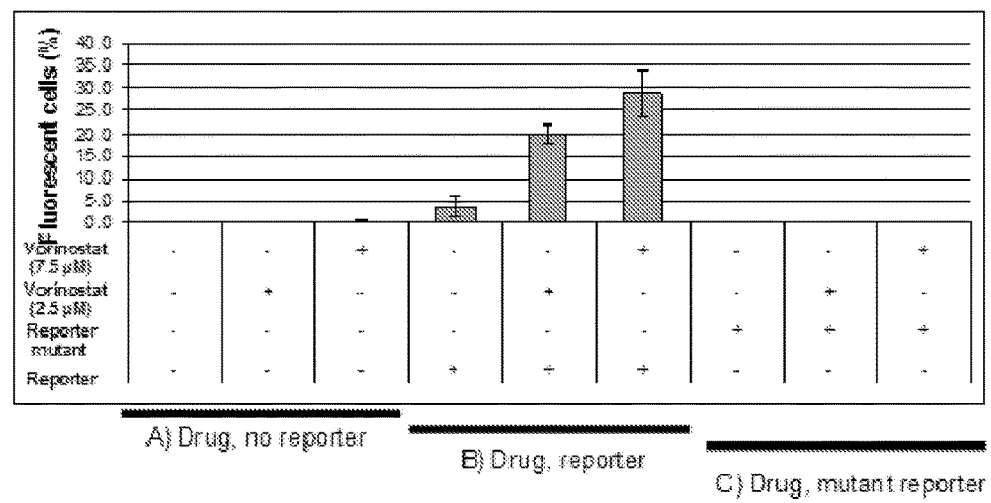

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
caaatggcga ttaccgttga                                              20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
tgcccagtca tagccgaata                                              20

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
caaatgttgc ttgtctggtg                                              20

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
gtcagtcgag tgcacagttt                                              20
```

```
<210> SEQ ID NO 5
<211> LENGTH: 21
<212> TYPE: DNA
<213> ORGANISM: Artificial Sequence
<220> FEATURE:
<223> OTHER INFORMATION: PCR primer

<400> SEQUENCE: 5
ctgcgcgcaa gtcaacgggt g                                                21

<210> SEQ ID NO 6
<211> LENGTH: 21
<212> TYPE: DNA
<213> ORGANISM: Artificial Sequence
<220> FEATURE:
<223> OTHER INFORMATION: PCR primer

<400> SEQUENCE: 6
atgccgttct tctgcttgtc g                                                21

<210> SEQ ID NO 7
<211> LENGTH: 379
<212> TYPE: DNA
<213> ORGANISM: Artificial Sequence
<220> FEATURE:
<223> OTHER INFORMATION: Mouse Kmt2d exon 50/intron 50/ beta-Geo
      cassette

<400> SEQUENCE: 7
ctgtgtggaa ccgcatcatt gagcctgtgg ctgccatgag aaaagaagcc gacatgctga       60
gactcttccc cgagtacctg aaaggcgaag aactctttgg gctgacagtg catgcagtgc      120
ttcgcatagc tgaatcggta agcaagcggc aaggagctgg ggccaaggtg ggaatactta      180
ctgtatggcg tgcgggtgtg tgtgaccgtg ggtacactta aaacaccggg ttttggatct      240
gcactgtccc ggatgtcctc tggtgctcaa agacccttt  gggtttgccc tttggtaaga      300
gcgccgggat ctacttgtct ggaggccagg gagtcctcag ccgaggcttg ccgcccctga      360
ctgcactgca ctgagtagt                                                  379
```

GENETICALLY ENCODED HISTONE REPORTER ALLELE CONSTRUCTS

CROSS-REFERENCE TO RELATED APPLICATIONS

This application is a 35 U.S.C. § 371 National Stage Entry of International Application No. PCT/US2015/033179 having an international filing date of May 29, 2015, which claims the benefit of U.S. Provisional Application No. 62/005,582, filed May 30, 2014, the contents of which are incorporated herein by reference in their entirety.

INCORPORATION-BY-REFERENCE OF MATERIAL SUBMITTED ELECTRONICALLY

This application contains a sequence listing. It has been submitted electronically via EFS-Web as an ASCII text file entitled "111232-00409_ST25.txt". The sequence listing is 2,016 bytes in size, and was created on May 22, 2015. It is hereby incorporated herein by reference in its entirety.

BACKGROUND

Epigenetics refers to heritable changes in gene expression in the absence of alterations in the DNA sequence (Russo et al., eds. (1996) *Epigenetic Mechanisms of Gene Regulation*. Woodbury, N.Y.: Cold Spring Harb. Lab. Press). Epigenetic modifications are thought to be one of the critical mechanisms that mediate gene-environment interactions and play a major role in tissue- and cell-type-specific differences in gene expression (Razin & Riggs (1980) *Science* 210:604-10; Zuckerkandl (1974) *Biochimie* 56:937-54) and many other cellular processes (Liu et al. (2013) *Front. Genet.* 4:182; Wolffe & Matzke (1999) *Science* 286:481-86; Zentner & Henikoff (2013) *Nat. Struct. Mol. Biol.* 20:259-66). The role of epigenetics in disease is well established in the field of cancer (Baylin & Jones (2011) *Nat. Rev. Cancer* 11:726-34; Feinberg (2007) *Nature* 447:433-40) and imprinting disorders (Barlow (2011). *Annu. Rev. Genet.* 45:379-403).

There are many FDA-approved medications, some with longstanding clinical use, that influence epigenetic modifications in addition to their originally established functions. An example is the anti-epileptic agent valproic acid, which was recently shown to be a potent histone deacetylase inhibitor (HDACi; Phiel et al. (2001) *J. Biol. Chem.* 276: 36734-41). Several widely-used supplements or dietary substances, such as folic acid, genestein, and curcumin, are known to influence epigenetic modifications (Meeran et al. (2010) *Clin. Epigenetics.* 1:101-116).

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Nonlimiting descriptions of certain of these techniques are found in the following 10 publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning. A Laboratory Manual, 3rd ed., Cold Spring Harbor Laboratory Press, Cold Spring Harbor, 2001; Harlow, E. and 15 Lane, D., Antibodies-A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 20 2005, Katzung, B. (ed.) Basic and Clinical Pharmacology, McGraw-Hill/Appleton & Lange 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online 25 Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: www.ncbi.nlm.nih.gov/omim/ and in Online Mendelian Inheritance in Animals (OMIA), a database of genes, inherited disorders 30 and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

The presently disclosed subject matter relates to a genetically encoded histone reporter allele system that can be used to facilitate the development of therapeutic treatments with epigenetically active agents. In particular, the genetically encoded histone reporter allele system of the presently disclosed subject matter can be utilized for high throughput screening in in vitro cellular systems and can be introduced into subjects (e.g., laboratory mice) for in vivo therapeutic monitoring.

In one aspect of the presently disclosed subject matter, fusion protein reporter constructs are provided. The constructs encode fusion proteins that include a core comprising a histone-modification-specific binding domain, a histone polypeptide substrate, and a flexible linker region flanked on one side by a region encoding a C-terminal portion of a circularly permutated fluorescent protein and on the other side by a region encoding the N-terminal portion of the circularly permutated fluorescent protein. In some embodiments, the histone polypeptide substrate is selected from the group consisting of H3 or H4. In some embodiments, the histone polypeptide is selected from the group consisting of the N-terminus of H3 and the N-terminus of H4. In some embodiments, the histone modification is selected from the group consisting of acetylation, methylation, and phosphorylation. In some embodiments, the histone modification-specific binding domain is selected from the group consisting of a TBP associated factor II (TAFII) bromodomain and a TBP associated factor III (TAFIII) homeodomain. In other embodiments, the histone polypeptide is a polypeptide substrate for the histone-modification-specific binding domain. In certain embodiments, the fusion protein reporter also includes a targeting polypeptide, associated with the fusion protein. In some embodiments, the targeting polypeptide comprises at least one a nuclear localization sequence (NLS), particularly wherein the targeting polypeptide comprises a repeated NLS. In some embodiments, the circularly permutated fluorescent protein comprises a circularly permutated green fluorescent protein (GFP).

In some aspects, the presently disclosed subject matter provides expression vectors comprising an expression cassette encoding a fusion protein reporter described herein. Some aspects of the presently disclosed subject matter also provide host cells transformed or transfected with the expression vector. Other aspects of the presently disclosed subject matter provide a transgenic animal, particularly a non-human mammal, whose genome comprises an expression cassette encoding a fusion protein reporter described herein.

In one aspect of the presently disclosed subject matter, a method for producing a cell specific screening assay for test agents, comprises providing a transgenic animal whose genome comprises an expression cassette encoding a fusion protein reporter described herein, crossing the transgenic animal with a compatible animal, wherein the compatible animal is an animal model of a disease, thereby producing a hybrid, isolating a disease relevant cell type from the hybrid, and utilizing the isolated disease relevant cell types in a high throughput screening assay for test agents.

In another aspect of the presently disclosed subject matter, methods of determining the level of histone modification are provided. The methods include contacting a biological sample with a fusion protein reporter described herein, and monitoring the level of fluorescence in the biological sample as a measure of the level of histone modification in the biological sample. In some embodiments, the biological sample is a cell. In some embodiments, the cell is undergoing cell division. The methods also include incorporating an expression cassette encoding a fusion protein reporter described herein into the genome of an animal, particularly a non-human mammal, and monitoring the level of fluorescence in living cells of the animal as a measure of the level of histone modification in the living cells.

In another aspect of the presently disclosed subject matter, methods of diagnosing a histone-modification disorder in a subject are provided. The methods include contacting a biological sample from a subject with a fusion protein reporter described herein, monitoring the level of fluorescence in the biological sample, comparing the level of fluorescence in the sample to a control level of fluorescence as a determination of a histone modification disorder in the subject. In some embodiments, the biological sample is selected from the group consisting of tissue and cells, particularly living cells.

In yet another aspect of the presently disclosed subject matter, methods of monitoring the onset, progression, or regression of a histone-modification disorder in a subject are provided. The methods include contacting a first biological sample from a subject with a fusion protein reporter described herein, determining the level of fluorescence in the first biological sample, contacting a subsequent second biological sample from the subject with a fusion protein reporter of any of the foregoing embodiments, determining the level of fluorescence in the second biological sample, and comparing the level of fluorescence in the first biological sample to the level of fluorescence in the second biological sample as a measure of the onset, regression or progression of a histone modification disorder in the subject. In some embodiments, the biological sample is selected from the group consisting of tissue and cells, particularly living cells.

In some aspects, the method of monitoring the onset, progression or regression of a histone-modification disorder in a subject also includes administering after the first biological sample is obtained from the subject and before the second biological sample is obtained from the subject a candidate pharmacological agent to the subject, wherein the measure of the onset regression or progression of a histone modification disorder in the subject is an indication of the effect of the candidate pharmacological agent on histone modification in the subject. In some embodiments, the biological sample is selected from the group consisting of tissue and cells, particularly living cells.

In another aspect of the presently disclosed subject matter, methods for evaluating the effect of a candidate pharmacological agent on histone modifications in a biological sample are provided. The methods comprise contacting a biological sample with a fusion protein reporter fusion protein reporter described herein, determining a first level of fluorescence in the biological sample, contacting the biological sample with a candidate pharmacological agent, determining a second level of fluorescence in the biological sample, and comparing the first level of fluorescence in the cell with the second level of fluorescence in the cell, wherein a relative increase or relative decrease in fluorescence indicates an effect of the candidate pharmacological agent on histone modification in the biological sample. In some embodiments, the biological sample is selected from the group consisting of tissue and cells, particularly living cells. In some embodiments, the biological sample is a cell. In some embodiments, the cell is undergoing cell division. In some embodiments, the cell is a living cell.

In yet another aspect of the presently disclosed subject matter, a kit for diagnosing and/or monitoring treatment efficacy of a histone-modification disorder is provided, comprising a container containing a fusion protein reporter fusion protein reporter described herein and instructions for the use of the fusion protein reporter in the diagnosis and/or monitoring treatment efficacy of a histone-modification disorder.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
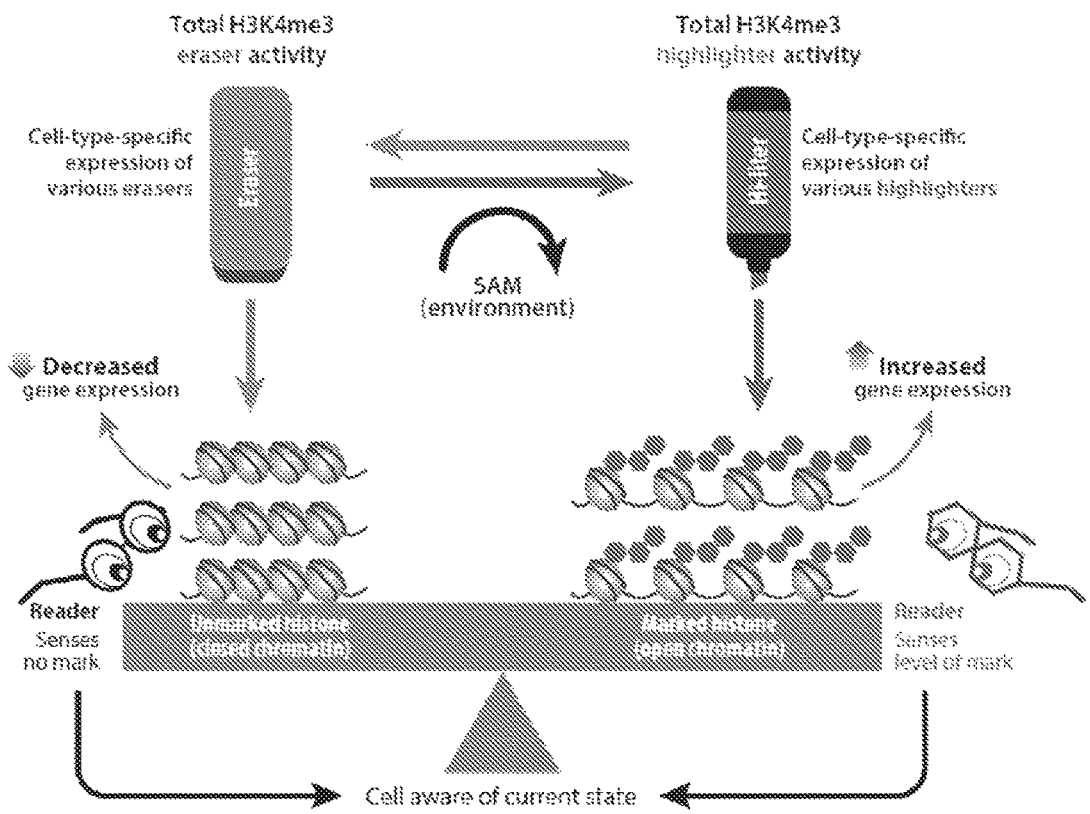
Figure 2:
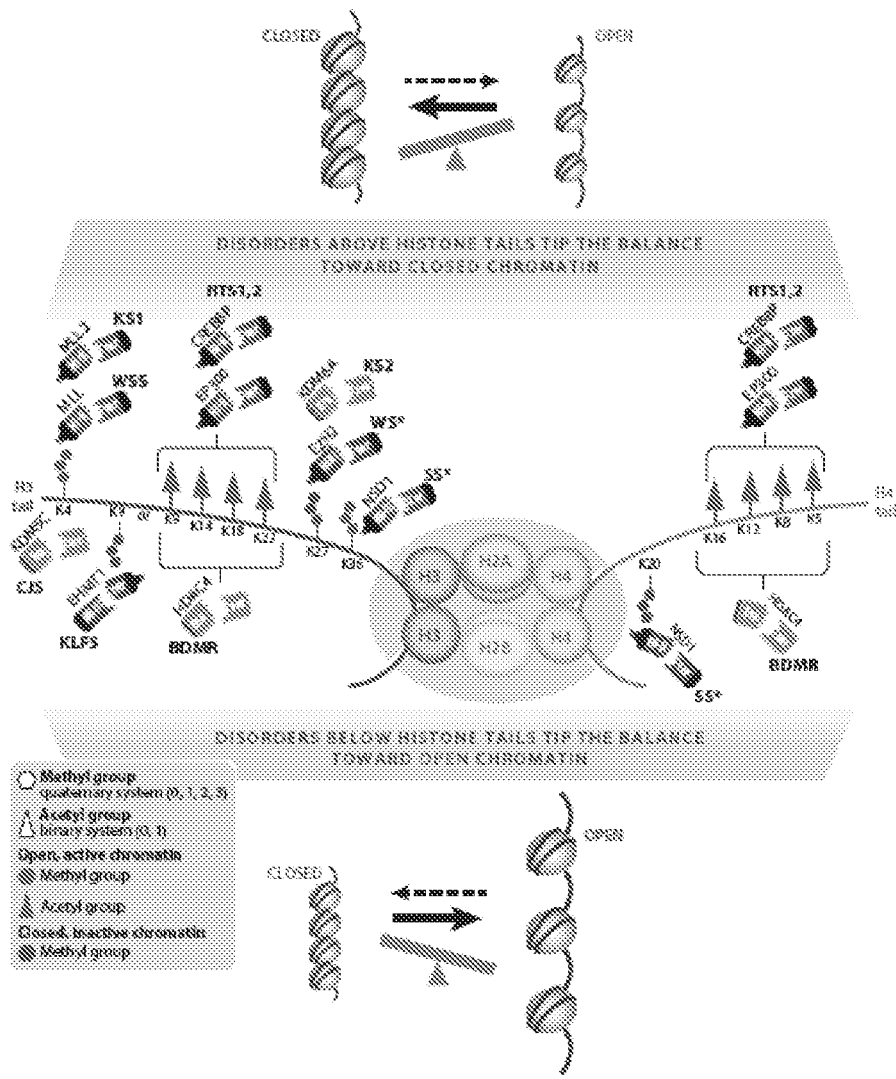
Figure 3:
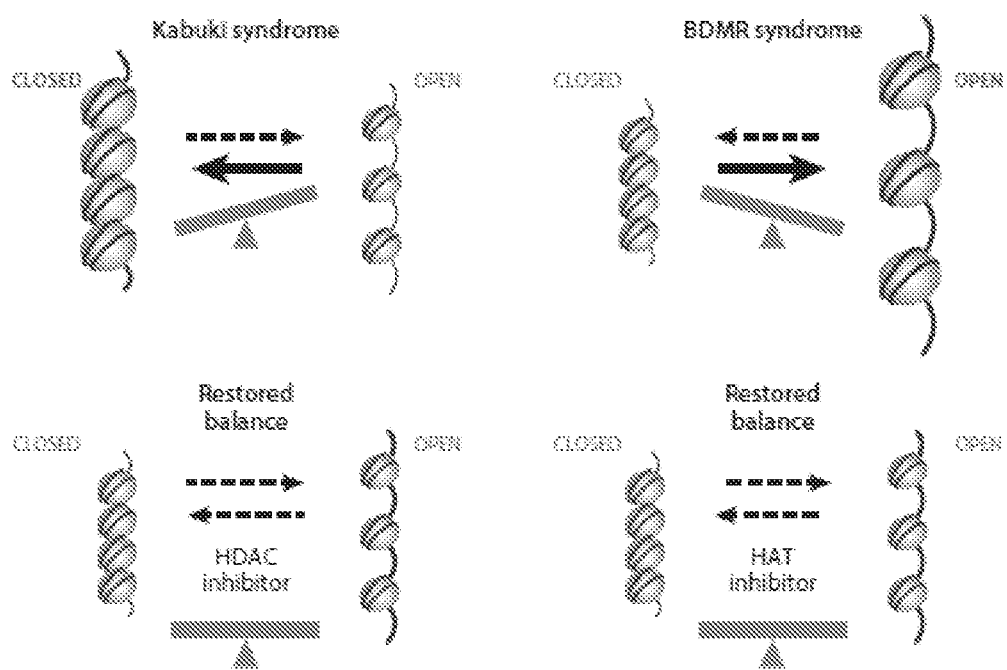
Figure 4:
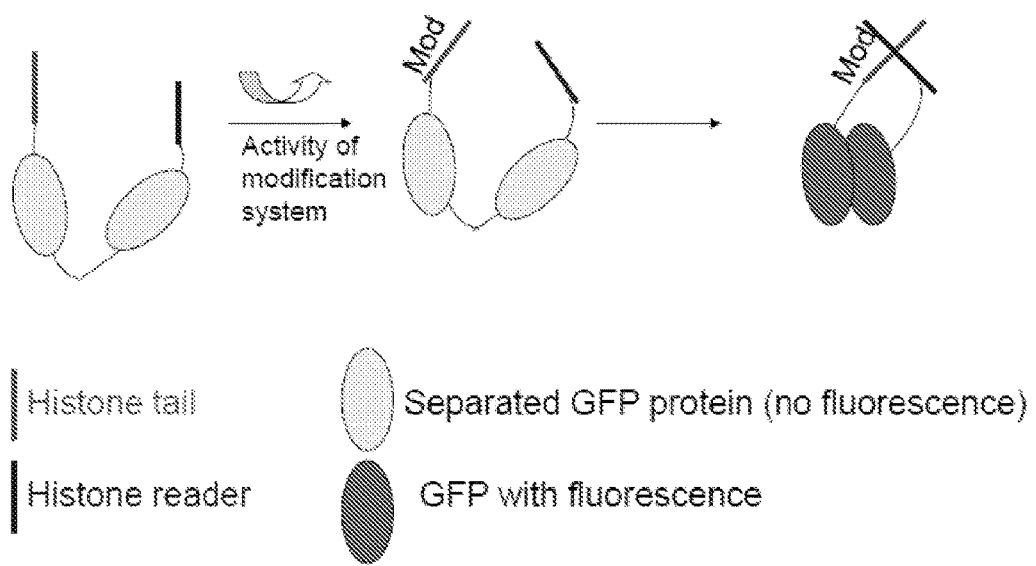
Figure 6A:
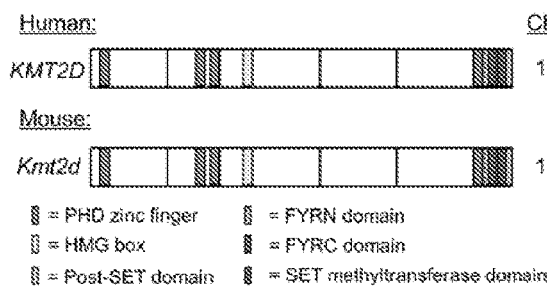
Figure 6B:
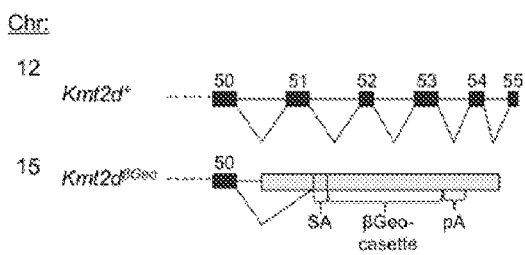
Figure 6C:
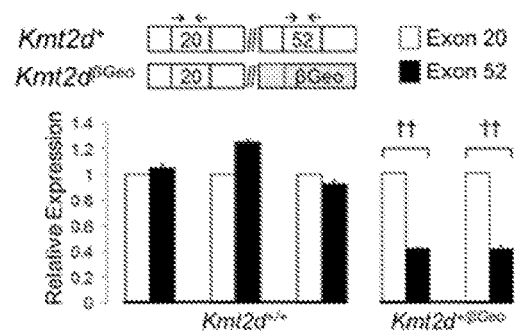
Figure 6D:
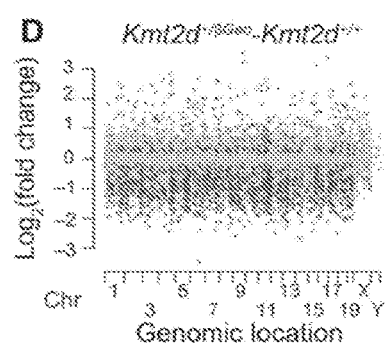
Figure 6E:
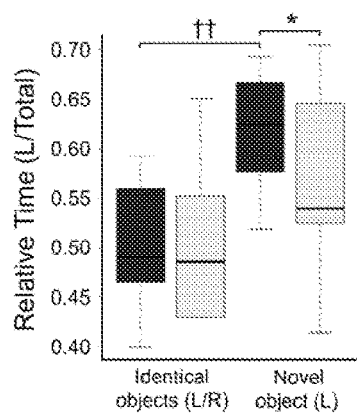
Figure 6F:
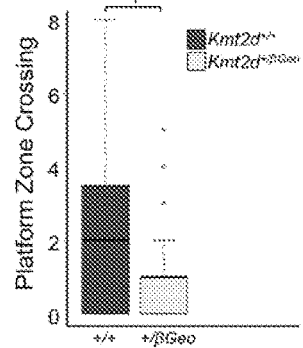
Figure 8A:
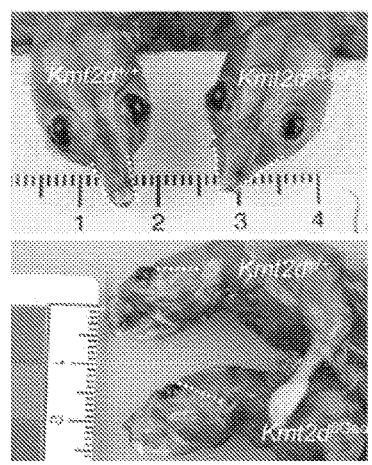
Figure 8B:
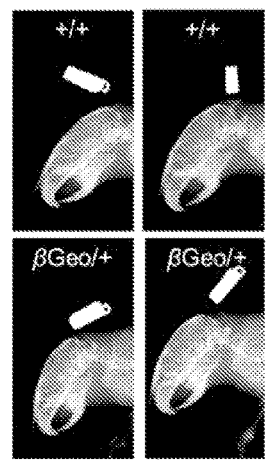
Figure 8C:
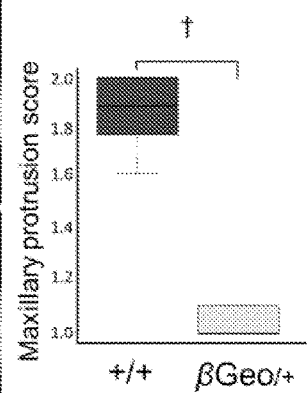
Figure 9:
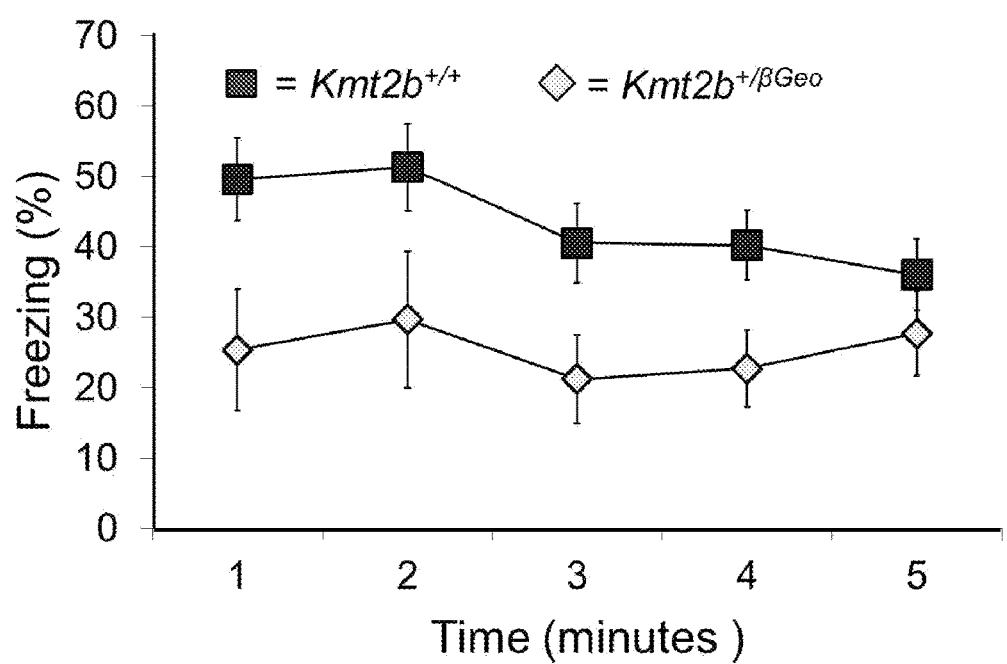
Figure 10:
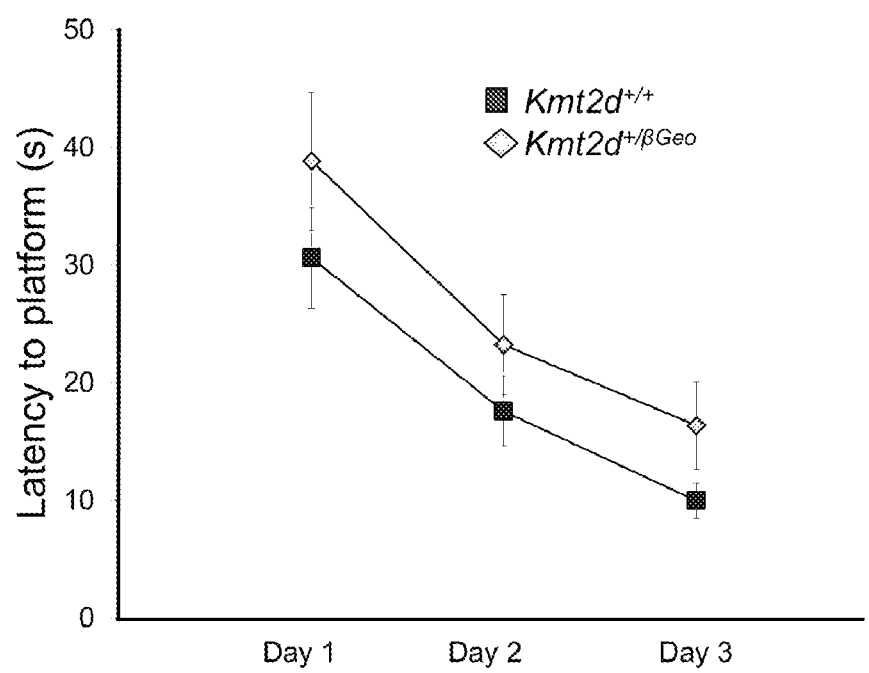
Figure 11A:
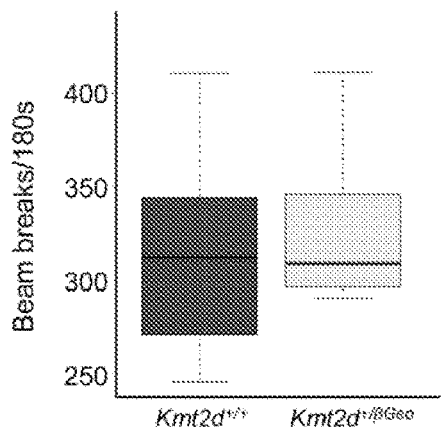
Figure 11B:
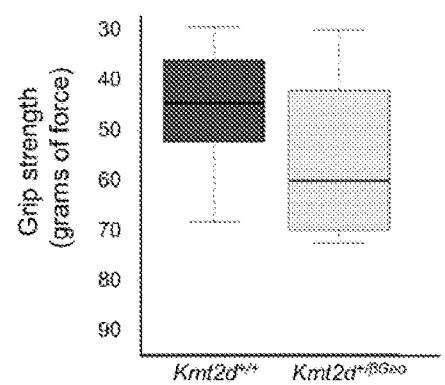
Figure 11A:
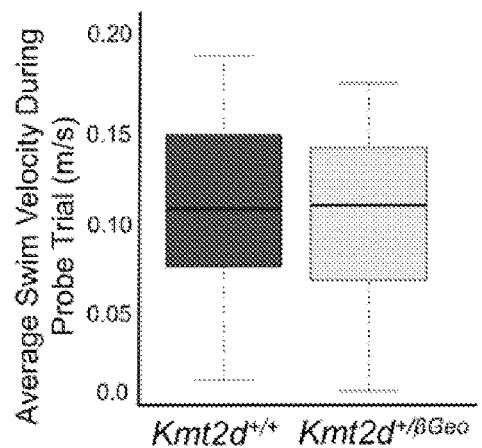
Figure 12A:
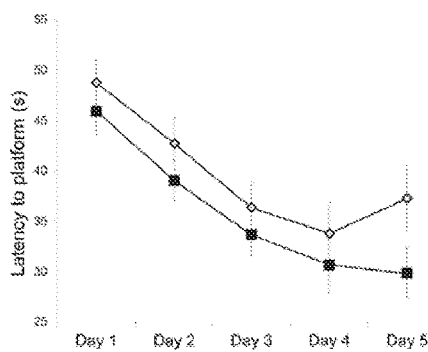
Figure 12B:
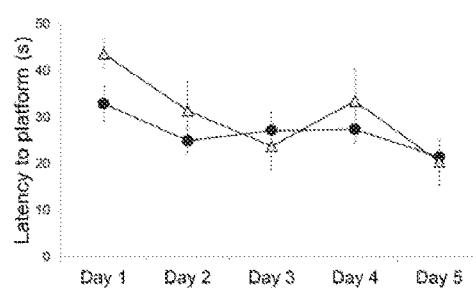
Figure 12C:
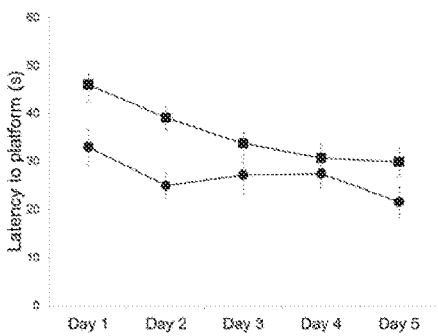
Figure 12D:
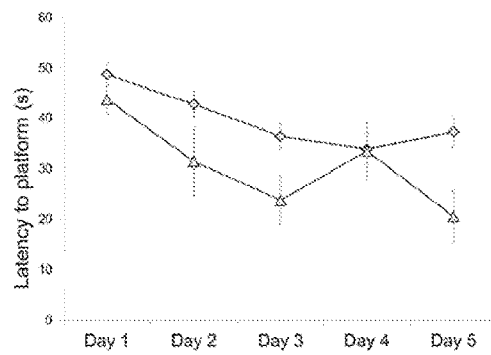
Figure 13A:
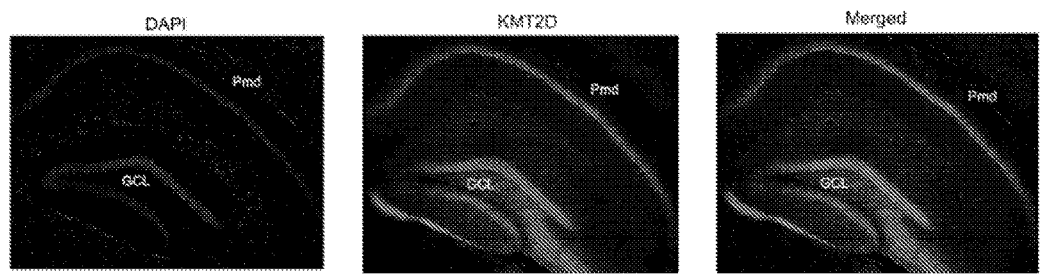
Figure 13B:
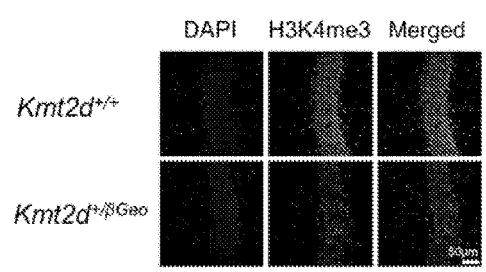
Figure 13C:
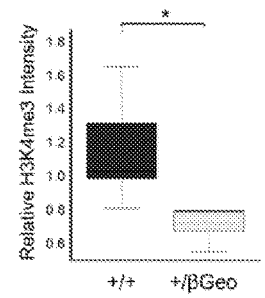
Figure 13D:
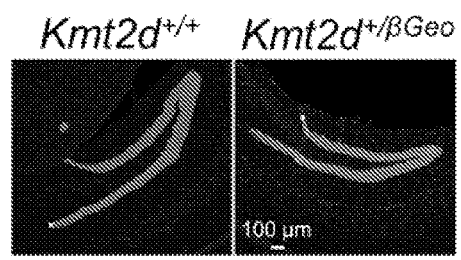
Figure 13E:
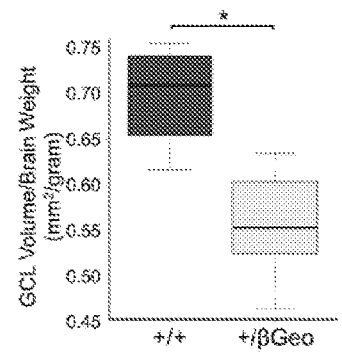
Figure 13F:
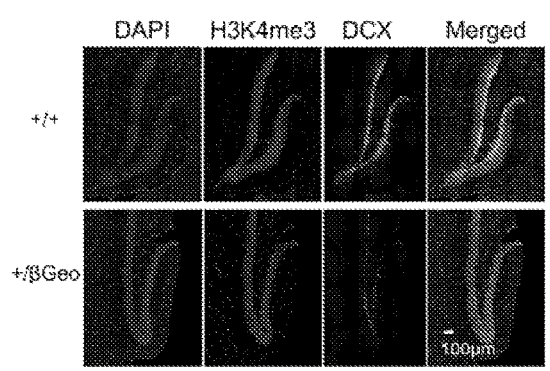
Figure 13G:
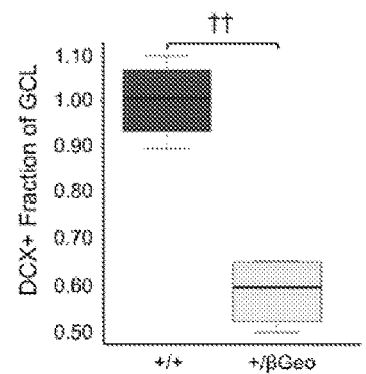
Figure 14:
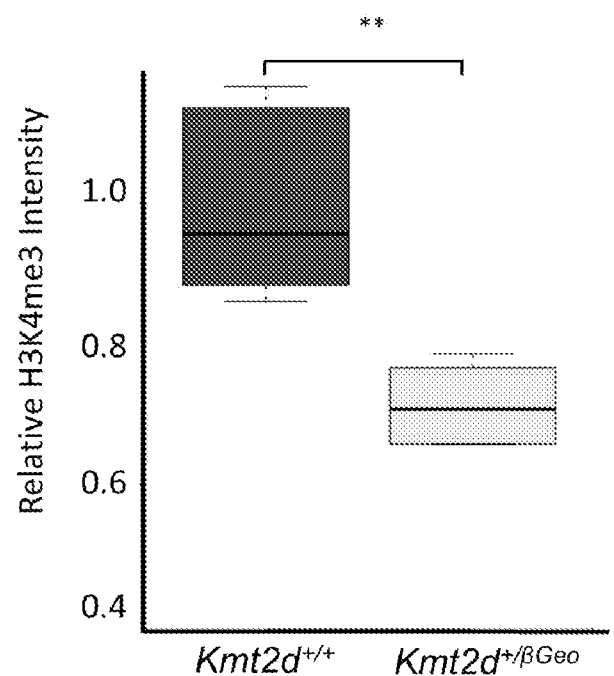
Figure 15A:
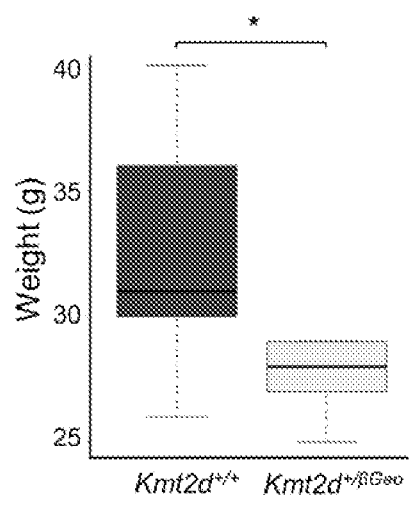
Figure 15B:
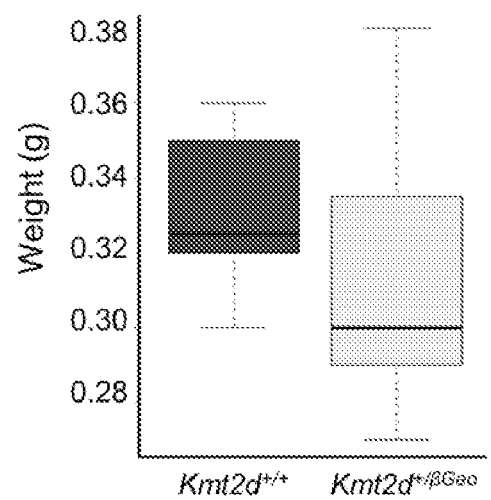
Figure 16:
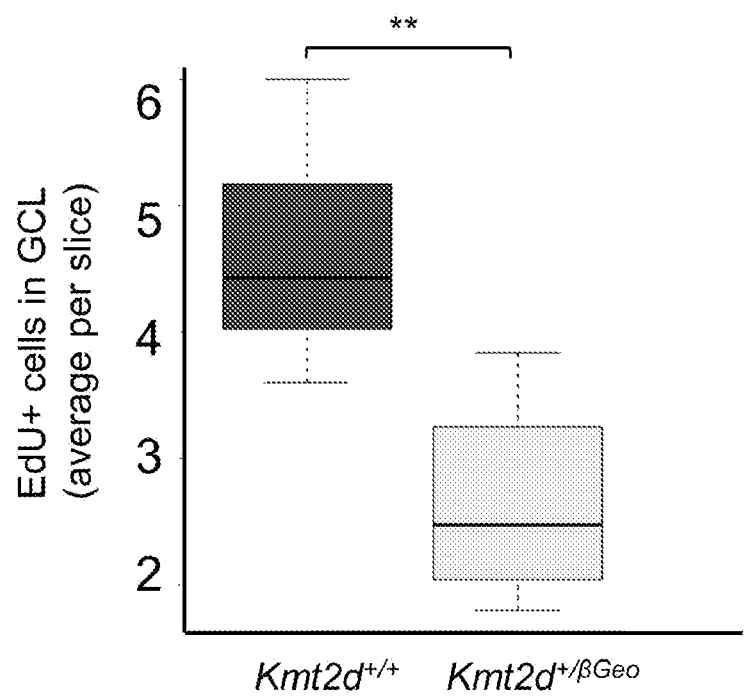
Figure 17:
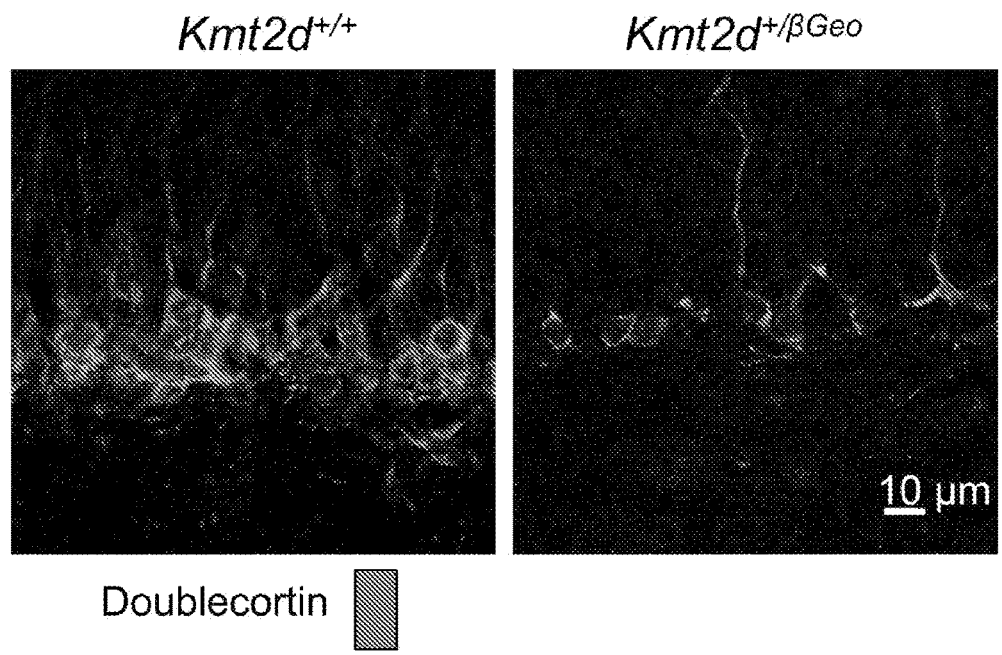
Figure 18A:
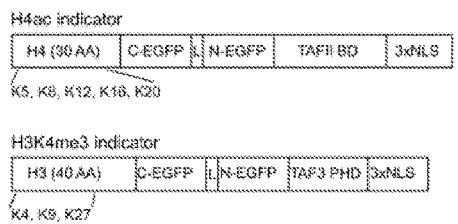
Figure 18B:
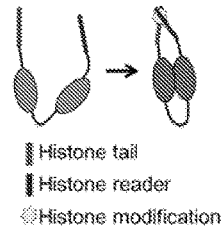
Figure 18C:
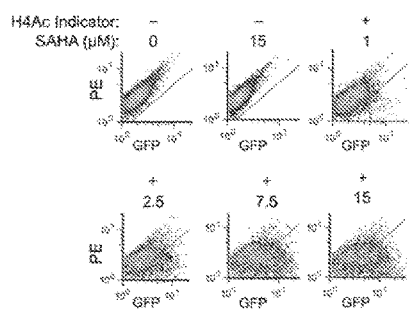
Figure 18D:
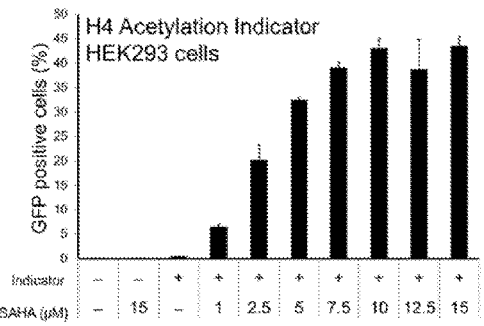
Figure 18E:
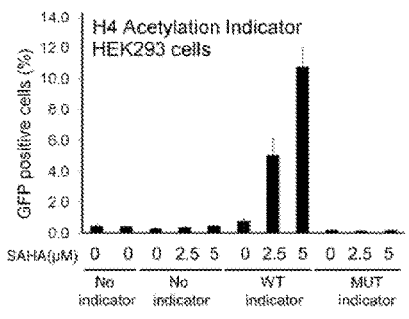
Figure 18F:
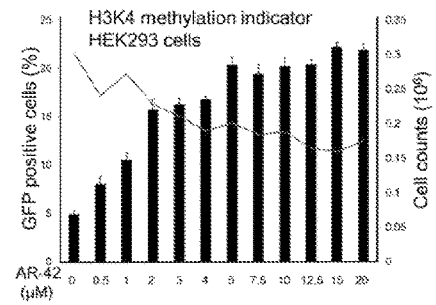
Figure 19A:
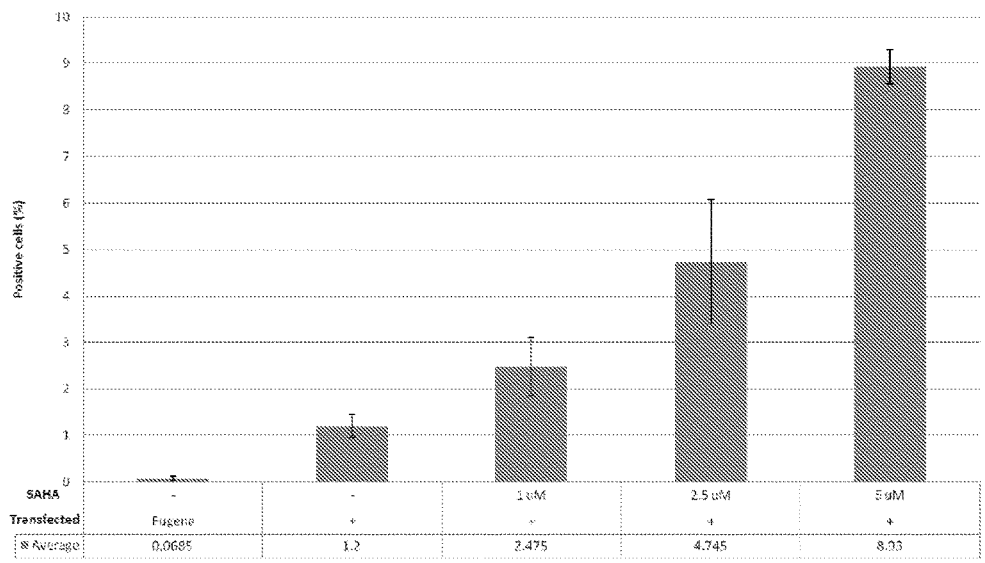
Figure 19B:
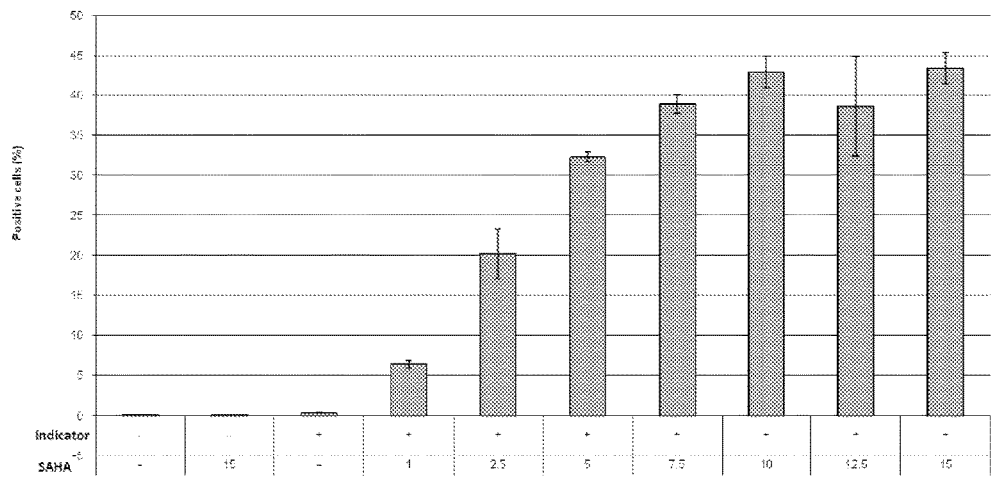
Figure 20:
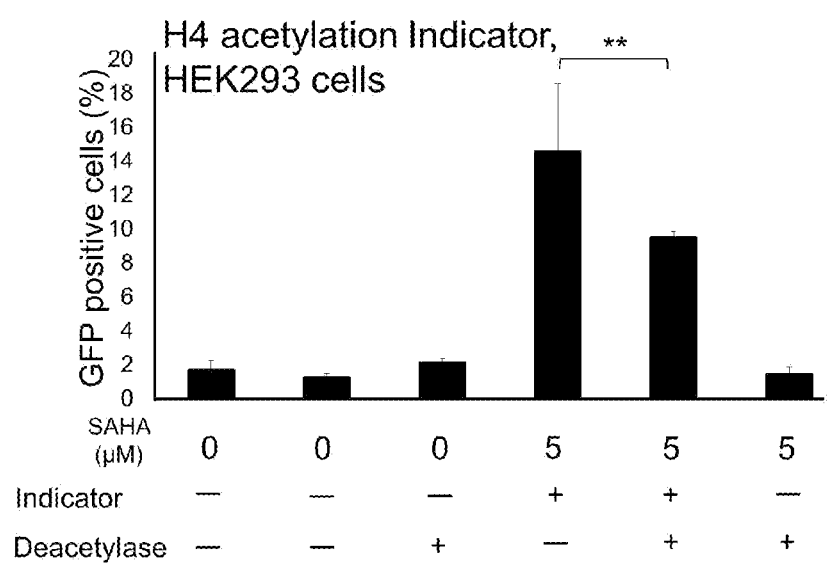
Figure 21:
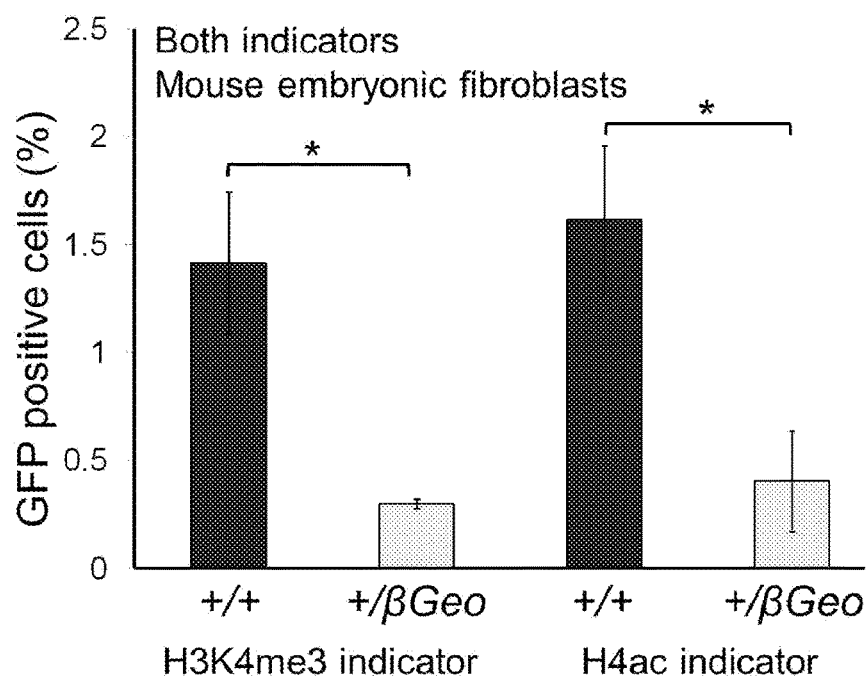
Figure 22A:
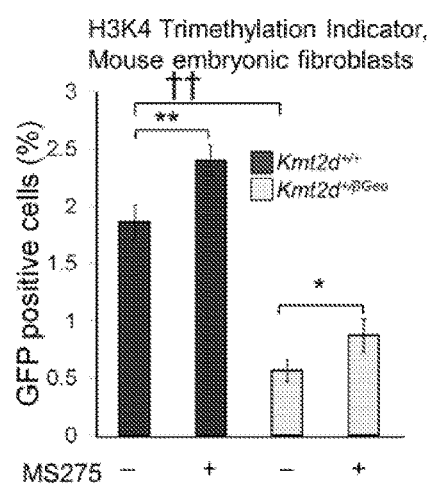
Figure 22B:
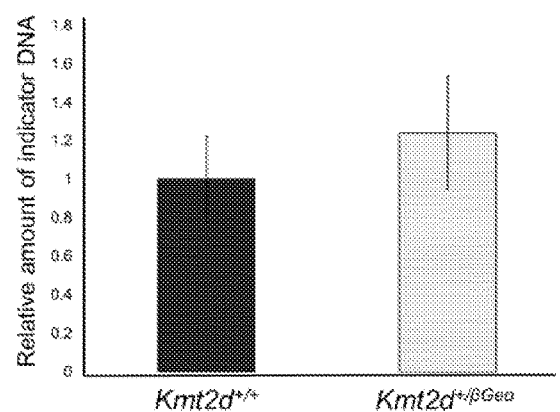
Figure 23:
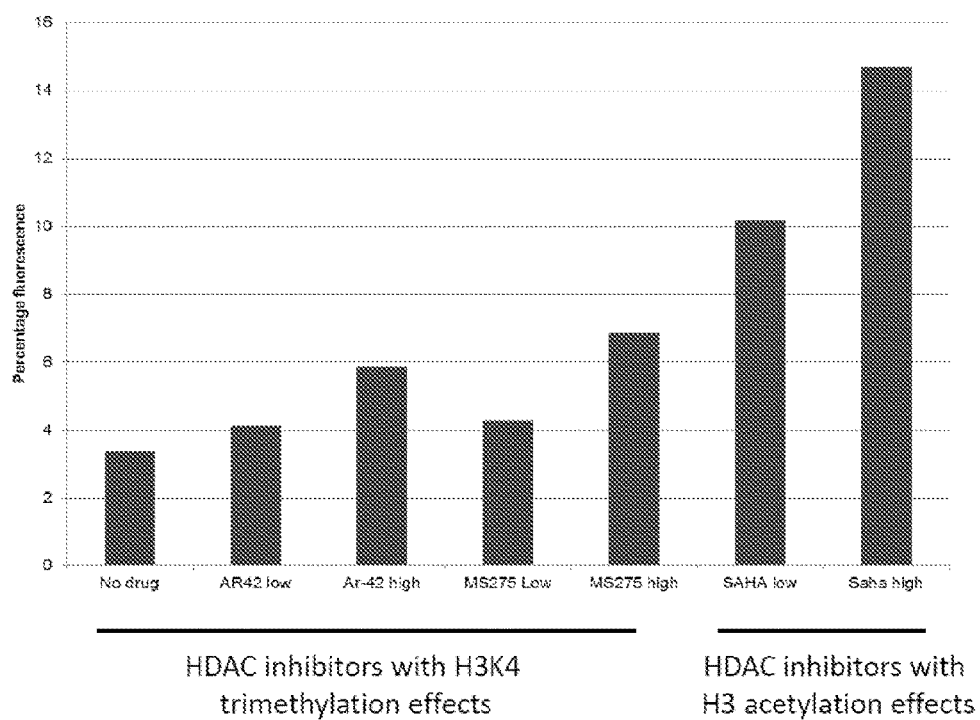
Figure 24A:
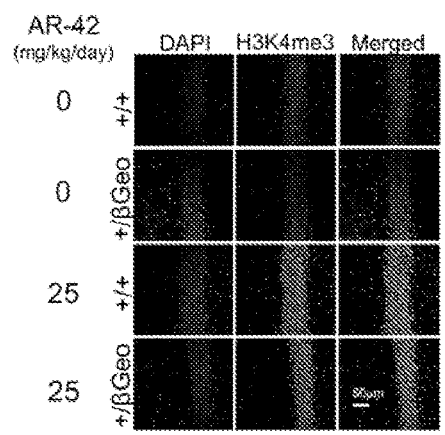
Figure 24B:
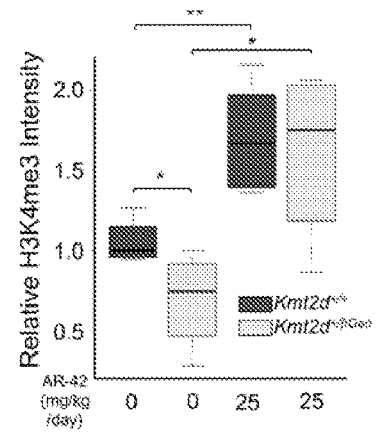
Figure 24C:
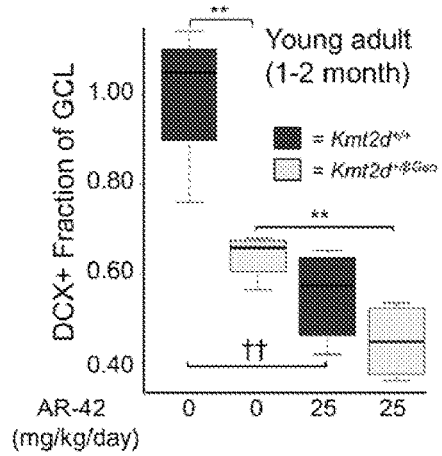
Figure 24D:
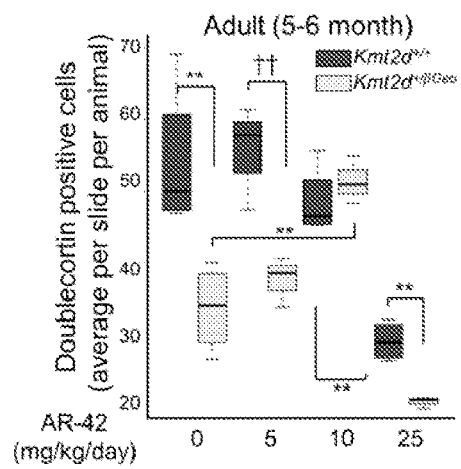
Figure 25A:
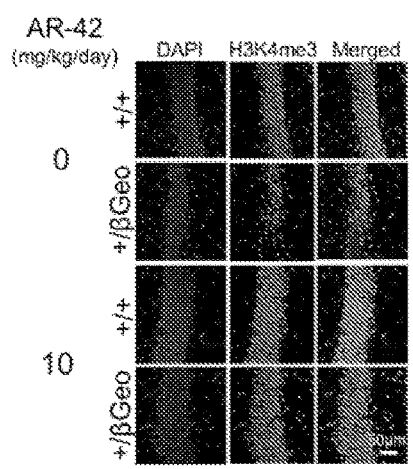
Figure 25B:
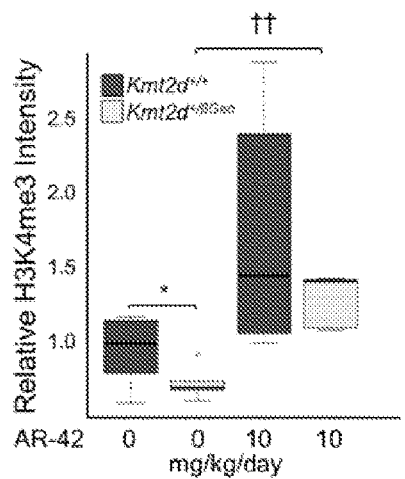
Figure 25C:
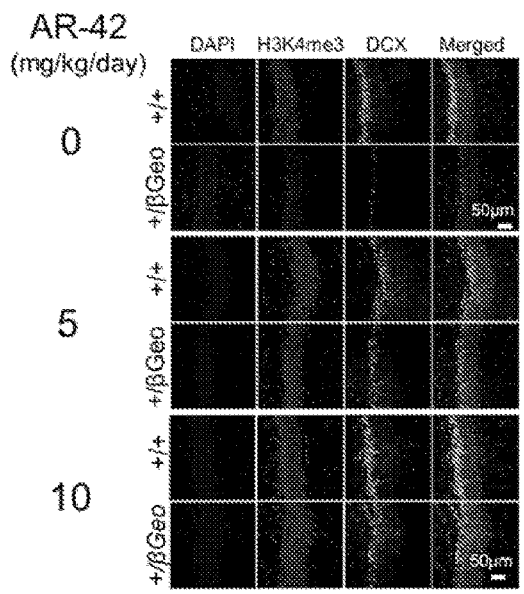
Figure 25D:
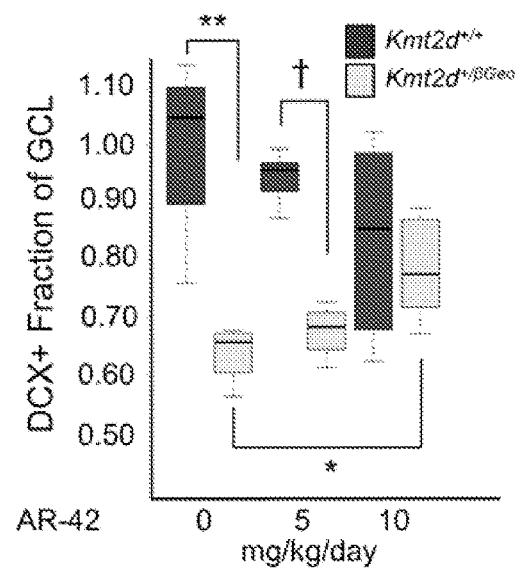
Figure 25E:
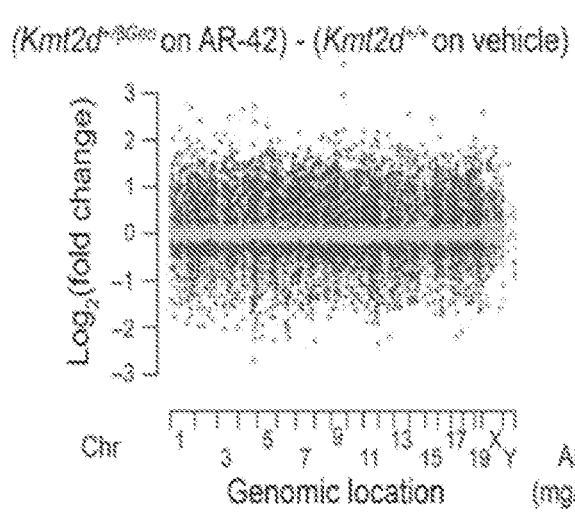
Figure 25F:
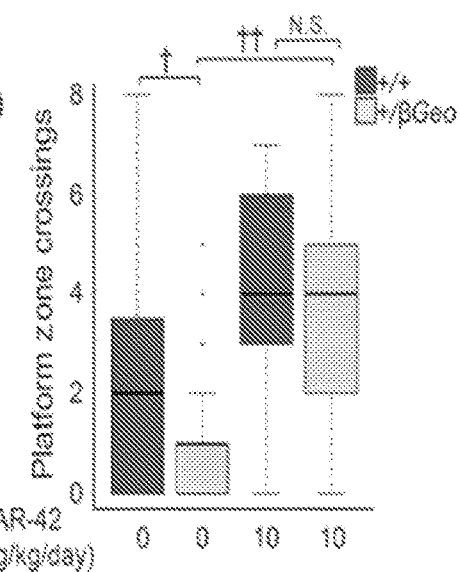
Figure 26:
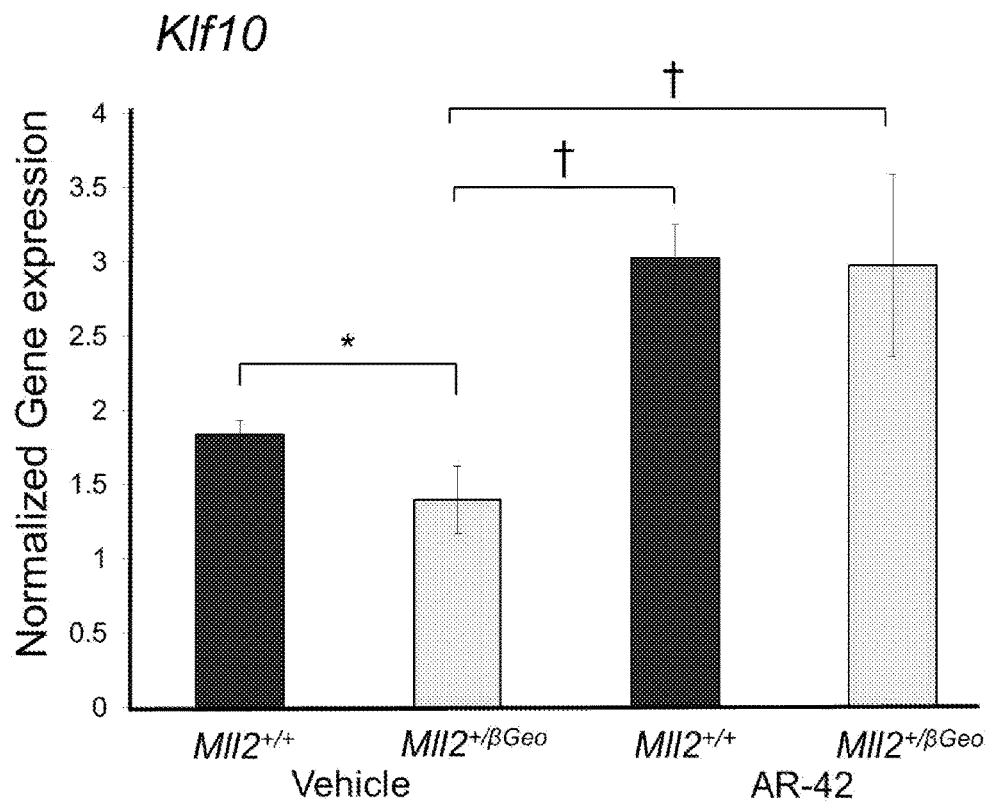
Figure 27A:
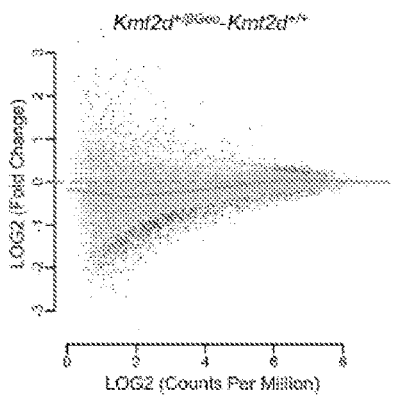
Figure 27B:
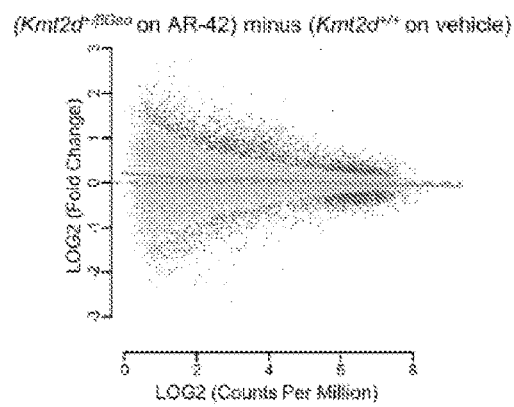
Figure 27C:
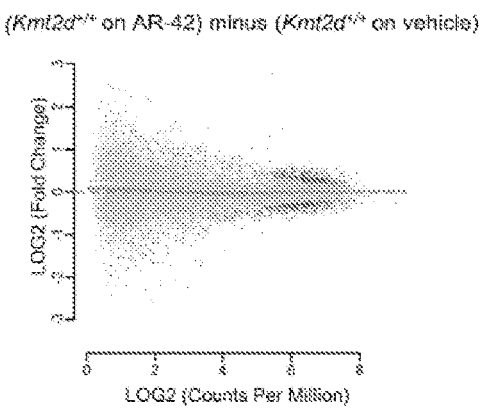
Figure 27D:
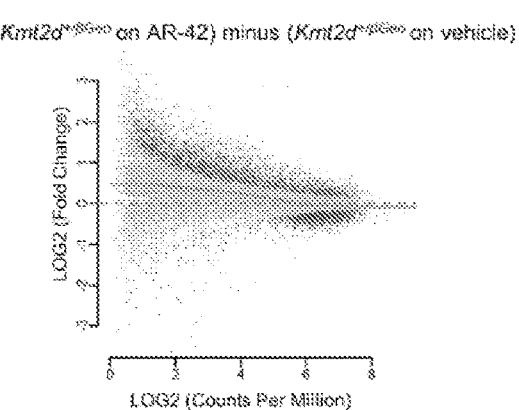
Figure 27E:
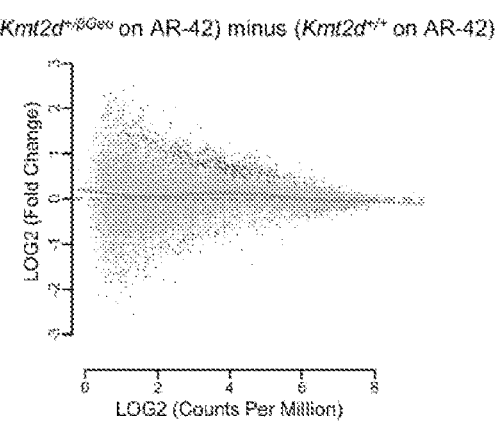
Figure 28A:
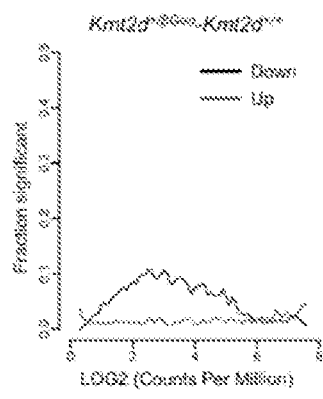
Figure 28B:
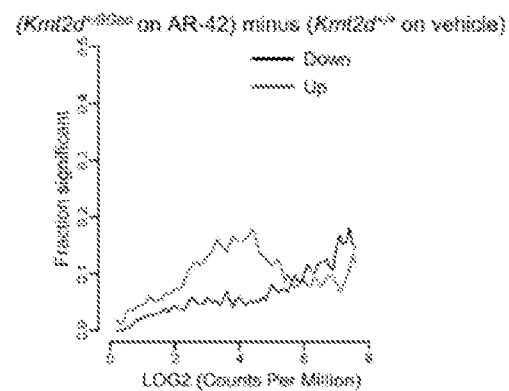
Figure 28C:
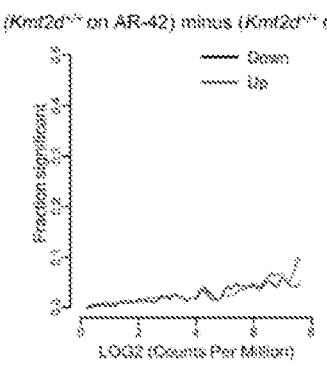
Figure 28D:
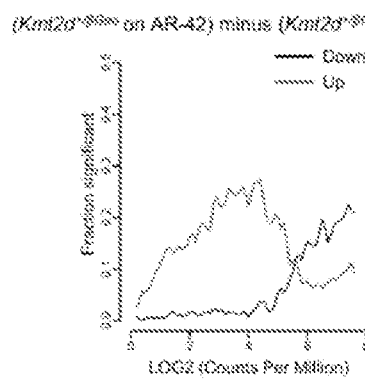
Figure 28E:
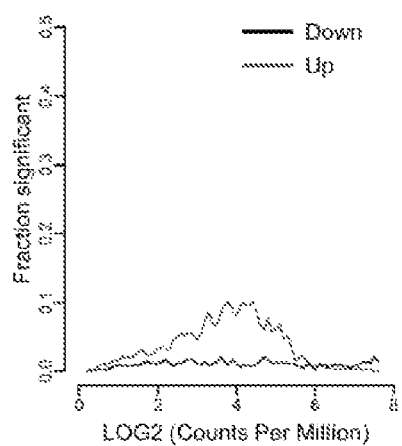
Figure 29:
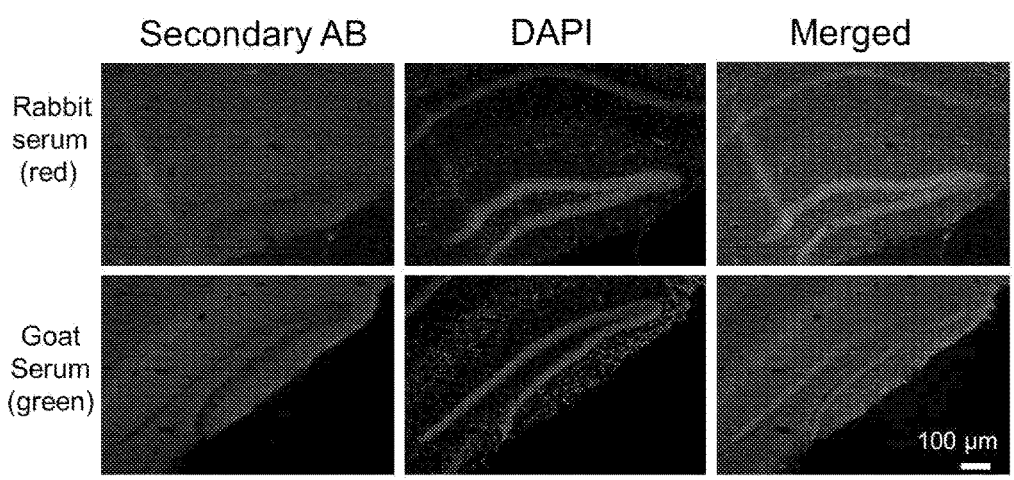
Figure 30:
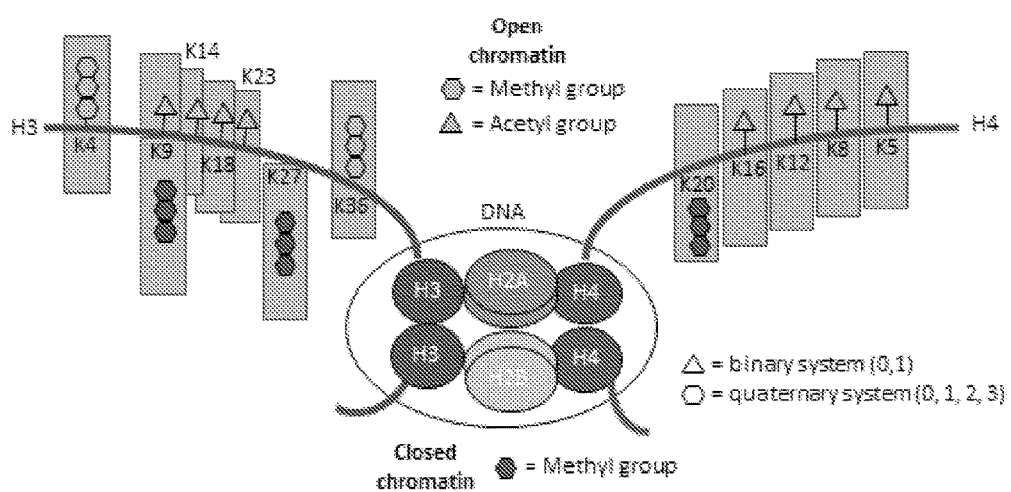

Having thus described the presently disclosed subject matter in general terms, reference will now be made to the accompanying Figures, which are not necessarily drawn to scale, and wherein:

FIG. 1 shows components of the epigenetic machinery. This machinery consists of writers (highlighters) and erasers of marks (for example, trimethylation of lysine 4 on histone H3 (H3K4me3)) as well as readers of those marks. A net balance between systems that remove and add a particular mark must be achieved;

FIG. 2 shows selected Mendelian disorders of the histone machinery caused by alterations of writers (highlighters) and erasers. Acetylation is a binary mark (present or not), and histone lysine methylation a quaternary mark (present as mono-, di-, tri-, or unmethylated). The diagram illustrates these two types of modifications on two of the N-terminal histone tails, histone H3 and histone H4. The writers (highlighters) and erasers place and remove the modifications; some of these are associated with open, permissive chromatin (green), and others are associated with closed, repressive chromatin (red). Based on the enzymatic component of the epigenetic machinery involved and the predicted consequence of the reported mutations for each disorder, the diagram shows conditions that would be expected to shift the balance toward closed chromatin states at target loci (top) and conditions that would be expected to shift the balance toward open chromatin states at target loci (bottom);

FIG. 3 shows therapeutic approaches based on understanding and restoring the balance of chromatin states;

FIG. 4 shows a schematic diagram of an embodiment of the presently disclosed genetically encoded indicator system;

FIG. 5A and FIG. 5B show embodiments of fluorescent indicator constructs used in the presently disclosed subject matter: an acetyl-indicator (FIG. 5A); and a methyl-indicator (FIG. 5B);

FIG. 6A, FIG. 6B, FIG. 6C, FIG. 6D, FIG. 6E, and FIG. 6F show that the Kmt2d$^{+/\beta Geo}$ mouse model of Kabuki syndrome demonstrates hippocampal memory defects. FIG. 6A shows domain organization of MLL family members, with the relative position of the H3K4 methyltransferase SET domain indicated in red and other domains by additional colors. The human and murine chromosomal assignment (Chr) is shown. FIG. 6B shows the Kmt2d$^{\beta Geo}$ targeting event introduces a β-Geo cassette including a strong splice acceptor (SA) sequence and a 3' cleavage and polyadenylation signal (pA) into intron 50 of Kmt2d on mouse chromosome 15 (FIG. 7A). FIG. 6C shows real-time PCR using primers specific for exons 20 or 52 of Kmt2d (arrows) confirms a substantial reduction (~50%) in mRNA corresponding to sequences distal to the β-Geo insertion site when compared to proximal sequences in Kmt2d$^{+/\beta Geo}$ mice, in comparison to Kmt2d$^{+/+}$ littermates. Results reflect three technical replicates for each of 3 Kmt2d$^{+/+}$ and 2 Kmt2d$^{+/\beta Geo}$ mice. FIG. 6D shows that the ChIP-seq reveals a genome-wide deficiency of H3K4me3 in cells from Kmt2d$^{+/\beta Geo}$ mice, when compared to cells from Kmt2d$^{+/+}$ littermates. A positive value indicates a higher locus-specific peak in Kmt2d$^{+/\beta Geo}$ mice. Each point corresponds to a genomic location with a peak in at least one sample. Significantly differentially bound loci are red, while others are gray. FIG. 6E shows there was no difference in positional preference between genotypes during the habituation phase [identical objects (L/R)]. Kmt2d$^{+/\beta Geo}$ mice spent less time with a novel object placed to the left (L) of a habituated object on the right (R) compared to Kmt2d$^{+/+}$ littermates, which also significantly improved from habituation phase [Novel object (L)]. n=13 (+/+), 10 (+/βGeo). FIG. 6F shows that Kmt2d$^{+/\beta Geo}$ mice showed a reduced frequency in platform zone crossings during the probe trial phase of Morris water maze testing, n=48 (+/+), 32 (+/βGeo). *P<0.05. †P<0.005; ††P<0.001;

FIG. 7A and FIG. 7B show the integration site of gene trap in the Kmt2d$^{\beta Geo}$ allele. FIG. 7A shows the DNA sequence of the targeted allele showing the sequence for Kmt2d exon 50 (red) and intron 50 (blue) and the gene trap encoding the β-Geo cassette (purple). FIG. 7B shows immunoprecipitated protein using an antibody directed against KMT2D shows immunoreactivity for β-galactosidase in cellular lysates from Kmt2d$^{+/\beta Geo}$ mice but not Kmt2d$^{+/+}$ littermates. The presence of this hybrid protein suggests that mRNA from the Kmt2d$^{\beta Geo}$ allele is both transcribed and translated;

FIG. 8A, FIG. 8B, and FIG. 8C show that Kmt2d$^{+/\beta Geo}$ mice show overlapping phenotypic features with patients with KS: decreased protrusion of the maxilla over the mandible can be seen when skin is removed (FIG. 8A) and on radiographs (FIG. 8B) in Kmt2d$^{+/\beta Geo}$ mice, when compared to Kmt2d$^{+/+}$ littermates (n≥5 for both groups). FIG. 8C shows that this was verified by a group of investigators blinded to genotype which gave Kmt2d$^{+/+}$ mice a significantly higher maxillary protrusion score than Kmt2d$^{+/\beta Geo}$ littermates. †P<0.005;

FIG. 9 shows that Kmt2d$^{+/\beta Geo}$ mice have context related memory defects. Kmt2d$^{+/\beta Geo}$ show impaired performance in a fear conditioning assay, when compared to Kmt2d$^{+/+}$ littermates. n=20 (+/+), 8 (+/βGeo). P<0.05 (repeated measures ANOVA comparing two genotypes in all time points);

FIG. 10 shows that Kmt2d$^{+/\beta Geo}$ mice show no deficit in flag trial. Kmt2d$^{+/\beta Geo}$ mice and Kmt2d$^{+/+}$ littermates show similar performance during flag trials prior to Morris water maze testing (as reflected by no significant difference in a repeated measures ANOVA), suggesting no inherent impairment to task completion such as visual impairment, in subsequent memory-based testing. N.S., n=15 (+/+), 9 (+/βGeo);

FIG. 11A, FIG. 11B, and FIG. 11C show the assessment of motor function in Kmt2d$^{+/\beta Geo}$ and Kmt2d$^{+/+}$ mice: Kmt2d$^{+/\beta Geo}$ mice did not show any deficit in general activity level (as monitored by beam breaks in open field testing) (FIG. 11A); or grip strength (FIG. 11B), when compared to Kmt2d$^{+/+}$ littermates. FIG. 11C shows comparable swimming speed in the probe trial of the Morris Water Maze. Open field testing: N.S., n=11 (+/+), 11 (+/βGeo); grip strength: N.S., n=18 (+/+), 8 (+/βGeo). MWM probe trial: N.S., n=29 (+/+), 23 (+/βGeo);

FIG. 12A, FIG. 12B, FIG. 12C, and FIG. 12D show the escape latencies during Morris water maze training. FIG. 12A shows average latency to platform zone for Kmt2d$^{+/\beta Geo}$ (yellow) and Kmt2d$^{+/+}$ animals (blue). Repeated measures ANOVA showed no significant difference between groups across all time points. FIG. 12B show Kmt2d$^{+/\beta Geo}$ mice on 10 mg/kg/day of AR-42 (yellow triangle) and Kmt2d$^{+/+}$ animals on 10 mg/kg/day of AR-42 (blue circle). No significant difference is observed. FIG. 12C shows Kmt2d$^{+/+}$ animals with (blue circle) and without (blue square) 10 mg/kg/day of AR-42 (significant difference with P<0.01). FIG. 12D shows Kmt2d$^{+/\beta Geo}$ animals with (yellow rhombus) and without (yellow triangle) 10 mg/kg/day of AR-42. No significant difference is observed. n=32 (+/βGeo, vehicle), 44 (+/+, vehicle), 9 (+/βGeo, AR-42), 14 (+/+, AR-42);

FIG. 13A, FIG. 13B, FIG. 13C, FIG. 13D, FIG. 13E, FIG. 13F, and FIG. 13G show that Kmt2d$^{+/\beta Geo}$ mice demonstrate a global deficiency of H3K4me3 in the DG associated with reduced GCL volume and neurogenesis. FIG. 13A shows that immunofluorescence reveals intense expression of KMT2D (red signal) in the dentate gyrus GCL and pyramidal layer of Kmt2d$^{+/+}$ mice. FIG. 13B shows immunofluorescence showing H3K4me3 (red) and DAPI (blue) in the GCL of Kmt2d$^{+/\beta Geo}$ mice and Kmt2d$^{+/+}$ littermates. FIG. 13C shows that quantification reveals a reduced H3K4me3/DAPI signal intensity ratio within the GCL of Kmt2d$^{+/\beta Geo}$ mice compared to Kmt2d$^{+/+}$ littermates. n=9 (+/+), 5 (+/βGeo). FIG. 13D shows that the calculation of GCL area (red outline) in every sixth brain slice allowed demonstration of reduced GCL volume. FIG. 13E shows Kmt2d$^{+/\beta Geo}$ mice compared to Kmt2d$^{+/+}$ littermates (n=4 (+/+), 5 (+/βGeo)). FIG. 13F and FIG. 13G show that immunofluorescence reveals reduced representation of cells positive for doublecortin (DCX), a marker for neurogenesis, in the GCL of Kmt2d$^{+/\beta Geo}$ mice compared to Kmt2d$^{+/+}$ littermates. n=4 (+/+), 4 (+/βGeo). *P<0.05; ††P<0.001;

FIG. 14 shows that H3K4me3 is decreased in the pyramidal layer in Kmt2d$^{+/\beta Geo}$ mice compared to Kmt2d$^{+/+}$ littermates. H3K4me3 is also significantly reduced in the pyramidal layer of the hippocampus, another cell layer with strong expression of KMT2D protein. n=5 (+/+), 5 (+/βGeo). **P<0.01;

FIG. 15A and FIG. 15B show the body and brain size in Kmt2d$^{+/\beta Geo}$ mice. While Kmt2d$^{+/\beta Geo}$ animals show a significant reduction in body weight, at 5 months of age when compared to Kmt2d$^{+/+}$ littermates (FIG. 15A), there was no significant difference in brain weight (FIG. 15B). Body, n=10 (+/+), 5 (+/βGeo). Brain, N. S., n=14 (+/+), 12(+/βGeo), *P<0.05;

FIG. 16 shows EdU incorporation. Kmt2d$^{+/\beta Geo}$ mice showed reduced incorporation of EdU in the GCL 30 days after the onset of injection, suggesting reduced neurogenesis and long-term neuronal survival, when compared to Kmt2d$^{+/+}$ littermates, as assessed by observers blinded to genotype. n=7 (+/+), 4 (+/βGeo) **P<0.01;

FIG. 17 shows decreased dendrites in DCX+ cells in GCL of Kmt2d$^{+/\beta Geo}$ mice. Immunofluorescence shows that Kmt2d$^{+/\beta Geo}$ animals show an apparent decrease in dendritic arborization of cells that are DCX+, when compared to Kmt2d$^{+/+}$ littermates;

FIG. 18A, FIG. 18B, FIG. 18C, FIG. 18D, FIG. 18E, FIG. 18F, FIG. 18G, FIG. 18H, and FIG. 18I show that the H3k4me3 epigenetic reporter allele demonstrates decreased activity in Kmt2d$^{+/\beta Geo}$ cells. FIG. 18A shows the domain organization encoded by the H4ac and H3K4me3 reporter alleles. The H4ac indicator includes H4 (lysine positions indicated), the C- and N-terminal halves of E-GFP separated by a short linker (L), the TAFII binding domain (BD) and a repetitive nuclear localization signal (NLS). The H3K4me3 indicator includes the H3 and the TAF3-PHD. FIG. 18B shows that the recognition of the histone tail mark by the relevant histone reader leads to reconstitution of GFP structure and function (fluorescence). FIG. 18C and FIG. 18D show that the acetylation indicator demonstrates increasing fluorescence with increasing amounts of the histone deacetylase inhibitor SAHA. FIG. 18E shows that the activity of the H4ac indicator is lost upon mutagenesis of all potential acetylation sites from lysine to arginine. FIG. 18F shows that the H3K4me3 indicator demonstrates a dose dependent response to the histone deacetylase inhibitor AR-42 with decreased cell numbers at higher doses (red line). FIG. 18G shows that the activity is greatly reduced upon mutagenesis of K4 in the H3 tail and D890A/W891A and M882A in the reader pocket. FIG. 18H shows that the H3K4me3 indicator shows reduced activity in murine embryonic fibroblasts (MEFs) derived from Kmt2d$^{+/\beta Geo}$ mice compared to Kmt2d$^{+/+}$ littermates. Both genotypes show a dose-dependent response to AR-42, with Kmt2d$^{+/\beta Geo}$ MEFs achieving untreated wild-type levels of activity at a dose of 5 μM. n=3 (+/+), 3 (+/βGeo), biological replicates for each dose. **P<0.01, ††P<0.001. FIG. 18I shows an experiment demonstrating that lysines on H4 are required for activity of the acetyl reporter: a) 293 cells not transfected but treated with 0 μM, 2.5 μM and 7.5 μM of Vorinostat (left to right); b) 293 cells transfected with reporter that has a single acetylation site with 0 μM, 2.5 μM and 7.5 μM of Vorinostat (left to right); c) 293 cells transfected with reporter with all possible acetylation sites changed from lysine's to arginines with 0 μM, 2.5 μM and 7.5 μM of Vorinostat (left to right);

FIG. 19A and FIG. 19B show that SAHA increases acetylation of the indicator (FIG. 19A) and the saturation curve of the acetylation indicator as seen by % positive cells (FIG. 19B);

FIG. 20 shows that HDAC3 attenuates signal of the H4ac indicator. HEK293 cells stably expressing the H4ac indicator show increased signal upon stimulation with the histone deacetylase SAHA that is attenuated by recombinant expression of HDAC3. n=3 biologic replicates for each state, stable transfection. **P<0.01;

FIG. 21 shows that both indicators demonstrate a deficiency in Kmt2d$^{+/\beta Geo}$ mice. Stable expression of the specified indicator into mouse embryonic fibroblasts (MEFs) demonstrates significant deficiencies in both histone H4 acetylation and H3K4 trimethylation activity in Kmt2d$^{+/\beta Geo}$ MEFs compared to Kmt2d$^{+/+}$ cells, as assessed by the percentage of GFP positive cells. n=4 (+/+), 3 (+/βGeo). *P<0.05;

FIG. 22A and FIG. 22B show improved H3K4 trimethylation activity in Kmt2d$^{+/\beta Geo}$ cells transiently transfected with H3K4 trimethylation indicator and treated with MS275. FIG. 22A shows that Kmt2d$^{+/\beta Geo}$ MEFs show reduced H3K4 trimethylation activity, when compared to Kmt2d$^{+/+}$ cells, that is improved upon treatment with the histone deacetylase MS275. FIG. 22B shows that transiently transfected cells of both genotypes demonstrate comparable transfection efficiency as estimated by real time PCR when compared to a genomic control. n=6 (+/+), 6 (+/βGeo), biological replicates for each concentration, transient transfection. *P<0.05; **P<0.01; ††P<0.001;

FIG. 23 shows HDAC inhibitors with H3K4 trimethylation effects (AR-42 and MS275) and an HDAC inhibitor with H3 acetylation effects (SAHA) at low and high doses;

FIG. 24A, FIG. 24B, FIG. 24C, and FIG. 24D show the in vivo responses to AR-42. FIG. 24A and FIG. 24B show that immunofluorescence reveals increased H3K4me3 in the GCL of Kmt2d$^{+/+}$ and Kmt2d$^{+/\beta Geo}$ mice upon treatment with 25 mg/kg/day of AR-42, with no difference between genotypes in the treated groups, n=4-5 per group. FIG. 24C show that 25 mg/kg/day of AR-42 did not improve DCX expression in Kmt2d$^{+/\beta Geo}$ mice and reduced DCX expression in Kmt2d$^{+/+}$ animals, n=4-6 per group. FIG. 24D shows that DCX expression was improved in older mice (5-6 months) upon treatment of Kmt2d$^{+/\beta Geo}$ mice with 10 mg/kg/day of AR-42, n=3-4 per group. *P<0.05; **P<0.01; ††P<0.001;

FIG. 25A, FIG. 25B, FIG. 25C, FIG. 25D, FIG. 25E and FIG. 25F show the in vivo effects of AR-42. One to two month old mice of both genotypes show an increase in H3K4me3 (FIG. 25A and FIG. 25B) [n=5-6 per group] associated with a dose-dependent increase in neurogenesis in Kmt2d$^{+/\beta Geo}$ mice (FIG. 25C and FIG. 25D) (monitored by normalized DCX expression) [n=4-6 per group] upon treatment with the HDACi AR-42 with no difference between mutant and wild-type animals at a dose of 10 mg/kg/day. FIG. 25E shows that the genome-wide deficiency of H3K4me3 seen in Kmt2d$^{+/\beta Geo}$ mice is improved upon treatment with 10 mg/kg/day AR-42. FIG. 25F shows that the reduced frequency of platform crossing seen during Morris water maze testing of Kmt2d$^{+/\beta Geo}$ mice was normalized upon treatment with 10 mg/kg/day of AR-42. [n=48 (+/+, no treatment), 32 (+/βGeo, no treatment), 14 (+/+, 10 mg/kg/day AR-42), 9 (+/βGeo, 10 mg/kg/day AR-42)]. *P<0.05; **P<0.01; †P<0.005; ††P<0.001;

FIG. 26 shows the AR-42-induced expression of a known Kmt2d target gene. Klf10, a known target gene of Kmt2d (Guo et al. (2012) Proc. Natl. Acad. Sci. U.S.A. 109:17603-8), demonstrates reduced expression in spleen cells of Kmt2d$^{+/\beta Geo}$ mice that is normalized upon treatment with AR-42 n=4 per group. *P<0.05, †P<0.005;

FIG. 27A, FIG. 27B, FIG. 27C, FIG. 27D, and FIG. 27E show MA plots that indicate a shift in the balance of H3K4me3 upon treatment with AR-42: significant differences in the locus-specific intensity of H3K4me3 are indicated in red, with the directionality and magnitude of each peak height reflecting the difference between the indicated states (genotype and AR-42 treatment status). Kmt2d$^{+/\beta Geo}$ animals demonstrate a downward shift compared to Kmt2d$^{+/+}$ littermates (FIG. 27A), which is recovered with AR-42 (FIG. 27B). These data indicate there may be some overcorrection which could be improved in future studies by using ChIP-seq as a biomarker. The difference between AR-42 treated and vehicle treated Kmt2d$^{+/+}$ animals is less notable (FIG. 27C), but obvious when comparing Kmt2d$^{+/\beta Geo}$ on AR-42 compared to Kmt2d$^{+/\beta Geo}$ littermates on vehicle (FIG. 27D) or both genotypes on AR-42 (FIG. 27E). CPM: counts per million, FC: fold change. n=2 (+/βGeo, vehicle), 2 (+/+, vehicle), 2 (+/βGeo, AR-42), 2 (+/+, AR-42);

FIG. 28A, FIG. 28B, FIG. 28C, FIG. 28D and FIG. 28E show a visualization of shifts in balance between states (genotype or AR-42) as a function of intensity demonstrates an abnormality in Kmt2d$^{+/\beta Geo}$ that is responsive to AR-42: Kmt2d$^{+/\beta Geo}$ animals demonstrate a downward shift compared to Kmt2d$^{+/+}$ littermates (FIG. 28A; −2 log Q: 589.5, P<2.2e-16), which is normalized (but somewhat over corrected) with AR-42 (FIG. 28B; −2 log Q: 146.0, P<2.2e-16). The difference between AR-42-treated Kmt2d$^{+/+}$ mice and vehicle treated Kmt2d$^{+/+}$ littermates is less notable (FIG. 28C), but more evident when comparing Kmt2d$^{+/\beta Geo}$ on AR-42 to Kmt2d$^{+/\beta Geo}$ littermates on vehicle (FIG. 28D) or on both genotypes on AR-42 (FIG. 28E) (−2 log Q: 359.9, P<2.2e-16). n=2 (+/βGeo, vehicle), 2 (+/+, vehicle), 2 (+/βGeo, AR-42), 2 (+/+, AR-42);

FIG. 29 shows serum control experiments for antibodies used for immunofluorescence. Non-specific binding was not observed when sections were sequentially exposed to serum from the same species matching the primary antibody for each experiment (i.e. rabbit for KMT2D and H3K4me3 and goat for doublecortin), followed by the secondary antibody used for KMT2D and H3K4me3 (anti-rabbit) or doublecortin (anti-goat); and FIG. 30 shows histone modifications relating to acetylation and methylation for H3 and H4 tails, such as H3K9me3, H3K27me3, H3K36me3 and H3K20me3.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides fusion protein reporters that may be used to monitor the modification of histones in cells, including real-time monitoring of histone modification in living cells. These novel reporters are based on a circularly permutated green fluorescent protein (GFP) that lacks fluorescence unless the two parts of GFP are brought into close proximity by external forces, and therefore does not rely on Förster resonance energy transfer (FRET). Use of these novel reporters allows the determination of the level of modification of histones, including the level of acetylation, methylation, and phosphorylation. These determinations can be compared to control levels and thus allow diagnosis of disorders that are associated with levels of histone modification that differ from normal levels. The reporters can also be used to evaluate candidate pharmaceutical agents for use in prevention and/or treatment of histone modification-associated disorders, for example histone-modification-associated disorders. These evaluations can be done in cells, tissues, samples, or in subjects to determine the effect of pharmaceutical agents on the level of histone modification. In addition, the fusion protein reporters of the presently disclosed subject matter can be utilized in non-invasive methods to assess cellular response to external stimuli.

I. Genetically Encoded Histone Reporter Allele Constructs

A. Histone Modifications and the Balance between Open and Closed Chromatin States The presently disclosed subject matter provides a genetically encoded histone reporter allele system that can be used to monitor activity of any histone maintenance machinery component in live cells. Histones, which provide scaffolding support for DNA in the nuclei of all eukaryotic cells, play a role in the initial points of regulation in gene transcription. Histone modification plays a role in cell differentiation, imprinting, cell cycle progression, DNA damage/repair/recombination, chromosomal stability and disease, and thus are involved in many cell regulation functions. Histone modifications are involved in these cell processes and abnormal histone modification levels are associated with cell division and differentiation disorders. Such histone-modification-associated disorders include, but are not limited to: cancer (including but not limited to leukemia, breast cancer, and ovarian cancer), exposure to toxic chemicals, viruses, developmental disorders, and cell division and or cell development disorders.

Histone proteins can be covalently modified in various ways to influence the transcription levels of the proximal DNA. The core nucleosome particle is a histone octamer consisting of two copies each of H2A, H2B, H3 and H4, wrapped inside 146 base pairs of DNA. Covalent modifications to the N-terminal tails of H3 and H4, such as phosphorylation, acetylation, methylation, ubiquitination, or ADP-ribosylation, give rise to structural changes and create binding sites for signaling proteins that regulate transcription. The first three of these modifications, performed respectively by kinases, acetyltransferases, and methyltransferases, have well-established roles in the regulation of chromatin status and hence of gene transcription.

The DNA methylation machinery and the histone machinery affect the expression of many genes in trans (Berdasco & Esteller (2013) *Hum. Genet.* 132:359-83; Wolffe (1994) *Trends Biochem. Sci.* 19:240-44). Within this group, genetic mutations may occur in writers, erasers, or readers of epigenetic marks. The writers of epigenetic marks, which can be conceptualized as a set of highlighters, place the appropriate modifications on particular regions of the genome based on the cell type, developmental stage, and metabolic state of the cell. These marks "highlight" individual regions for use or disuse depending on whether the mark favors a more open or more closed chromatin state (FIG. 1). The erasers of epigenetic marks remove these same marks, favoring the opposite chromatin states (FIG. 1). The readers of epigenetic marks recognize and interpret particular marks locally and give cells a mechanism for keeping track of the overall chromatin state (FIG. 1).

Components of the epigenetic machinery are shown in FIG. 1. This machinery consists of writers (highlighters) and erasers of marks (for example, trimethylation of lysine 4 on histone H3 (H3K4me3)) as well as readers of those marks. A net balance between systems that remove and add a particular mark must be achieved. In many ways, the interacting epigenetic systems have certain distinct aspects that make them powerful final integrators of cellular signals (Jaenisch and Bird (2003) *Nat. Genet.* 33(Suppl.):245-545). For instance, many of the marks placed/removed by writers/erasers can directly affect gene expression, either in a permissive (H3K4me3, shown) or nonpermissive (H3K9me3, not shown) manner. This change in expression, presumably of multiple genes, has the potential to form feedback loops by affecting the amount and availability of the modification in question. Various internal metabolites can directly affect the prevalence of marks. For instance, S-adenosyl-methionine (SAM) is a donor for methylation reactions, including both DNA and histone methylation. Use of critical metabolic intermediates like SAM as donors for histone tail modifications or for DNA methylation allows environmental influences to impact and be integrated into the system and to potentially affect gene expression directly (Lu and Thompson (2012) *Cell Metab.* 16:9-177).

To ensure appropriate cell type-specific gene expression, a balance must be achieved between the activity of the two opposing systems (writers and erasers) and the subsequent placement of their respective marks (FIG. 1), ensuring that the appropriate composition of chromatin is present at particular gene promoters. Although a steady-state balance of chromatin marks is likely achieved at any given time, the opposing histone systems are likely to be dynamic in nature (Ficz et al. (2005) *Development* 132:3963-76; Mito et al. (2007) *Science* 315:1408-11), allowing the cell to rapidly respond to changes in environmental signals by altering gene expression at specific loci. The histone machinery (as well as some components of the DNA methylation machinery) is enormously redundant, perhaps reflecting the critical importance of maintaining this balance in many different cell types (FIG. 1).

Selected Mendelian disorders of the histone machinery caused by alterations of writers (highlighters) and erasers are shown in FIG. 2. Acetylation is a binary mark (present or not), and histone lysine methylation a quaternary mark (present as mono-, di-, tri-, or unmethylated). The diagram illustrates these two types of modifications on two of the N-terminal histone tails, histone H3 and histone H4. The writers (highlighters) and erasers place and remove the modifications; some of these are associated with open, permissive chromatin (FIG. 2, green), and others are associated with closed, repressive chromatin (FIG. 2, red). Based on the enzymatic component of the epigenetic machinery involved and the predicted consequence of the reported mutations for each disorder, the diagram shows conditions that would be expected to shift the balance toward closed chromatin states at target loci (FIG. 2, top) and conditions that would be expected to shift the balance toward open chromatin states at target loci (FIG. 2, bottom). The former category includes Rubinstein—Taybi syndrome (RTS) (Petrij et al. (1995) *Nature* 376:348-5192; Roelfsema et al. (2005) *Am. J. Hum. Genet.* 76:572-80), Kabuki syndrome (KS) (Lederer et al. (2012) *Am. J. Hum. Genet.* 90:119-24; Ng et al. (2010) *Nat. Genet.* 42:790-93), Wiedemann-Steiner syndrome (WSS) (Jones et al. (2012) *Am. J. Hum. Genet.* 91:358-64), and possibly Weaver syndrome (WS) and Sotos syndrome (SS) (Gibson et al. (2012) *Am. J. Hum. Genet.* 90:110-18; Tatton-Brown et al. (2011) *Oncotarget* 2:1127-33; Kurotaki et al. (2002) *Nat. Genet.* 30:365-66); the latter category includes brachydactyly-mental retardation syndrome (BDMR) (Williams et al. (2010) *Am. J. Hum. Genet.* 87:219-28), Kleefstra syndrome (KLFS) (Kleefstra et al. (2006) *Am. J. Hum. Genet.* 79:370-776), Claes-Jensen syndrome (CJS) (Jensen et al. (2005). *Am. J. Hum. Genet.* 76:227-366), and Sotos syndrome (SS) (Kurotaki et al. (2002) *Nat. Genet.* 30:365-666).

Therapeutic approaches based on understanding and restoring the balance of chromatin states are shown in FIG. 3. If abnormalities of the expression of target genes are the culprit, the target genes would be expected to be fully functional, albeit improperly expressed, in patients with these disorders. For instance, Kabuki syndrome (KS) is related to a deficiency of trimethylation of lysine 4 on histone H3 (H3K4me3) or an inability to remove H3K27me3, marks that are predominantly seen in open and repressive chromatin, respectively. If the pathophysiology of KS is related to an imbalance between open and closed chromatin states (FIG. 3, top left), with an inability to use critical gene transcripts, then this balance could be restored by inhibiting the transition to closed chromatin with a histone deacetylase (HDAC) inhibitor (FIG. 3, bottom left). In contrast, brachydactyly—mental retardation syndrome (BDMR) would be expected to lead to an overrepresentation of open chromatin states (FIG. 3, top right), with excessive transcription of disease-relevant target genes. Therefore, a histone acetyltransferase (HAT) inhibitor could be a useful therapeutic strategy (FIG. 3, bottom right).

B. Histone Reporter Allele Constructs

In one embodiment of the presently disclosed subject matter, fusion protein reporter constructs are provided. The constructs encode fusion proteins that include a core comprising a histone-modification-specific binding domain, a histone polypeptide substrate, and a flexible linker region flanked on one side by a region encoding a C-terminal portion of a circularly permutated fluorescent protein and on the other side by a region encoding the N-terminal portion of the circularly permutated fluorescent protein. In some embodiments, the histone polypeptide substrate is selected from the group consisting of H3 or H4. In some embodiments, the histone polypeptide is selected from the group consisting of the N-terminus of H3 and the N-terminus of H4. In some embodiments, the histone modification is selected from the group consisting of acetylation, methylation, and phosphorylation. In some embodiments, the histone modification-specific binding domain is selected from the group consisting of a TBP associated factor II (TAFII) bromodomain and a TBP associated factor III (TAFIII) homeodomain. In certain embodiments, the fusion protein reporter also includes a targeting polypeptide, associated with the fusion protein. In some embodiments, the targeting polypeptide comprises at least one a nuclear localization sequence (NLS), particularly wherein the targeting polypeptide comprises a repeated NLS. In some embodiments, the circularly permutated fluorescent protein comprises a circularly permutated green fluorescent protein. Of course, the presently disclosed subject matter contemplates the use of other circularly permutated fluorescent proteins, such as circularly permutated red and circularly permutated yellow fluorescent proteins, for use in the fusion protein reporter, as will be appreciated by those skilled in the art.

Previously, Förster resonance energy transfer (FRET) based epigenetic activity systems have been created (Lin and Ting (2004) *Angew Chem Int Ed Engl.* 24; 43 (22):2940-3; Lin et al. (2004) *J. Am. Chem. Soc.* 19; 126(19):5982-3; U.S. Pat. No. 7,056,683). However, FRET-based assays need a complex technological setup which is not widely available and FRET-based assays have been much more difficult to introduce into transgenic mouse models.

The presently disclosed non-FRET-based histone indicator system is based on a circularly permutated fluorescent protein (e.g., green fluorescent protein (GFP)) that lacks fluorescence unless the two parts of the circularly permutated fluorescent protein (e.g., GFP) are brought into close proximity by external forces (Baird et al. (1999) *Proc. Natl. Acad. Sci. U.S.A.* 28; 96(20):11241-6). As exemplified using GFP, reporter alleles encode halves of green fluorescent protein separated by a flexible linker region (Baird et al. (1999) *Proc. Natl. Acad. Sci.* 96: 11241-6) with a histone tail and a histone reader at the N- and C-termini, respectively. When the histone tail corresponding to either H4 or H3 is modified by acetylation or methylation, respectively, GFP structure and function are reconstituted, as detected by a fluorescent readout. The constructs are targeted to the nucleus through a nuclear localization signal (NLS). Mutants were also created that knocked out the activity of the indicator allele.

A schematic diagram of one embodiment of the presently disclosed genetically encoded indicator system is shown in FIG. 4. FIG. 5A and FIG. 5B show additional embodiments of fluorescent indicator constructs corresponding to an acetyl-indicator (FIG. 5A) and a methyl-indicator (FIG. 5B).

In one embodiment, the genetically encoded histone reporter allele system of the presently disclosed subject matter can be used to monitor histone acetylation. An acetyl reporter protein quantifies the activity of the acetylation machinery (acetylation of H4 specifically at the 5th, 8th, 12th and 16th Lysine's) and comprises an H4 tail on one end (the target for acetylation) and a TBP associated factor II (TAFII) bromodomain on the other end of the reporter protein (FIG. 5A). The TAFII bromodomain only recognizes and binds to the acetylated H4 tail, resulting in reconstitution of GFP structure and function (i.e. fluorescence). Therefore, the reporter protein has no fluorescence unless it is acetylated by the acetylation system of the nucleus of the cell.

In another embodiment, the genetically encoded histone reporter allele system of the presently disclosed subject matter can be used to monitor histone H3K4 trimethylation. An H3K4 trimethylation reporter is based on the H3 tail on one end and the TBP associated factor III (TAFIII) homeodomain on the other end (FIG. 5B); the TAFIII homeodomain only identifies and binds to trimethylated K4 on H3. When the H3K4 site gets trimethylated, the TAFIII homeodomain can bind to the modified H3 tail and bring the two parts of the separated GFP in close proximity. The activity of the epigenetic modification system can be quantified through fluorescence. In another embodiment, the genetically encoded histone reporter allele system of the presently disclosed subject matter can be used to monitor any histone modification for which a specific reader domain is known (see, e.g., FIG. 2 and FIG. 30). For example, FIG. 30 shows several additional histone modifications within the scope of the presently disclosed subject matter relating to H3 and H4 tails and types of acetylation and methylation (such as H3K9me3, H3K27me3, H3K36me3 and H3K20me3). These and other histone modifications are within the scope of the presently disclosed subject matter, including but not limited to phosphorylation, ubiquitylation, sumoylation, butyrylation, proprionylation, glycylation, citrullination, and ADP-ribosylation (see Table 3 in Example 3 below). Furthermore, as additional specific reader domains are discovered for particular histone modifications, one of skill in the art would readily be able to incorporate such reader domains into the presently disclosed subject matter to cover additional histone modification systems.

In some embodiments, the presently disclosed subject matter also provides expression vectors comprising an expression cassette encoding a fusion protein reporter of any of the foregoing embodiments.

"Histone modification-associated disorders" as used herein means a condition with an altered level of histone modification in a cell, tissue, or subject. An "altered" level means the level differs in a statistically significant way from the level in a normal or control cell, tissue, or subject. As will be understood by one of ordinary skill in the art, the level of protein modification may be an increase or a decrease of the normal or control level and be indicative of a protein modification-associated disorder. Thus, for example, an increased level of histone modification may indicate, and can be used as a marker for, a histone-modification-associated disorder and a decreased level of histone modification may indicate, and can be used as a marker for a histone-modification-associated disorder.

As used herein, the term "fusion protein reporter" means a fusion protein that includes elements for determining the level of histone modifications in a cell. Generally, such elements include, but are not limited to, a core comprising a histone-modification-specific binding domain, a histone polypeptide substrate, and a flexible linker region flanked on one side by a region encoding a C-terminal portion of a circularly permutated green fluorescent protein (GFP) and on the other side by a region encoding the N-terminal portion of the circularly permutated GFP. When the conformation of the binding protein moiety changes upon substrate histone polypeptide modification, the two halves of the permutated GFP come closer together and fluorescence is increased accordingly. Thus, determination of the level of fluorescence allows determination of the level of specific histone modification of the fusion protein reporter core. In one embodiment, the level of histone modification in a fusion protein reporter of the presently disclosed subject matter is substantially similar to the level of modification of endogenous histones, thus the fusion protein reporter can be used to assess the level of endogenous histone modification in cells.

As used herein, the term "histone-modification-specific binding domain" means a region of a polypeptide that specifically binds to its corresponding modified histone polypeptide but not to the unmodified form of the histone polypeptide. For example, an acetylation-specific binding domain specifically binds to an acetylated histone polypeptide (e.g. acetylated H3 or H4, or fragment thereof), but does not specifically bind to the unacetylated form of the histone polypeptide. Similarly, a methylation-specific binding domain specifically binds to a methylated histone polypeptide (e.g. methylated H3 or H4 or fragment thereof), but does not specifically bind to the unmethylated form of the histone polypeptide, and a phosphorylation-specific binding domain specifically binds to a phosphorylated histone polypeptide (e.g. phosphorylated H3 or H4 or fragment thereof), but does not specifically bind to the unphosphorylated form of the polypeptide.

Examples of histone-modification-specific binding polypeptides for detecting histone acetylation include, but are not limited to, a bromodomain, e.g., a TBP associated factor II (TAFII) bromodomain (as described in the Examples below). As used herein, the term "bromodomain" includes, but is not limited to, bromodomains from: GCN5, P/CAF, TAF$_{II}$250, CBP, BRG1, Swi2, and Sth1. (for reviews see: *FEBS Lett* 513(1):124-8 (2002), *Front Biosci* 6:D1019-23 (2001); and *Nat Struct Biol* 6(7):601-4 (1999)).

Examples of histone-modification-specific binding polypeptides for detecting histone methylation, include, but are not limited to, a chromodomain and a TBP associated factor III (TAFIII) homeodomain (as described in the Examples below). As used herein, the term "chromodomain" includes, but is not limited to: HP1, MRG15, MRG-1, cynCDY, Hrp3, dMi-2, CHD5, Swi6, and pdd3p (for review see: *Nature* 407(6802):405-9 (2000).

Examples of histone-modification-specific binding polypeptides for detecting phosphorylation modification include, but are not limited to a 14-3-3, FHA or WW domains (for 14-3-3 see Fu et al. (2000) *Annu. Rev. Pharmacol. Toxicol.* 40, 617-647; Aitken et al. (1995) *Biochem. Soc. Trans.* 23, 605-611; for FHA and WW domains see Yaffe & Elia (2001) *Curr. Opin. Cell Biol.* 13, 131-138).

Additional modification-specific binding domains will be known to those of ordinary skill in the art as will sequence variations of the above-described modification-specific binding domains, which can also be use in the claimed presently disclosed subject matter.

The fusion protein reporters of the presently disclosed subject matter may include a single modification-specific binding domain or may include more than one modification-specific binding domain. If more than one modification-specific binding domain is included, they may be in tandem, e.g. they may abut each other, or may be separated by other elements of the fusion protein reporter, for example, the two or more modification specific binding domains may be separated from each other by a histone polypeptide sequence or a linker.

The fusion protein reporters of the presently disclosed subject matter also include a histone polypeptide substrate. As used herein, the term "histone polypeptide substrate sequence" means an amino acid sequence that includes all or part of a histone polypeptide amino acid sequence. The polypeptide substrate sequences of the presently disclosed subject matter may include, for instance, either complete or partial sequences of H2A, H2B, H3 and/or H4. The H3 and H4 amino acid sequences may encompass the N-terminus of the H3 or H4 polypeptides.

As used herein, a "circularly permutated green fluorescent protein (GFP)" means a GFP variant well known in the art (see, e.g., U.S. Pat. Nos. 7,960,144 and 8,372,635). A green fluorescent protein (GFP) is a protein that emits green light, and a blue fluorescent protein (BFP) is a protein that emits blue light. GFPs have been isolated from the Pacific Northwest jellyfish, *Aequorea victoria*, the sea pansy, *Renilla reniformis*, and *Phialidium gregarium*. See, Ward et al. (1982) *Photochem. Photobiol.* 35:803-808; and Levine et al. (1982) *Comp. Biochem. Physiol.*, 72B:77-85.

Methods of performing assays on fluorescent materials are well known in the art and are described in, e.g., Lakowicz, J. R., Principles of Fluorescence Spectroscopy, New York:Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

The fusion protein reporter of the presently disclosed subject matter also includes a flexible linker region flanked on one side by a region encoding a C-terminal portion of a circularly permutated GFP and on the other side by a region encoding the N-terminal portion of the circularly permutated GFP. The linker moiety may be, for instance, a peptide that can include between about 1 and about 50 amino acid residues, or in some instances between about 1 amino acid residue and about 30 amino acid residues, or in some instances between 2 and about 15 residues. The linker can be a polypeptide with any amino acid sequence. In some embodiments, the linker moiety may be -Gly-Gly-. Linker molecules are described, for example, in Huston et al. (1988) *PNAS* 85:5879-5883; Whitlow et al. (1993) *Protein Engineering* 6:989-995; and Newton et al. (1996) *Biochemistry* 35:545-553.

The fusion protein reporter of the presently disclosed subject matter may also include a targeting polypeptide associated with the fusion protein. A targeting polypeptide may be covalently or non-covalently attached to the fusion protein. Examples of target polypeptides, also referred to herein as "localization sequences" include, but are not limited to, a receptor ligand, a nuclear localization sequence (NLS), a nuclear export signal (NES), a plasma membrane targeting signal, plasma membrane targeting sequences, p53, tubulin, a histone-binding protein, a histone protein, or a nuclear protein. Other targeting polypeptides with similar properties are known to those skilled in the art, or can be readily ascertained without undue experimentation.

In a particular embodiment, the targeting polypeptide comprises at least one a nuclear localization sequence (NLS), particularly wherein the targeting polypeptide comprises a repeated NLS.

Fragments of fusion protein reporter polypeptides can also be used in some aspects of the presently disclosed subject matter. Polypeptide fragments useful in the fusion protein reporter of the presently disclosed subject matter are preferably those fragments that retain a distinct functional capability of the polypeptide. Functional capabilities that can be retained in a fragment of a polypeptide include the ability to interact with the other fusion protein reporter polypeptides of the presently disclosed subject matter. As will be recognized by those skilled in the art, the size of a preferred fragment will depend upon factors such as whether the fragment is of sufficient size to interact with the other fusion protein reporter polypeptides and thus enable use of the fusion protein reporter in the methods described herein. Thus, some fragments of fusion protein reporter polypeptides will consist of longer segments while others will consist of shorter segments, (e.g. 5, 6, 7, 8, 9, 10, 11, 12, 13, 14, 15, 16, 17, 18, 19, 20, 21, 22, 23, 24, 25, or more amino acids long), including each integer up to the full length of the fusion protein reporter polypeptides. An example of such full-length fusion reporter polypeptides, although not intended to be limiting are full-length H2A, H2B, H3 and/or H4 polypeptides, from any species.

The skilled artisan will also realize that conservative amino acid substitutions may be made in fusion protein reporter polypeptides (which as used herein include histone polypeptide substrates and/or histone-modification-specific binding domains) to provide functionally equivalent variants, or homologs of the foregoing polypeptides, i.e, the variants retain the functional capabilities of the fusion protein reporter polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants or homologs of the fusion protein reporter polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. For example, upon determining that a peptide is a fusion protein reporter polypeptide-equivalent polypeptide, one can make conservative amino acid substitutions to the amino acid sequence of the peptide, and the resulting fusion protein reporter polypeptide-equivalent polypeptide can be tested using methods enclosed herein to determine whether it retain its specific binding characteristics in the fusion protein reporter.

Conservative amino-acid substitutions in the amino acid sequence of fusion protein reporter polypeptides to produce functionally equivalent variants of fusion protein reporter polypeptides typically are made by alteration of a nucleic acid encoding fusion protein reporter polypeptides. Such substitutions can be made by a variety of methods known to one of ordinary skill in the art. For example, amino acid substitutions may be made by PCR-directed mutation, site-directed mutagenesis according to the method of Kunkel (Kunkel (1985) *Proc. Nat. Acad. Sci. U.S.A.* 82: 488-492), or by chemical synthesis of a gene encoding a fusion protein reporter polypeptide. Where amino acid substitutions are made to a small unique fragment of a fusion protein reporter polypeptide, the substitutions can be made by directly synthesizing the peptide. The activity of functionally equivalent fragments of fusion protein reporter polypeptides can be tested by including the altered fusion protein reporter polypeptide in a fusion protein reporter and testing for the functional capability of the fusion protein reporter polypeptide as disclosed herein. Peptides that are chemically synthesized can be tested directly for function, e.g., for activity in the fusion protein reporter.

The introduction of fusion protein reporters into cells allows those of skill in the art to monitor the level of histone modification in those cells. Additionally, use of the fusion protein reporters allows diagnosis of protein modification disorders, for example histone modification disorders as described herein. Such disorders can be identified by abnormal or aberrant levels of histone modification in cell samples. The terms "abnormal" and "aberrant" refer to either or both of a decreased level of histone modification (including no detectable protein modification) or increased level of histone modification as compared to the level of protein modification in a control sample or cell.

The diagnostic methods of the presently disclosed subject matter can be used to detect the presence of a disorder associated with aberrant histone modification levels, as well as to assess the progression and/or regression of the disorder such as in response to treatment (e.g., chemotherapy, pharmaceutical, or radiation). According to this aspect of the presently disclosed subject matter, the method for diagnosing a disorder characterized by aberrant histone modification involves: detecting in a first biological sample obtained from a subject, the level of histone modification, wherein decreased level of protein modification compared to a control sample indicates that the subject has a disorder characterized by aberrant histone modification.

The presently disclosed subject matter also relates in part to the construction of expression vectors and the expression of genes in transfected cells involves the use of molecular cloning techniques also well known in the art (see, e.g., Sambrook et al., Molecular Cloning—A Laboratory Manual, Cold Spring Harbor Laboratory, Cold Spring Harbor, N.Y., (1989). In some aspects of the presently disclosed subject matter, an expression vector comprises an isolated nucleic acid molecule encoding any of the fusion protein reporter constructs as disclosed herein, preferably operably linked to a promoter. In a related aspect, host cells transformed or transfected with such expression vectors also are provided.

As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids, and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art, e.g., β-galactosidase or alkaline phosphatase, and genes which visibly affect the phenotype of transformed or transfected cells, hosts, colonies or plaques. Preferred vectors are those capable of autonomous replication and expression of the structural gene products present in the DNA segments to which they are operably joined.

As used herein, a coding sequence and regulatory sequences are said to be "operably joined" or "operably linked" when they are covalently linked in such a way as to place the expression or transcription of the coding sequence under the influence or control of the regulatory sequences. As used herein, "operably joined" and "operably linked" are used interchangeably and should be construed to have the same meaning. In embodiments of the presently disclosed subject matter in which it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Often, such 5' non-transcribed regulatory sequences will include a promoter region which includes a promoter sequence for transcriptional control of the operably joined gene. Regulatory sequences may also include enhancer sequences or upstream activator sequences as desired. The vectors of the presently disclosed subject matter may optionally include 5' leader or signal sequences. The choice and design of an appropriate vector is within the ability and discretion of one of ordinary skill in the art.

It will also be recognized that the presently disclosed subject matter embraces the use of the fusion protein reporter DNA and genomic sequences in expression vectors, as well as to transfect host cells and cell lines, be these prokaryotic, e.g., *E. coli*, or eukaryotic, e.g., CHO cells, COS cells, yeast expression systems, and recombinant baculovirus expression in insect cells. Especially useful are mammalian cells such as human, mouse, hamster, pig, goat, primate, etc. They may be of a wide variety of tissue types, including mast cells, fibroblasts, oocytes, and lymphocytes, and may be primary cells and cell lines. Specific examples include dendritic cells, U293 cells keratinocytes, peripheral blood leukocytes, bone marrow stem cells and embryonic stem cells. The expression vectors require that the pertinent sequence, i.e., those nucleic acids described elsewhere herein be operably linked to a promoter.

Expression vectors containing all the necessary elements for expression are commercially available and known to those skilled in the art (see, e.g., Sambrook et al., *Molecular Cloning: A Laboratory Manual*, Second Edition, Cold Spring Harbor Laboratory Press, 1989). Cells are genetically engineered by the introduction into the cells of heterologous DNA or RNA encoding the fusion protein reporter, or fragments, or variants thereof. The heterologous DNA or RNA is placed under operable control of transcriptional elements to permit the expression of the heterologous DNA in the host cell.

Fusion protein reporters of the presently disclosed subject matter can be can also be expressed recombinantly in a variety of prokaryotic and eukaryotic expression systems by constructing an expression vector appropriate to the expression system, introducing the expression vector into the expression system, and isolating the recombinantly expressed protein.

As used herein with respect to proteins, "isolated" means separated from its native environment and present in sufficient quantity to permit its identification or use. Isolated, when referring to a protein or polypeptide, means, for example: (i) selectively produced by expression of a recombinant nucleic acid or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure proteins may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, e.g., isolated from other proteins.

It will be understood by one of ordinary skill in the art that variants of the polypeptides that comprise the fusion protein reporter, or fluorophore carrying proteins, of the presently disclosed subject matter, and variations of the nucleic acids that encode these polypeptides, are also contemplated in some aspects of the presently disclosed subject matter. As used herein, the term "fusion protein reporter polypeptide" means a polypeptide sequence that forms part of the core of the fusion protein reporter. Variants of the polypeptides can include homologs. A homolog of a fusion protein reporter polypeptide is a polypeptide from a human or other animal that has a high degree of structural similarity to an identified fusion protein reporter polypeptide of the presently disclosed subject matter, e.g., at least about 75%, 80%, 85%, 90%, 95% or more amino acid sequence identity. Identification of human and other organism homologs of fusion protein reporter polypeptides will be familiar to those of skill in the art. In general, nucleic acid hybridization is a suitable method for identification of homologous sequences of another species (e.g., human, cow, sheep), that correspond to a known sequence. Standard nucleic acid hybridization procedures can be used to identify related nucleic acid sequences of selected percent identity. For example, one can construct a library of cDNAs reverse transcribed from the mRNA of a selected tissue and use the nucleic acids that encode fusion protein reporter polypeptides identified herein to screen the library for related nucleotide sequences. The screening preferably is performed using high-stringency conditions to identify those sequences that are closely related by sequence identity. Nucleic acids so identified can be translated into polypeptides and incorporated into fusion protein reporters which can be tested for functional ability to detect histone modification using the assay as described herein.

The terms "high stringency" and "highly stringent" as used herein refer to parameters with which the art is familiar. Nucleic acid hybridization parameters may be found in references that compile such methods (e.g. *Molecular Cloning: A Laboratory Manual*, J. Sambrook, et al., eds., Second Edition, Cold Spring Harbor Laboratory Press, Cold Spring Harbor, N.Y., 1989). More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM NaH$_2$PO$_4$ (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/ 0.1×SDS at temperatures up to 68° C.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids that encode fusion protein reporter polypeptides of the presently disclosed subject matter (e.g., by using lower stringency conditions). The skilled artisan also is familiar with the methodology for screening cells and libraries for expression of such molecules, which then are routinely isolated, followed by isolation of the pertinent nucleic acid molecule and sequencing.

In general, fusion protein reporter homologs and alleles typically will share at least 90% nucleotide identity and/or at least 95% amino acid identity to the sequences of fusion protein reporter polypeptides or fragments thereof, and precursors thereof, nucleic acid and polypeptides, respectively, in some instances will share at least 95% nucleotide identity and/or at least 97% amino acid identity, and in other instances will share at least 97% nucleotide identity and/or at least 99% amino acid identity. The homology can be calculated using various, publicly available software tools developed by NCBI (Bethesda, Md.) that can be obtained through the Internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group).

Identification of related sequences can also be achieved using conventional methods known to those of ordinary skill in the art, for example, the polymerase chain reaction (PCR) and other amplification techniques suitable for cloning related nucleic acid sequences. Preferably, PCR primers are selected to amplify portions of a nucleic acid sequence believed to be conserved (e.g., a binding domain, etc.). Again, nucleic acids are preferably amplified from a tissue-specific library.

The presently disclosed subject matter also includes degenerate nucleic acids that include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating fusion protein reporter polypeptide. Similarly, nucleotide sequence triplets which encode other amino acid residues include, but are not limited to: CCA, CCC, CCG, and CCT (proline codons); CGA, CGC, CGG, CGT, AGA, and AGG (arginine codons); ACA, ACC, ACG, and ACT (threonine codons); AAC and AAT (asparagine codons); and ATA, ATC, and ATT (isoleucine codons). Other amino acid residues may be encoded similarly by multiple nucleotide sequences. Thus, the presently disclosed subject matter embraces degenerate nucleic acids that differ from the biologically isolated nucleic acids in codon sequence due to the degeneracy of the genetic code.

The presently disclosed subject matter also provides modified nucleic acid molecules, which include additions, substitutions and deletions of one or more nucleotides (preferably 1-20 nucleotides) that are useful for practicing the presently disclosed subject matter. As used herein the terms: "deletion," "addition," and "substitution," mean deletion, addition, and substitution changes to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more nucleic acids of a sequence of the presently disclosed subject matter. In preferred embodiments, these modified nucleic acid molecules and/or the polypeptides they encode retain at least one activity or function of the unmodified nucleic acid molecule and/or the polypeptides disclosed herein, such as binding, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared. Each of these nucleic acid molecules can have one, two, or three nucleotide substitutions exclusive of nucleotide changes corresponding to the degeneracy of the genetic code as described herein. Likewise, modified nucleic acid molecules that encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the presently disclosed subject matter as readily envisioned by one of ordinary skill in the art. Any of the foregoing nucleic acids or polypeptides can be tested by routine experimentation for retention of structural relation or activity to the nucleic acids and/or polypeptides disclosed herein.

C. Introduction of Histone Reporter Allele Constructs into Cells and Animal Models Some embodiments of the presently disclosed subject matter also provide host cells transformed or transfected with the expression vector. Other embodiments of the presently disclosed subject matter provide a transgenic animal, particularly a non-human mammal, whose genome comprises an expression cassette encoding a fusion protein reporter of any of the foregoing embodiments.

A corresponding transgenic mouse model was created for each reporter allele; one to monitor global acetylation activity and one to monitor global H3K4 trimethylation activity. This was done by incorporating genetically encoded indicator alleles into epigenetic protected Rosa locus of mice (Hohenstein et al. (2008) *Pathogenetics* 3; 1(1):3) (see Examples below). As described above, the acetyl reporter protein quantifies the activity of the acetylation machinery (acetylation of H4 specifically at sites K5, K8, K12, and K16) and comprises an H4 tail (residues 1-30) on one end and a TATA binding protein (TBP)-associated factor II (TAFII) bromodomain on the other end (FIG. 18A). The TAFII bromodomain only recognizes and binds to the acetylated H4 tail. This acetylation-dependent reporter protein demonstrates a linear fluorescence response when quantified by fluorescence-activated cell sorting (FACS) in the presence of increasing amounts of suberoylanilide hydroxamic acid (SAHA), an HDACi, in culture systems (FIG. 18C, FIG. 18D, FIG. 19A, and FIG. 19B). For example, only 5% of cells were easily discriminated from auto fluorescence with 1 µM of SAHA, but increased to 20% with 2.5 µM of SAHA, 40% at 7.5 µM of SAHA and 45% at 10 µM of SAHA (FIG. 18D). Saturation of this response correlates well with immunoblot data using antibodies to the modified H4 tail (Munshi et al. (2006) *Mol. Cancer Ther.* 5:1967-74). This response is attenuated by co-transfection with a construct encoding a histone deacetylase (FIG. 20) and absent upon mutagenesis of all potential acetylation sites (FIG. 18E and FIG. 18I), attesting to its specificity.

The H3K4 trimethylation reporter allele encodes the H3 tail (residues 1-40) on one end and the TBP-associated factor III (TAF3) plant homeodomain (PHD) on the other end, which binds to trimethylated K4 on H3 (FIG. 18A). The H3K4 trimethylation reporter also demonstrates a dose response with increasing levels of the HDACi AR-42 (FIG. 18F), in keeping with prior work suggesting that AR-42 can also influence the methylation status of H3K4 through inhibition of demethylases (Huang et al. (2011) *Mol. Pharmacol.* 79:197-206). Activity is greatly attenuated upon mutagenesis of critical residues (M882A, W891A; Vermeulen et al. (2007) *Cell* 131, 58-69; van Ingen et al (2008) Structure 16, 1245-56) in the TAF3 reader domain (FIG. 18G) or with mutation of K4 (H3K4Q) in the H3 tail (FIG. 18G).

Both reporter alleles showed decreased activity when stably introduced into embryonic fibroblasts derived from Kmt2d$^{+/\beta Geo}$ mice, when compared to Kmt2d$^{+/+}$ littermates (FIG. 21). H3K4 trimethylation activity was enhanced upon treatment of Kmt2d$^{+/\beta Geo}$ cells with HDAC inhibitors AR-42 or MS275 (FIG. 18H, and FIG. 23C). An analysis of transfection efficacy in cells with both genotypes indicated comparable transfection efficacy (FIG. 22B).

Drawing blood from transformed mice during treatment and quantifying fluorescence in T cells using FACS provides a biomarker that can be used as therapeutic drug strategies are developed with epigenetically active agents. Alternatively, any other cells relevant to an investigator (e.g., neural cells) can be harvested for large scale chemical screening in vitro. Therefore, the presently disclosed fluorescence epigenetic system has definite advantages over previously developed FRET based systems which are not as applicable to incorporation into mice.

D. Methods of Using Histone Reporter Allele Constructs and Transformed Animal Models The histone reporter allele constructs of the presently disclosed subject matter, and transgenic animals whose genomes comprise an expression cassette encoding a fusion protein reporter of any of the foregoing embodiments, are useful in a variety of applications. In one aspect of the presently disclosed subject matter, a method for producing a cell specific screening assay for test agents, comprising: a) providing a transgenic animal whose genome comprises an expression cassette encoding a fusion protein reporter of any of the foregoing embodiments; b) crossing the transgenic animal with a compatible animal, wherein the compatible animal is an animal model of a disease, thereby producing a hybrid; c) isolating a disease relevant cell type from the hybrid; and d) utilizing the isolated disease relevant cell types in a high throughput screening assay for test agents. Cells may be isolated using conventional means known to those of skill in the art, including fluorometry or Fluorescence Assisted Cell Sorting (FACS). In one embodiment, different cell types may be compared, e.g., to establish whether mouse fibroblasts and/or lymphocytes might act as surrogates to what is occurring in disease relevant cells such as hippocampal neurons. These methods can also be used to screen mice (i.e., by FACS of cells derived from the mice) to identify additional chromatin candidate genes (modifiers) for N-ethyl N-nitrosourea (ENU) mutagenesis, as has been done for modifiers of the methylation machinery (Chong et al. (2007) *Nat. Genet.* 39:614-22).

Other uses for transgenic animals as disclosed herein include the measurement of biomarkers of in vivo efficiency as blood from animals undergoing a treatment regimen can be drawn intermittently and assayed with fluorescence quantified using FACS to quantify the effects of the treatment at that particular time point. Such methods are useful for developing a dosing regimen to titrate drugs to minimize the side effects or long term effects of epigenetic agents (e.g., a histone deacetylase inhibitor (HDACi).

Still other uses for transgenic animals as disclosed herein include methods to determine how global abnormalities in histone acetylation and/or H3K4 trimethylation lead to tissue specific problems frequently observed in both Rubinstein-Taybi and Kabuki syndromes through exploring tissue specific abnormalities in the fluorescence of the reporter at different stages in reporter animals using confocal microscopy. Similar approaches have been utilized with transgenic calcium reporter mice (Tallini et al. (2007) *Circ. Res.* 101:1300-9).

Accordingly, in one embodiment of the presently disclosed subject matter, methods of determining the level of histone modification are provided. The methods include contacting a biological sample with a fusion protein reporter of any of the foregoing embodiments, and monitoring the level of fluorescence in the biological sample as a measure of the level of histone modification in the biological sample. In some embodiments, the biological sample is a cell. In some embodiments, the cell is undergoing cell division. The methods also include incorporating an expression cassette encoding a fusion protein reporter of any of the foregoing embodiments into the genome of an animal, particularly a non-human mammal, and monitoring the level of fluorescence in living cells of the animal as a measure of the level of histone modification in the living cells.

In another embodiment of the presently disclosed subject matter, methods of diagnosing a histone-modification disorder in a subject are provided. The methods include contacting a biological sample from a subject with a fusion protein reporter of any of the foregoing embodiments, monitoring the level of fluorescence in the biological sample, comparing the level of fluorescence in the sample to a control level of fluorescence as a determination of a histone modification disorder in the subject. In some embodiments, the biological sample is selected from the group consisting of tissue and cells, particularly living cells.

In yet another embodiment of the presently disclosed subject matter, methods of monitoring the onset, progression, or regression of a histone-modification disorder in a subject are provided. The methods include contacting a first biological sample from a subject with a fusion protein reporter of any of the foregoing embodiments determining the level of fluorescence in the first biological sample, contacting a subsequent second biological sample from the subject with a fusion protein reporter of any of the foregoing embodiments, determining the level of fluorescence in the second biological sample, comparing the level of fluorescence in the first biological sample to the level of fluorescence in the second biological sample as a measure of the onset, regression or progression of a histone modification disorder in the subject. In some embodiments, the biological sample is selected from the group consisting of tissue and cells, particularly living cells.

In some embodiments, the method of monitoring the onset, progression or regression of a histone-modification disorder in a subject also includes administering after the first biological sample is obtained from the subject and before the second biological sample is obtained from the subject a candidate pharmacological agent to the subject, wherein the measure of the onset regression or progression of a histone modification disorder in the subject is an indication of the effect of the candidate pharmacological agent on histone modification in the subject. In some embodiments, the biological sample is selected from the group consisting of tissue and cells, particularly living cells.

In another embodiment of the presently disclosed subject matter, methods for evaluating the effect of a candidate pharmacological agent on histone modifications in a subject are provided. The methods include contacting a biological sample from the subject with a fusion protein reporter of any of the foregoing embodiments contacting the biological sample with a candidate pharmacological agent, monitoring the level of fluorescence in the biological sample, comparing the level of fluorescence in the biological sample to the level of fluorescence in a control biological sample contacted with the fusion protein reporter and not contacted with the candidate pharmacological agent, wherein a relative increase or relative decrease in the level of fluorescence indicates an effect of the candidate pharmacological agent on histone modification in the subject. In some embodiments, the biological sample is selected from the group consisting of tissue and cells, particularly living cells.

A "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments).

As used herein, the phrase "biological sample" encompasses a variety of sample types obtained from a subject and useful in the procedure of the presently disclosed subject matter. In one embodiment of the presently disclosed subject matter, the biological sample comprises whole blood, hemocytes, serum, or plasma. However, biological samples may include, but are not limited to, solid tissue samples, liquid tissue samples, biological fluids, aspirates, cells and cell fragments. Specific examples of biological samples include, but are not limited to, solid tissue samples obtained by surgical removal, pathology specimens, archived samples, or biopsy specimens, tissue cultures or cells derived therefrom and the progeny thereof, and sections or smears prepared from any of these sources. Non-limiting examples of biological samples include samples obtained from breast tissue, lymph nodes, and breast tumors. Biological samples also include any material derived from the body of a vertebrate animal, including, but not limited to, blood, cerebrospinal fluid, serum, plasma, urine, nipple aspirate, fine needle aspirate, tissue lavage such as ductal lavage, saliva, sputum, ascites fluid, liver, kidney, breast, bone, bone marrow, testes, brain, ovary, skin, lung, prostate, thyroid, pancreas, cervix, stomach, intestine, colorectal, brain, bladder, colon, nares, uterine, semen, lymph, vaginal pool, synovial fluid, spinal fluid, head and neck, nasopharynx tumors, amniotic fluid, breast milk, pulmonary sputum or surfactant, urine, fecal matter and other liquid samples of biologic origin.

As used herein, the terms "increase," "decrease," and "difference" preferably mean significant increase, decrease, and difference respectively, e.g. statistically significant.

It will be understood by one of ordinary skill in the art that some disorders will exhibit an increase in histone modifications relative to those in normal cells and tissues and other disorders will exhibit a decrease in histone modifications relative to those in normal cells. Because the fusion protein reporter of the claimed presently disclosed subject matter can detect either an increase or decrease in the level of histone modification in cells and tissues it can be used to determining the existence of either category of disorder.

There may be reduced levels of histone modification in cells and tissues in some disorders. In these cells and tissues, a determination of the level of histone modification is diagnostic of a protein-modification-associated disorder if the level of protein modification is below a baseline level determined for that tissue or cell type. The baseline level of protein modification can be determined using controls known to those of skill in the art. Such methods include, for example, assaying a number of histologically normal tissue samples from subjects that are clinically normal (i.e., do not have clinical signs of a protein-modification-associated disorder in the tissue type) and determining the mean level of protein modification for the samples. This baseline level can then be compared to the level protein modification in other samples and cells and can serve as a control baseline level for diagnostic comparisons.

The determination that the level of histone modification is above a baseline level determined for that tissue or cell type, alternatively, may indicate the presence of a protein-modification-associated disorder, e.g. a histone-modification-associated disorder, in the cell or tissue.

Thus, in some cells and tissues there is a baseline level of protein modification that can be assessed using the fusion protein reporter of the presently disclosed subject matter, and it is that baseline/control level that determines the level below which a level of protein modification indicates a protein-modification-associated disorder in the tissue. Therefore, in these disorders, the level of protein modification indicates a protein-modification-associated disorder in the tissue when the level of protein modification is less than about 95% of that in a control tissue sample. A level of protein modification of less than about 99%, 95%, 90%, 80%, 70%, 60%, 50%, 40%, 30%, 20%, 10%, 5%, or less of the level of protein modification in the control tissue indicates a protein-modification-associated disorder in the tissue. Thus, a level of histone modification of less than about 99%, 95%, 90%, 80%, 70%, 60%, 50%, 40%, 30%, 20%, 10%, 5%, or less of the level of histone modification in the control tissue indicates a histone-modification-associated disorder in the tissue.

A baseline level of histone modification can also be used in the assessment of disorders that are associated with an increase in protein modification. In such disorders, an increase in the level of protein modification in a sample cell, relative to the baseline/control level, indicates the presence of the disorder in the cell. In these disorders, the level of protein modification indicates a protein-modification-associated disorder in the tissue when the level of protein modification is more than about 105% of that in a control tissue sample. A level of protein modification of more than about 110%, 115%, 120%, 125%, 130%, 135%, 140%, 150, 160% 170% or more than the level of protein modification in the control tissue indicates a protein-modification-associated disorder in the tissue. Thus, a level of histone modification of more than about 110%, 115%, 120%, 125%, 130%, 135%, 140%, 150, 160% 170% or more than the level of histone modification in the control tissue indicates a histone-modification-associated disorder in the tissue.

As used herein the term "control" means predetermined values, and also means baseline controls. Examples include samples from control populations or control samples generated through manufacture to baseline controls for experimental samples.

As used herein the term "control" includes positive and negative controls which may be a predetermined value that can take a variety of forms. The control(s) can be a single cut-off value, such as a median or mean, or can be established based upon comparative groups, such as in groups having normal levels of histone modification in cells and tissues and groups having abnormal levels of histone modification in cells and tissues. Another example of a comparative group is a group having a particular disease, condition and/or symptoms and a group without the disease, condition and/or symptoms. Another comparative group is a group with a family history of a particular disease and a group without such a family history of the particular disease. The predetermined control value can be arranged, for example, where a tested population is divided equally (or unequally) into groups, such as a low-risk group, a medium-risk group and a high-risk group or into quadrants or quintiles, the lowest quadrant or quintile being individuals with the lowest risk or highest histone modification levels in a disorder indicated by decreased histone modification. Similarly, the highest quadrant or quintile being individuals with the highest risk or lowest histone modification levels in a disorder indicated by decreased histone modification. It will be understood that in a disorder characterized by increased protein (e.g histone) modification, the lowest quadrant or quintile will include individuals with the lowest risk or lowest histone modification levels and the highest quadrant or quintile will include individuals with the highest risk or highest histone modification levels.

The predetermined value of a control will depend upon the particular population selected. For example, an apparently healthy population (or cells or subjects) will have a different "normal" histone modification level range than will a population which is known to have a condition characterized by aberrant levels of histone modification. Accordingly, the predetermined value selected may take into account the category in which an individual falls. Appropriate ranges and categories can be selected with no more than routine experimentation by those of ordinary skill in the art. Typically the control will be based on apparently healthy individuals in an appropriate age bracket. By "decrease" it is meant less histone modification relative to a selected control. By "increase" it is meant more histone modification relative to a selected control.

The presently disclosed subject matter also includes methods to monitor the onset, progression, or regression of protein-modification-associated disorders in a subject by, for example, obtaining cell or tissue samples at sequential times from a subject and assaying such samples for the level of protein modification using the fusion protein reporter of the presently disclosed subject matter. A subject may be suspected of having a protein-modification-associated disorder or may be believed not to have a protein-modification-associated disorder and the sample can serve as a baseline level for comparison with subsequent cell or tissue samples from the subject.

Onset of a condition is the initiation of the physiological changes or characteristics associated with the condition in a subject. Such changes may be evidenced by physiological symptoms, or may be clinically asymptomatic. For example, the onset of a histone-modification-associated disorder may be followed by a period during which there may be protein-modification-associated disorder physiological characteristics in the subject, even though clinical symptoms may not be evident at that time. The progression of a condition follows onset and is the advancement of the physiological characteristics of the condition, which may or may not be marked by an increase in clinical symptoms. In contrast, the regression of a condition is a decrease in physiological characteristics of the condition, perhaps with a parallel reduction in symptoms, and may result from a treatment or may be a natural reversal in the condition.

The level of protein-modification in a cell or tissue sample from a subject that is determined to be at a level below (or in some disorders a level above) the baseline level for that protein modification, is an indicator for a protein-modification-associated disorder in the subject. For example, in a type of a histone-modification-associated disorder in which a level of histone modification is known to be decreased, the determination that the level of the histone modification in a cell or tissue sample is below the level in a normal control tissue, would be diagnostic for the histone-modification-associated disorder. A similar method can be used to determine the presence of a histone-modification-associated disorder in which an increase in the level of histone modification is indicative of the disorder. The level of histone modification may be determined by measuring the fluorescence level following contacting the cell with the fusion protein reporter of the presently disclosed subject matter.

The onset of a protein-modification-associated disorder may be indicated by the increase or decrease in the level of histone modification in a sample from a subject as compared to the level of protein modification determined in a previous sample from the subject. Thus, if the level of histone modification is determined to be lower or higher in a second sample from a subject when compared to the level determined in a first sample from a subject, this is an indication of the onset of a histone-modification-associated disorder in the subject.

Progression and regression of a protein modification-associated disorder may be indicated by the alteration of the level of protein modification a subject's samples over time. An example of which, though not intending to be limiting is that in disorders characterized by decreased levels of histone modification, progression of a histone-modification-associated disorder is indicated when there is a decrease in the level of histone modification in cells obtained from a subject as compared to the level in cells previously obtained from the same subject. Similarly, regression of such histone-modification-associated disorders may be indicated when there is determined to be an increase in the level of histone modification in cells obtained from a subject as compared to the level in cells previously obtained from the same subject. The methods and reporters of the presently disclosed subject matter are also useful for assessing progression and/or regression in other protein modification-associated disorders.

One of ordinary skill in the art will recognize that for a disorder characterized by an increase in protein modification, progression of the disorder may be indicated when there is a statistical increase in the level of protein modification in a cell sample, relative to the level of the protein modification determined in a previous cell sample. Similarly, regression of such a protein-modification-associated disorder may be indicated when the level of protein modification determined in cells obtained from a subject, is statistically less than the level determined in cells previously obtained from the subject.

E. Kits

The presently disclosed subject matter also includes kits that include the fusion protein reporter of the presently disclosed subject matter. An example of a kit of the presently disclosed subject matter is a kit that provides components necessary to determine the level of histone modification in a cell or tissue sample. Components in such kits may include a fusion protein reporter of the presently disclosed subject matter and instructions for its use to assess histone modification levels. The kits of the presently disclosed subject matter can include instructions or other printed material on how to use the various components of the kits for diagnostic purposes. Additional materials may be included in any or all kits of the presently disclosed subject matter, and such materials may include, but are not limited to buffers, water, enzymes, tubes, control molecules, etc.

In some embodiments, chromatin immunoprecipitation of a mark defective in a particular disorder (e.g., H3K4me3 for KS and H4Ac for RTS) followed by some form of quantification (e.g., real time PCR, microarrays, or next generation sequencing) can be used a diagnostic tool or a measurement of therapeutic efficiency.

Recent advances in Chromatin Immunoprecipitation-Sequencing (ChIP-seq) technologies (Brind'Amour et al. (2015) *Nat Commun.* 21; 6:6033; Gilfillan G D et al. (2012) *BMC Genomics* November 21; 13:645) and related techniques, such as ATAC-seq (Buenrostro et al. (2015) *Curr Protoc Mol Biol.* 109:21.29.1-21.29.9), have been performed on cell numbers that can be practical to extract from patients (500-10,000 cells) with a simple blood draw. Accordingly, regarding the Mendelian disorders of the epigenetic machinery, chromatin immunoprecipitation of a mark defective in a particular disorder (e.g., H3K4me3 for KS and H4Ac for RTS) followed by some form of quantification (e.g., real time PCR, microarrays, or next generation sequencing) can be used as a diagnostic tool or a measurement of therapeutic efficiency. Examples include, but are not limited to, quantifying global levels of H3K4me3 in Kabuki syndrome (expected to be decreased), H3K27me3 in Kabuki syndrome (expected to be increased) and Weaver syndrome (expected to be decreased), and histone acetylation in Rubinstein-Taybi syndrome (expected to be decreased) and Brachydactyly-Mental Retardation (expected to be increased).

In some embodiments, the presently disclosed subject matter provides a kit for diagnosing and/or monitoring treatment efficacy of a histone-modification disorder, comprising a container containing a fusion protein reporter fusion protein reporter described herein and instructions for the use of the fusion protein reporter in the diagnosis and/or monitoring treatment efficacy of a histone-modification disorder. In some embodiments, the kit comprises reagents and/or instructions for chromatin immunoprecipitation (ChIP). In some embodiments, the kit comprises reagents and/or instructions for chromatin immunoprecipitation-sequencing (ChIP-seq).

As used herein, the term "ChIP" refers to a type of immunoprecipitation technique that can be used to determine the specific locations in the genome associated with various histone modifications. In native ChIP, native (not cross-linked) chromatin is sheared by nuclease digestion and the remaining histone-DNA complexes are immunoprecipitated. The complex-associated DNA can then be analyzed and quantified using such methods as PCR or DNA sequencing, for example. As used herein, the term "ChIP-sequencing" refers to a method that combines chromatin immunoprecipitation with DNA sequencing to identify the binding sites of DNA-associated proteins, such as histones.

II. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Materials and Methods
 Study Design:
 The purpose of this study was to explore the pathophysiological sequence in KS, a Mendelian disorder of the epigenetic machinery, and to seek robust disease associated phenotypes, which could be used to monitor therapeutic response. It was hypothesized that since both causes of KS involve the transition from closed to open chromatin, this disorder might be caused by a general imbalance between open and closed chromatin states (favoring closed chromatin) and this ongoing deficiency might be ameliorated with agents that favor chromatin opening such as HDACi. At least 3-4 biological replicates were used for each biochemical analysis, while a sample size of at least 8-10 per group was used for behavioral testing. Data collection occurred for a pre-determined and of consistent duration, as dictated by literature-based or core facility-based standards and no exclusion criteria were applied. All analyses were performed by examiners blinded to genotype and/or treatment arm. For drug treatments, animals were randomly assigned to treatment arms with approximately equivalent numbers in each group. Box and whisker plots identify RStudio-defined outliers (shown as circles), but all data points were used in statistical analyses.
 Design of the Indicator Constructs.
 A genetically encoded histone reporter allele system has been developed which can be used to monitor activity of any histone maintenance machinery component in live cells. Previously, FRET based epigenetic activity systems have been created (Lin and Ting (2004) *Angew Chem Int Ed Engl.* 24; 43 (22):2940-3; Lin et al. (2004) *J. Am. Chem. Soc.* 19; 126(19):5982-3; U.S. Pat. No. 7,056,683). However, FRET-based assays need a complex technological setup which is not widely available and FRET-based assays have been much more difficult to introduce into transgenic mouse models. Here, the presently disclosed non-FRET-based histone indicator system is demonstrated through examples of two well understood histone modifications, histone acetylation and histone H3K4 trimethylation. The particular construct design is based on a circularly permutated green fluorescent protein (GFP) that lacks fluorescence unless the two parts of GFP are brought into close proximity by external forces (Baird et al. (1999) *Proc. Natl. Acad. Sci. U.S.A.* 28; 96(20):11241-6). The constructs are targeted to the nucleus through a nuclear localization signal (NLS). Mutants were also created that knocked out the activity of the indicator allele.

The acetyl reporter protein quantifies the activity of the acetylation machinery (acetylation of H4 specifically at the 5th, 8th, 12th and 16th Lysine's) and comprises an H4 tail on one end (the target for acetylation) and a TBP associated factor II (TAFII) bromodomain on the other end of the reporter protein (FIG. 5A). The TAFII bromodomain only recognizes and binds to the acetylated H4 tail, resulting in reconstitution of GFP structure and function (i.e. fluorescence). Therefore, the reporter protein has no fluorescence unless it is acetylated by the acetylation system of the nucleus of the cell.

An H3K4 trimethylation reporter was also created (FIG. 5B). This reporter is based on the H3 tail on one end and the TBP associated factor III (TAFIII) homeodomain on the other end; the TAFIII homeodomain only identifies and binds to trimethylated K4 on H3. When the H3K4 site gets trimethylated, the TAFIII homeodomain can bind to the modified H3 tail and bring the two parts of the separated GFP in close proximity. The activity of the epigenetic modification system can be quantified through fluorescence.
 Epigenetic Reporter Alleles:
 Epigenetic reporter alleles were synthesized (OriGene, Rockville, Md.) using published sequences for component elements (Baird et al. (1999) *Proc. Natl. Acad. Sci.* 96:11241-6; Souslova et al. (2007) *BMC Biotechnol.* 7:37). Single nucleotide mutations were created using the Quick-Change Lightening kit (Agilent Technologies Inc, Santa Clara, Calif.). For H4ac indicator, K5R, K8R, K12R, K16R and K20R (MUT indicator) were introduced. For H3K4me3 indicator, K4Q and D890A/W891A and M882A (three separate constructs) were introduced. For transient transfections, mouse embryonic fibroblasts (see below) were transfected with Fugene HD (Promega, Madison, Wis.), 48 hours prior to FACS. Transfection efficiency of reporter alleles was comparable in transiently-transfected murine embryonic fibroblasts (MEFs) derived from mice of both genotypes (Kmt2d$^{+/\beta Geo}$ and Kmt2d$^{+/+}$), as measured by real-time PCR of genomic DNA. For drug stimulation, drug was added to the media 24 hours prior to FACS. For stable transfections in T293 (American Type Culture Collection) cells, 10 µg/ml of Blastocidin (Life Technologies, Carlsbad, Calif.) was added to the media for several weeks. For stable transfection in MEFs, the reporter was transferred to a ViraPower Lentiviral Expression System (Life Technologies, Carlsbad, Calif.). After selection with Blastocidin, the drug of interest was added 24 hours prior to FACS. SAHA, AR-42 and MS275 were purchased from Selleck (Selleck Chemicals, Houston, Tex.). FACS was performed using either a FAC-SCalibur (BD Biosciences, San Jose, Calif.) or FACSverse (BD Biosciences, San Jose, Calif.) system with comparable results. FACS data were analyzed using FlowJo (Tree Star Inc, Ashland, Oreg.). A plasmid expressing HDAC3 was acquired from Addgene (Cambridge, Mass., plasmid 13819) and transfected into a stable cell line carrying the H4 acetyl reporter allele.

Animals:

Kmt2d$^{+/\beta Geo}$ mice, also named Mll2Gt$^{(RRt024)Byg}$, were acquired from Bay Genomics (University of California). All experimental mice were on a mixed C57BL/6J and 129/SvEv background. Expected Mendelian ratios were observed when heterozygous animals were bred to wild-type. In heterozygous crosses, however, there was uniform embryonic lethality of homozygotes by ED12, the earliest developmental stage assayed. For treatment with AR-42, mice were orally gavaged daily with drug (Selleck Chemicals, Houston, Tex.) solubilized in vehicle (0.5% methylcellulose, 0.1% Tween-80, water) or with vehicle alone. Drug delivery information was kindly provided by Drs. Chen and Kulp from Ohio State University (Huang et al. (2011) *Mol. Pharmacol.* 79:197-20619). Drug was administered for 14 days and mice were sacrificed on day 15. Morris water maze testing was initiated at day 7 and a dose of 10 mg/kg/day was used for these studies. For quantification of DCX positive cells, doses of 0, 5, 10 and 25 mg/kg/day were used. Genotyping was performed using primers B-GeoF-(CAAATGGCGATTACCGTTGA; SEQ ID NO: 1) and B-GeoR-(TGCCCAGTCATAGCCGAATA; SEQ ID NO: 2) that are specific for the targeted allele and TcrdF-(CAAAT-GTTGCTTGTCTGGTG; SEQ ID NO: 3) and TcrdR-(GTCAGTCGAGTGCACAGTTT; SEQ ID NO: 4) that control for sufficient DNA concentration. Real-time PCR using the same primers allows discrimination between the heterozygous and homozygous state for the targeted allele. Maxillary protrusion was evaluated by ten investigators blinded to genotype and they were asked to rate maxillary protrusion on radiographs as either large (2) or small (1). When results were unblinded and average scores for each animal determined, the Kmt2d$^{+/\beta Geo}$ animals had a significantly lower score than Kmt2d$^{+/+}$ littermates. All experiments were performed using mouse protocols approved by the Animal Care and Committee of Johns Hopkins University School of Medicine. The mouse protocols used for this study are in accordance with the guidelines used by the NIH for mouse care and handling.

Perfusion and Cryosectioning:

Mice were sacrificed with a xylazine ketamine combination, transcardially flushed with PBS/Heparin and then perfused with 4% PFA/PBS. Brains were dissected and cryopreserved in 30% sucrose 0.1M phosphate solution overnight at 4° C. Brains were frozen and sectioned using a Microm HM 550 cryostat (Thermo Scientific, Waltham, Mass.). Sectioning was performed at 30 µm intervals and every section of the brain was collected and stored in glycerine ethelyne glycol phosphate storage solution.

EdU Administration and Staining:

For EdU experiments, mice were injected IP over ten days, with injections on the first three and last three days, with 50 mg/kg EdU (Life Technologies, Carlsbad, Calif.). Mice were sacrificed 30 days after the initial start of injection, and EdU staining was done with the Click-iT EdU Alexa Fluor 488 Imaging Kit (Life Technologies, Carlsbad, Calif.) as well as DAPI mounting with Vectamount (Vector Laboratories, Burlingame, Calif.). EdU quantification was performed by an individual blinded to genotype. Positive cells were counted in every sixth slice in the GCL and the average number per slice was calculated for each brain.

Real Time PCR:

Real-time PCR was performed using Kmt2d-specific probes for exons 20 and 52 (Mm_02600438 and Mm_01717664, respectively) from TaqMan® Gene Expression Assays (Life Technologies, Carlsbad, Calif.). For a comparison of transfection efficiencies for indicator constructs in transient transfection studies, real-time PCR was performed using SYBR Green Real-Time PCR Master Mix (Life Technologies, Carlsbad, Calif.) and primers IND-F-(CTGCGCGCAAGTCAACGGGTG; SEQ ID NO: 5) and IND-R-(ATGCCGTTCTTCTGCTTGTCG; SEQ ID NO: 6) that are specific for the H3K4 methylation indicator. For expression analysis for KMT2D target gene KLF10, real-time PCR was performed using Klf10-specific expression assay (Mm00449812_m1) from TaqMan® Gene Expression Assays (Life Technologies, Carlsbad, Calif.).

Immunoblotting:

Total protein lysates from Kmt2d$^{+/\beta Geo}$ and Kmt2d$^{+/+}$ littermates were isolated and immunoprecipitated with an antibody against the amino terminus of KMT2D (sc-292359, Santa Cruz Biotechnology, Dallas, Tex.). Isolated protein was applied to a membrane and immunoblotted with an antibody against beta-galactosidase (ab9361, Abcam, Cambridge, ENG) as previously described (Loeys et al. (2010) *Sci. Transl. Med.* 23: 23ra20).

Immunofluorescence:

Every 6$^{th}$ brain section was selected and then blocked with 5% Bovine Serum Albumin (BSA) at room temperature followed by incubation with primary antibodies overnight at 4° C. Secondary antibodies were then applied for 1 hour at room temperature, after which sections were mounted onto microscope slides with Vectamount with DAPI (Vector Laboratories, Burlingame, Calif.). Primary antibodies included Doublecortin (DCX) (SC-8066, Santa Cruz Biotechnology, Dallas, Tex., 1:200 goat), trimethylated H3K4 (9727L, Cell Signaling Technology, Beverly, Mass., 1:500 rabbit), and Kmt2d H-300 (SC-292359, Santa Cruz Biotechnology, Dallas, Tex., 1:500 rabbit). Non-specific binding was not observed when sections were sequentially exposed to serum (or IgG when appropriate) from the same species as the primary antibody for each experiment (i.e. rabbit for KMT2D and H3K4me3 and goat for doublecortin), followed by the secondary antibody used for KMT2D and H3K4me3 (anti-rabbit) or doublecortin (anti-goat, FIG. 29).

Confocal Microscopy:

Z-stack images of slides were taken at either 10× using Zeiss Axiovert 200 with 510-Meta confocal module (Carl Zeiss, Jena, GER) or 25× using Zeiss AxioExaminer with 710NLO-Meta multiphoton (Carl Zeiss, Jena, GER). From 10× pictures, the GCL was highlighted and fluorescent intensities for both DAPI and H3K4me3 were measured at the midpoint of the entire z-stack (Zen software, Carl Zeiss, Jena, GER) with the value for Kmt2d$^{+/+}$ animals set equal to one. A Students t-test with significance value set at P<0.05 was used to compare H3K4 trimethylation intensity referenced to DAPI intensity.

GCL and Doublecortin Area:

The area of both the GCL and DCX+ cells was measured using the NS elements 2.0 software (Nikon, Tokyo, JPN). Normalized DCX area was calculated by measuring the DCX+ area of the GCL and setting the baseline (Kmt2d$^{+/+}$) fraction to 1. A Student t-test with significance value set at P<0.05 was used for comparison of DCX+ area referenced to GCL area between genotypes and treatment arms.

Behavioral Testing:

Mice ranged from two to three months of age in all tests, and all experiments were performed in the late morning or early afternoon.

Novel Object Recognition:

On the first day of the novel object recognition test, mice were individually placed into a square plastic arena (25 cm×25 cm×25 cm) that contained two identical plastic objects along the midline of the arena. Each mouse was allowed to explore the objects for 10 minutes and then placed back in its home cage. The following day, each mouse was placed in the same arena with the same two identical objects and the time interacting with each object was recorded over 10 minutes. On the third day, one object was removed and was replaced by a novel object. Mice were placed in the arena for five minutes and timed for interaction with the familiar object compared to the novel object. Interactions with objects were recorded and measured in a way that was blinded to both genotype and drug treatment. Differences in interaction time between the novel object and the familiar object for Kmt2d$^{+/+}$ and Kmt2d$^{+/\beta Geo}$ mice were calculated by computing time spent with the novel object divided by the total time spent with both objects. These values were analyzed for significance with a Student's t-test with significance value set at $P<0.05$.

Morris Water Maze:

Mice were placed in a 1.1 meter diameter tank filled with room temperature water dyed with non-toxic white paint. For analysis purposes, the tank was divided into four quadrants, with one quadrant containing a small platform submerged 1.5 cm beneath the water. On each day of training, mice were placed in the tank in a random quadrant facing away from the center and were allowed to swim until they found the platform and were left there for 30 seconds. If they did not reach the platform after 60s they were placed on it for 30 seconds. Each mouse was given 4 trials per day (for 5 days) with no inter-trial interval and subsequently returned to its home cage. Latency to reach the platform was measured during each trial. The day after the final day of training, the platform was removed for a probe trial where mice were placed in the tank for 90s. Average number of crossings of the platform's previous location was recorded. Visible/flagged platform training was also performed for 3 days either before the hidden platform or after the probe trial, where a visible flag was placed on the submerged platform, and the time for each mouse to reach the platform was measured for each 60 second trial, four of which were run in the same way as the hidden platform training. For all training and probe testing, data was recorded both manually and electronically with ANY-maze software (San Diego Instruments, San Diego, Calif.) when applicable. All data were collected and analyzed by an individual blinded to genotype and treatment group. Differences in the number of platform crossings during the probe trial were compared between groups with a Student's t-test with significance value set at $P<0.05$.

Fear Conditioning Testing:

On day 1, both Kmt2d$^{+/\beta Geo}$ mice and Kmt2d$^{+/+}$ littermates were placed in chamber and allowed to explore the chamber freely. After 120 seconds (2 minutes), a 2000 Hz sound was played for 30 seconds. For the last 2 seconds of sound (seconds 148-150), the sound co-occurred with a 0.35 mAmp electrical shock (2 seconds) administered through the floor grid. Mice were observed for a total of 300 seconds. Freezing behavior was measured using the FreezeScan software (CleverSys Inc, Reston, Va.). On days 2 and 14 (FIG. 9), contextual freezing was assessed over 300 seconds (no cue). On days 3 and 15, cued freezing was assessed over 300 seconds.

Open Field Testing:

Mice were placed in the open field chamber and activity was monitored using the Photobeam activity system (San Diego Instruments, San Diego, Calif.). Activity levels (ten 180 second intervals) were pooled to yield a general activity level (Adamczyk et al. (2012) Behav Brain Res. 229: 265-72).

Grip Strength Testing:

Grip strength testing was performed as previously described (Adamczyk et al. (2012) Behav Brain Res. 229: 265-72). Three trials were performed and averaged for each mouse.

Retrospective Analysis of Neuropsychological Testing on Patients with Kabuki Syndrome:

A retrospective chart review was performed using data from patients that had clinically indicated neuropsychological testing at the Kennedy Krieger Institute in years 2004-2014. Test results were analyzed from the three individuals with most extensive testing available and a known disease associated mutation in KMT2D. All patient data was collected after consenting patients and stored in secure electronic database at KKI. For this particular analysis per Kennedy Krieger and Johns Hopkins organizational policy, additional IRB review was not required (three or fewer patients). The individual tasks were divided into 16 categories, and literature was used to identify tasks known to be associated with dentate gyrus (Kesner (2013) Behav. Brain Res. 254:1-7; Morris et al. (2012) Neurobiol. Learn. Mem. 97:326-31; Epp et al., (2011) Neurobiol. Learn. Mem. 95:316-25) or hippocampus (non-dentate gyrus).

ChIP-seq:

Spleens were dissected from eight mice, four from each kmt2d genotype (+/βGeo or +/+) where half of each genotype was treated with AR-42 and half with vehicle only. Spleens were minced and passed through a 40 μm cell strainer to obtain single cell suspensions. 10 million cells were used for each ChIP-seq experiment following the native chromatin immunoprecipitation protocol, as previously described (Gilfillan et al. (2012) BMC Genomics 13:645), using a ChIP-grade antibody against H3K4me3 (9727, Cell Signaling Technology, Beverly, Mass.).

ChIP-seq Data Analysis:

Sequencing was performed using a MiSeq system (Illumina, San Diego, Calif.). 4.8-9.6 million paired-end 26 bp reads were obtained per sample (Table 1; nReads=number of reads, alignRate=fraction aligned to genome; FRIP=fraction of reads in peaks). Reads were aligned to the m. musculus genome, version mm10, using Bowtie 2 (Langmead and Salzberg (2012) Nat. Methods. 9: 357-9). Each sample was examined with regard to alignment rate as well as FRIP (fraction of reads in peaks), a measure of the ChIP efficiency (Table 1). FRIP was computed based on peaks called only on specific samples using MACS version 1.4.2 (Zhang et al. (2008) Genome Biol. 9: R137). For analysis, reads were merged into one meta-sample and peak calling was performed using MACS version 1.4.2 (Zhang et al. (2008) Genome Biol. 9: R137). This allowed definition of a superset of 33,517 peaks in one or more samples. The number of reads overlapping a peak was computed using bedtools version 2.17.0 (Quinlan and Hall (2010) Bioinformatics 26:841-2) in the following way: each paired-end read was converted to a single interval containing both mate coordinates (effectively filling in the insert) and these intervals were examined for overlaps with the superset of peaks. This created a peak by sample matrix of read counts. Differential binding was assessed using the GLM functionality (McCarthy et al. (2012) *Nucleic Acids Res.* 40:4288-97) in edgeR version 3.5.27 (Robinson et al. (2010) *Bioinformatics.* 26:139-40). A single model was fit, using all 8 samples, with Tagwise variance estimation. Different contrasts were examined corresponding to the different hypotheses considered in the main text, and peaks were considered differentially bound if they had a Benjamini-Horchberg corrected p-value less than 5%. Fold change and overall abundance was calculated as per edgeR.

For FIG. 6D, FIG. 25E, FIG. 27A, FIG. 27B, FIG. 27C, FIG. 27D, and FIG. 27E, each point corresponds to a genomic location with an H3K4me3 peak in at least one of the samples. A positive value indicates that the peak is higher in the Kmt2d$^{+/\beta Geo}$ compared to the Kmt2d$^{+/+}$. Peaks which are significantly differentially bound are shown in red, and other peaks are shown in gray. In FIG. 27A, FIG. 27B, FIG. 27C, FIG. 27D, and FIG. 27E, the expected medium is demonstrated with a broken line, but unbroken line shows the median in the observed comparison. FIG. 28A, FIG. 28B, FIG. 28C, FIG. 28D and FIG. 28E illustrate whether the balance is shifting up (blue) or down in a particular comparison. To examine whether there was a directional balance between differentially bound genes, the following test was developed. For Kmt2d$^{+/+}$ (vehicle) compared to Kmt2d$^{+/\beta Geo}$ (vehicle), 454 peaks are observed to be stronger bound in the mutant, 1,499 to be stronger bound in the wild-type and 27,052 peaks to not be differentially bound. The model assumes that these three numbers follow a multinomial distribution with a probability vector (p1, p2, p3). To test for directional balance, a standard likelihood-ratio test for the hypothesis p1=p2 is constructed. Per standard results, two times the negative log-likelihood ratio test statistic is asymptotically chi-square distributed with 1 degree of freedom.

TABLE 1

A summary of genotypes, drugs and quality measures of ChIP-seq experiments.

| Genotype | Drug | Run | nReads | alignRate | FRIP |
|---|---|---|---|---|---|
| Kmt2d$^{+/\beta Geo}$ | AR-42 | run4 | 5690117 | 0.92 | 0.508 |
| Kmt2d$^{+/\beta Geo}$ | Vehicle | run4 | 7520215 | 0.93 | 0.556 |
| Kmt2d$^{+/+}$ | AR-42 | run4 | 9614420 | 0.92 | 0.48 |
| Kmt2d$^{+/+}$ | Vehicle | run4 | 6828962 | 0.92 | 0.571 |
| Kmt2d$^{+/\beta Geo}$ | AR-42 | run5 | 7604137 | 0.93 | 0.53 |
| Kmt2d$^{+/\beta Geo}$ | Vehicle | run5 | 6016687 | 0.92 | 0.55 |
| Kmt2d$^{+/+}$ | AR-42 | run5 | 4846490 | 0.93 | 0.545 |
| Kmt2d$^{+/+}$ | Vehicle | run5 | 8682723 | 0.93 | 0.573 |

Statistics and Plots:

For all box plots generated through RStudio (RStudio Inc, Boston, Mass.), the margins of the box show the upper and lower quartiles, the central line shows the median, and the whiskers show the range. Circles denote outliers as defined by the RStudio algorithm. For all column, line, and scatter-plot graphs (generated through Microsoft Excel), the error bars represent standard error of the mean, with the data point representing the mean of each applicable group. Unless otherwise stated, significance between two groups was calculated with a Student's t-test with a significance value of P<0.05. Two-way repeated measures ANOVAs were calculated with SPSS (IBM, Armonk, N.Y.). For every calculated P value the stated n represents the number of animals for each group contributing to that comparison. For P value nomenclature, *=P<0.05, **=P<0.01, †=P<0.005, ††=P<0.001.

Results

Kmt2d$^{+/\beta Geo}$ Mice:

KMT2D is a member of the mixed lineage leukemia (MLL) family of *Drosophila* Trithorax orthologs that is encoded on human chromosome 12 and mouse chromosome 15. An alternative name for KMT2D is mixed lineage leukemia 2 (MLL2). All members of this family contain a SET domain, which confers the H3K4 methyltransferase activity, as well as other domains (Hunter et al. (2012) *Nucleic Acids Res.* 40: 306-12) that delineate individual functions (FIG. 6A). A mouse model harboring a loss-of-function allele for Kmt2b, encoded on human chromosome 19 and mouse chromosome 7, has been characterized previously (Kerimoglu et al. (2013) *J. Neurosci.* 33, 3452-64), demonstrating hippocampal memory defects. This gene has been alternatively designated Mll4 or Mll2, leading to confusion in the literature regarding nomenclature for this particular gene family, as discussed in a recent publication by Bogerhausen et al. ((2013) *Clin. Genet.* 83: 212-4). To specifically assess the underlying pathogenesis of KS, a novel mouse model has been characterized with insertion of an expression cassette encoding a β-galactosidase neomycin resistance fusion protein (β-Geo) into intron 50 of Kmt2d (Mll2) on mouse chromosome 15. Inclusion of a splice acceptor sequence and a 3'-end cleavage and polyadenylation signal at the 5' and 3' ends of the β-Geo cassette, respectively, is predicted to generate a truncated KMT2D protein with peptide sequence corresponding to the first 50 exons of Kmt2d fused to β-Geo, but lacking the SET domain and therefore methyltransferase activity (FIG. 6B and FIG. 7A). As predicted from this targeting event, quantitative real-time polymerase chain reaction analysis of Kmt2d messenger RNA in Kmt2d$^{+/\beta Geo}$ mice demonstrates normal abundance of sequence corresponding to exon 20 but a 50% reduction for exon 52, when compared to Kmt2d$^{+/+}$ littermates (FIG. 6C). Expression of a KMT2D-β-galactosidase fusion protein in Kmt2d$^{+/\beta Geo}$ animals demonstrates transcription and translation of the targeted allele (FIG. 7B). Furthermore, chromatin immunoprecipitation followed by next generation sequencing (ChIP-seq) on splenic cells from Kmt2d$^{+/\beta Geo}$ mice and Kmt2d$^{+/+}$ littermates using an antibody against H3K4me3 reveals an overall genome-wide decrease in H3K4me3 in Kmt2d$^{+/\beta Geo}$ mice (FIG. 6D), supporting the predicted functional consequences of the mutant allele. Finally, Kmt2d$^{+/\beta Geo}$ mice demonstrate facial features that are consistent with KS including flattened snout (FIG. 8A) and downward rotation of the ear canal (FIG. 8B). Blinded analysis of X-rays of Kmt2d$^{+/\beta Geo}$ mice revealed a significantly shorter maxilla (P<0.005) when compared to Kmt2d$^{+/+}$ littermates (FIG. 8B and FIG. 8C), as judged by the extent of protrusion beyond the mandible (FIG. 8C).

Kmt2d$^{+/\beta Geo}$ Mice Demonstrate Hippocampal Memory Defects:

Disruption of several histone modifying enzyme genes has been shown to lead to hippocampal memory defects in mice, illustrating a critical role for epigenetic homeostasis in memory acquisition (Guan et al. (2002) *Cell.* 111: 483-93; Gupta et al. (2010) *J. Neurosci.* 30: 3589-99; Cohen-Armon et al. (2004) *Science* 304:1820-2). Kmt2d$^{+/\beta Geo}$ mice show significant deficits in novel object recognition, (FIG. 6E), Morris water maze tests (FIG. 6F) and contextual fear conditioning (FIG. 9) when compared to Kmt2d$^{+/+}$ littermates, all consistent with hippocampal memory dysfunction. When performed before the hidden platform stage of training, the flag-training phase of the Morris water maze did not reveal significant differences between Kmt2d$^{+/\beta Geo}$ and Kmt2d$^{+/+}$ littermates (FIG. 10). Importantly, Kmt2d$^{+/\beta Geo}$ mice did not show decreased activity (FIG. 11A), reduced grip strength (FIG. 11B) or slower swim speeds (FIG. 11C), any of which would be indicative of a more generalized limitation of performance potential in these assays. There were no significant differences in the time that it took Kmt2d$^{+/\beta Geo}$ mice to identify the platform (escape latency) compared to Kmt2d$^{+/+}$ mice during the training phase (FIG. 12A, FIG. 12B, FIG. 12C, and FIG. 12D).

Decreased Dentate Gyrus Volume and Defective Neurogenesis in Kmt2D$^{+/\beta Geo}$ Mice:

Immunofluorescence analyses revealed particularly high levels of expression of KMT2D protein in the dentate gyms GCL of the hippocampus in Kmt2d$^{+/+}$ mice (FIG. 13A) and a striking deficiency of H3K4me3 in the dentate gyms GCL of Kmt2d$^{+/\beta Geo}$ mice compared to wild-type (WT) littermates (FIG. 13B and FIG. 13C). A similar deficiency of H3K4me3 was also seen in the pyramidal layer of the hippocampus (FIG. 14). The levels of H3K4me3 showed substantial cell-to-cell variability in Kmt2d$^{+/\beta Geo}$ animals (FIG. 13B), suggesting that variation in cell state or identity within the GCL or dentate gyms might influence vulnerability to the consequences of heterozygous Kmt2d disruption. Kmt2d$^{+/\beta Geo}$ mice showed a significant decrease in body but not brain weight (FIG. 15A and FIG. 15B), and had reduced dentate gyms GCL volume when standardized to brain weight (FIG. 13D and FIG. 13E). This correlated with reduced neurogenesis in the GCL of Kmt2d$^{+/\beta Geo}$ mice, as evidenced by significantly reduced expression of both doublecortin (DCX; Rao and Shetty (2004) *Eur. J. of Neurosci.* 19: 234-246) (FIG. 13F and FIG. 13G) and 5-ethynyl-2'-deoxyuridine (EdU) staining, a marker of both neurogenesis in the GCL and a marker of neuronal survival when monitored 30 days after labeling (FIG. 16). Confocal microscopy revealed an apparent decrease in dendritic branching complexity of DCX positive cells (DCX+) in the GCL of Kmt2d$^{+/\beta Geo}$ mice (FIG. 17). However, given the decreased amounts of DCX+ cells in these mice, further work is needed to determine if this is a true or primary manifestation of Kmt2d deficiency. To explore whether there are hippocampal memory defects in patients with KS, comprehensive neuropsychological testing performed on three patients with known disease causing mutations in KMT2D was analyzed (Table 2; N/A=not adequately tested with utilized testing regimen; ↓=deficient area (defined as >1 standard deviation below the mean and lower than full scale IQ or, if unavailable, highest individual test score; metrics linked to the dentate gyms are indicated in yellow (Kesner (2013) *Behav. Brain Res.* 254:1-7; Morris et al. (2012) *Neurobiol. Learn. Mem.* 97:326-31; Epp et al., (2011) *Neurobiol. Learn. Mem.* 95:316-25); metrics more broadly linked to the hippocampus are indicated with an asterisk (Brickman et al. (2011) *Hippocampus.* 21:923-8)). Although, not all deficiencies observed can be explained by hippocampal dysfunction, patients consistently had abnormalities of tasks known to be associated with dentate gyms function (Kesner (2013) *Behav. Brain Res.* 254:1-7; Morris et al. (2012) *Neurobiol. Learn. Mem.* 97:326-31; Epp et al., (2011) *Neurobiol. Learn. Mem.* 95:316-25). Other functions linked to other regions of the hippocampus (Brickman et al. (2011) *Hippocampus.* 21:923-8) were also abnormal in some patients as were some tasks not linked to hippocampus indicating that other cell populations in the central nervous system may also play a role. These data support the hypothesis that observations in Kmt2d$^{+/\beta Geo}$ mice are, at least in part, reminiscent of those seen in KS.

TABLE 2

A retrospective analysis of neuropsychological testing on three patients with mutations in KMT2D reveals consistent abnormalities of functions that have been patients with known associated with the dentate gyms. Neuropsychological testing of disease causing mutations in KMT2D.

| Neuropsychologic process/function | Patient 1 28 yrs Female | Patient 2 15 yrs Female | Patient 3 14 yrs Male |
|---|---|---|---|
| Affected Gene | KMT2D | KMT2D | KMT2D |
| Full Scale IQ | 87 | 84 | 66 |
| Perceptual or Non-verbal Reasoning* | ↓ | ↓ | ↓ |
| Verbal Reasoning/Comprehension | Normal | Normal | ↓ |
| Verbal Fluency* | ↓ | Normal | N/A |
| Naming* | Normal | Normal | Normal |
| Vocabulary/Reading | Normal | Normal | N/A |
| Processing Speed | ↓ | ↓ | ↓ |
| Basic Math Calculation | Normal | ↓ | N/A |
| Visual Selective Attention* | ↓ | ↓ | N/A |
| Visual Working Memo | ↓ | ↓ | ↓ |
| Verbal Working Memory* | Normal | Normal | ↓ |
| Visual Delayed Memory* | ↓ | ↓ | ↓ |
| Verbal Delayed Memory* | ↓ | ↓ | Normal |
| Switching/Inhibition | ↓ | ↓ | N/A |
| Verbal Organization | Normal | Normal | N/A |
| Visual Organization* | ↓ | ↓ | ↓ |
| Fine Motor | ↓ | ↓ | ↓ |

Application of Reporter Alleles for Epigenetic Modifications in Embryonic Fibroblasts from Kmt2d$^{+/\beta Geo}$ Mice:

Epigenetic reporter systems were created that monitor either H4 acetylation or H3K4 trimethylation machinery activity in an effort to determine whether there is an ongoing activity deficiency in cells from Kmt2d$^{+/\beta Geo}$ mice (FIG. 18A). Both reporter alleles encode halves of green fluorescent protein separated by a flexible linker region (Baird et al. (1999) *Proc. Natl. Acad. Sci.* 96: 11241-6) with a histone tail and a histone reader at the N- and C-termini, respectively. When the histone tail corresponding to either H4 or H3 is modified by acetylation or methylation, respectively, GFP structure and function are reconstituted, as detected by a fluorescent readout (FIG. 18B). The acetyl reporter protein quantifies the activity of the acetylation machinery (acetylation of H4 specifically at sites K5, K8, K12, and K16) and comprises an H4 tail (residues 1-30) on one end and a TATA binding protein (TBP)-associated factor II (TAFII) bromodomain on the other end (FIG. 18A). The TAFII bromodomain only recognizes and binds to the acetylated H4 tail. This acetylation-dependent reporter protein demonstrates a linear fluorescence response when quantified by fluorescence-activated cell sorting (FACS) in the presence of increasing amounts of suberoylanilide hydroxamic acid (SAHA), an HDACi, in culture systems (FIG. 18C, FIG. 18D, FIG. 19A, and FIG. 19B). For example, only 5% of cells were easily discriminated from auto fluorescence with 1 µM of SAHA, but increased to 20% with 2.5 µM of SAHA, 40% at 7.5 µM of SAHA and 45% at 10 µM of SAHA (FIG. 18D). Saturation of this response correlates well with immunoblot data using antibodies to the modified H4 tail (Munshi et al. (2006) *Mol. Cancer Ther.* 5:1967-74). This response is attenuated by co-transfection with a construct encoding a histone deacetylase (FIG. 20) and absent upon mutagenesis of all potential acetylation sites (FIG. 18E and FIG. 18I), attesting to its specificity. The H3K4 trimethylation reporter allele encodes the H3 tail (residues 1-40) on one end and the TBP-associated factor III (TAF3) plant homeodomain (PHD) on the other end, which binds to trimethylated K4 on H3 (FIG. 18A). The H3K4 trimethylation reporter also demonstrates a dose response with increasing levels of the HDACi AR-42 (FIG. 18F), in keeping with prior work suggesting that AR-42 can also influence the methylation status of H3K4 through inhibition of demethylases (Huang et al. (2011) *Mol. Pharmacol.* 79:197-206). Activity is greatly attenuated upon mutagenesis of critical residues (M882A, W891A; Vermeulen et al. (2007) *Cell* 131, 58-69; van Ingen et al (2008) *Structure* 16, 1245-56) in the TAF3 reader domain (FIG. 18G) or with mutation of K4 (H3K4Q) in the H3 tail (FIG. 18G). Both reporter alleles show decreased activity when stably introduced into embryonic fibroblasts derived from Kmt2d$^{+/\beta Geo}$ mice, when compared to Kmt2d$^{+/+}$ littermates (FIG. 21). H3K4 trimethylation activity is enhanced upon treatment of Kmt2d$^{+/\beta Geo}$ cells with HDAC inhibitors AR-42 or MS275 (FIG. 18H, FIG. 22A, and FIG. 23). An analysis of transfection efficacy in cells with both genotypes indicated comparable transfection efficacy (FIG. 22B).

Impaired Neurogenesis and H3K4 Trimethylation Deficiency in Kmt2d$^{+/\beta Geo}$ Mice is Rescued Upon Treatment with the HDACi AR-42:

Because of the ability of HDACi to increase H3K4 trimethylation in vitro in Kmt2d$^{+/\beta Geo}$ cells, it was next asked whether the H3K4 trimethylation deficiency seen in the dentate gyms GCL of Kmt2d$^{+/\beta Geo}$ mice could be attenuated or reversed upon in vivo postnatal treatment with an HDACi. Previously, the HDACi's AR-42 and MS275 have both been shown to increase H3K4 trimethylation and histone acetylation (Huang et al. (2011) *Mol. Pharmacol.* 79:197-206). AR-42 appeared to have the strongest effect on H3K4me3 and was therefore chosen for in vivo studies (Huang et al. (2011) *Mol. Pharmacol.* 79:197-206). An AR-42 dose of 25 mg/kg/day was started, previously used in mouse models of prostate cancer (Huang et al. (2011) *Mol. Pharmacol.* 79:197-206), commencing at 20 weeks of age and continuing for two weeks. This dose increased H3K4 trimethylation in the GCL in Kmt2d$^{+/\beta Geo}$ mice, compared to untreated mutant littermates (FIG. 24A and FIG. 24B), to a level that was indistinguishable from treated Kmt2d$^{+/+}$ animals. Unexpectedly, however, this dose of AR-42 was associated with decreased DCX expression in the GCL in both young (1-2 month-old) and old (5-6 month-old) Kmt2d$^{+/+}$ and Kmt2d$^{+/\beta Geo}$ mice (FIG. 24C and FIG. 24D). Given the known cytotoxic potential of AR-42 (Huang et al. (2011) *Mol. Pharmacol.* 79:197-206; Zhang et al. (2011) *Int. J. Cancer.* 129:204-13), 5 and 10 mg/kg/day doses were next tested, and a dose-dependent increase in H3K4me3 and preservation or restoration of DCX expression in Kmt2d$^{+/+}$ or Kmt2d$^{+/\beta Geo}$ animals in both age groups, respectively, were observed (FIG. 25A, FIG. 25B, FIG. 25C, FIG. 25D and FIG. 24D). This dose also led to a genome-wide increase in H3K4me3 in spleen cells from Kmt2d$^{+/\beta Geo}$ mice, when compared to Kmt2d$^{+/+}$ littermates on vehicle (FIG. 25E) in association with normalization of expression of Klf10 (FIG. 26), a known Kmt2d target gene (Guo et al. (2012) *Proc. Natl. Acad. Sci. U.S.A.* 109:17603-8). In fact, this dose appeared to overcorrect the deficiency (FIG. 25E) which can be observed when representing data as MA plots (FIG. 27A, FIG. 27B, FIG. 27C, FIG. 27D, and FIG. 27E) or visualizing the shifts in balance among the two states (FIG. 28A, FIG. 28B, FIG. 28C, FIG. 28D and FIG. 28E). Other state combinations with the same representations were also compared, showing a relative normalization of genome-wide H3K4me3 in Kmt2d$^{+/\beta Geo}$ mice treated with AR-42, when compared to Kmt2d$^{+/+}$ littermates that did (FIG. 27E) or did not (FIG. 27B) receive drug. The bigger effect at lower intensity Log 2 (CPM) fits with data from ablation of Rubinstein-Taybi gene (CBP) which has dose dose-dependent effects on gene expression thought to depend on the strength of recruitment for a particular site (Kasper et al. (2010) *EMBO J.* 29:3660-72).

Improvement of Hippocampal Memory Defects in Kmt2d$^{+/\beta Geo}$ Mice Treated with AR-42:

In keeping with the hypothesis that abnormal GCL neurogenesis contributes to functional deficits, it was found that performance in hippocampal memory testing correlated with AR-42 dose-dependent effects on DCX expression. Specifically, both Kmt2d$^{+/+}$ and Kmt2d$^{+/\beta Geo}$ mice showed improved performance on Morris water maze platform crossing during probe trial (Garthe and Kempermann (2013) *Front Neurosci.* 7:63) in response to 10 mg/kg/day of AR-42, with a greater response in Kint2d$^{+/\beta Geo}$ animals and no significant difference between genotypes in the treatment group (FIG. 25F).

Discussion

Prior studies have associated structural abnormalities of the dentate gyms with impaired neurogenesis and hippocampal memory defects (Ansorg et al. (2012) *BMC Neurosci.* 13: 46; Denis-Donini et al. (2008) *J. Neurosci.* 28:3911-3919). In accordance with the previously observed phenotype in Mll4-targeted mice ((Kerimoglu et al. (2013) *J. Neurosci.* 33, 3452-64), it has been found that heterozygosity for a loss-of-function Kmt2d allele associates a deficiency of H3K4me3 in the dentate gyrus GCL with hippocampal memory defects in a mouse model of KS. Support for a causal relationship is now greatly enhanced by the observation disclosed herein that memory deficits can be prevented or even reversed through systemic delivery of drugs that directly influence the histone modification events that favor chromatin opening.

The data support the hypothesis that the neurodevelopmental deficiency in KS is maintained by an impairment of adult neurogenesis due to an imbalance between open and closed chromatin states for critical target genes. In this light, other Mendelian disorders involving the histone modification machinery (now numbering over 40; Berdasco and Esteller (2013) *Hum. Genet.* 132: 359-83) might be amenable to therapeutic intervention with HDAC inhibition (Dash et al. (2009) *Neuroscience* 163:1-8; Vecsey et al. (2007) *J. Neurosci.* 27: 6128-6140; Graff and Tsai (2013) *Annu. Rev. Pharmacol. Toxicol.* 53:311-30). In keeping with this concept, neurological phenotypes in mouse models of Rubinstein-Taybi syndrome with haploinsufficiency for the gene encoding the histone acetyl transferase CREB binding protein (Cbp) respond to intracerebroventricular or intraperitoneal administration of the histone deacetylase inhibitors SAHA or trichostatin A, respectively (Korzus et al. (2004) *Neuron.* 42, 961-72; Alarcón et al. *Neuron.* 42, 947-59 (2004), however no cellular mechanism was described. The specific correlation between H3K4me3 and neurogenesis within the dentate gyms of KS mice offers a potential unifying mechanism for hippocampal memory defects seen in inherited defects of the histone modification machinery (Gupta et al. (2010) *J. Neurosci.* 30:3589-99; Cohen-Armon et al. (2004) *Science* 304:1820-2; Korzus et al. (2004) *Neuron.* 42:961-72; Alarcón et al. (2004) *Neuron.* 42:947-59). The further positive correlation of these events with functional outcome supports the hypothesis that the fate of the GCL in the dentate gyrus is a critical determinant of both disease pathogenesis and treatment. More work is needed to determine the relative contribution of precursor cell recruitment, differentiation, proliferation and/or survival (Yang et al. (2012) *Mol. Cell. Biol.* 32:3121-31; Lubitz et al. (2007) *Mol. Biol. Cell.* 18:2356-66). Future studies using lineage-specific Kmt2d targeting will help elucidate the contribution of individual cell populations (GCL, pyramidal layer, molecular layer of the cerebellum) to specific neurodevelopmental phenotypes.

Although there is an overall decrease in H3K4me3 in the dentate gyms GCL of Kmt2d$^{+/\beta Geo}$ mice, substantial cell-to-cell variation is noted. This might reflect redundancy of enzymes capable of adding the H3K4 trimethylation mark (Hunter et al. (2012) *Nucleic Acids Res.* 40: 306-12) that could vary in their expression level (and therefore compensation capacity) in a cell type- (e.g. differentiation state) or cell state- (e.g. electrochemical environment) dependent manner. Alternatively, this could indicate that stochastic events thought to contribute to epigenetic individuality (Bjornsson et al. (2004) *Trends Genet.* 20: 350-8) play a role.

There is precedent that HDACi not only increases histone acetylation, but also H3K4 trimethylation (Huang et al. (2011) *Mol. Pharmacol.* 79:197-206). The presently disclosed indicators nicely illustrate coupling between H4 acetylation and H3K4 trimethylation, with Kmt2d$^{+/\beta Geo}$ mice having defects in both systems. The novel reporter alleles described here have the potential for application in small molecule screens to identify drugs with greater potency, specificity and tolerance. There are also many FDA-approved medications, some with longstanding clinical use, that influence epigenetic modifications in addition to their originally established functions. An example is the anti-epileptic agent valproic acid, which was recently shown to be a potent HDACi (Phiel et al. (2001) *J. Biol. Chem.* 276:36734-41). Several widely-used supplements or dietary substances, such as folic acid, genestein, and curcumin, are known to influence epigenetic modifications (Meeran et al. (2010) *Clin. Epigenetics.* 1:101-116). These observations may inform the question of potential toxicity of interventions that have broad effects on pervasive epigenetic events. The apparent tolerance to chronic use of such agents during postnatal life likely reflects, at least in part, the complex context within which gene transcription and ultimate function is achieved. Contributing factors include DNA modifications, a repertoire of both positive and negative effectors of transcription, and feedback mechanisms that titrate both gene expression and protein function. In this light, the predominant influence of agents such as HDACi as therapies may prove permissive for correction of pathologic alterations in physiologic gene expression and function rather than obligate and therefore less conducive to homeostasis.

Although a beneficial effect of AR-42 treatment on neurogenesis at two different ages (1-2 months and 5-6 months) was demonstrated, suggesting that this sub-phenotype of KS may be treatable even in adulthood, it is well established that neurogenesis potential is age-restricted (Martinez-Canabal et al. (2013) *Hippocampus* 23:66-74). It will be essential to further refine the window of opportunity to influence neurogenesis in the GCL in both mouse models and patients. It is also possible, but as yet unproven, that brief treatment in early postnatal stages will result in the expansion of a stable population of cells within the GCL (despite an ongoing relative deficiency of methyltransferase function) and hence achieve long-term recovery of neurologic function. Finally, the ChIP-seq experiments suggest that AR-42 at a dose of 10 mg/kg/day led to the most improvement in functional studies (FIG. 25D), but overcorrection of genome-wide H3K4me3 (FIG. 25E). Given the favorable tolerance profile of high-dose HDACi when used for cancer treatment, this may not be a limiting factor. However, new challenges may arise when HDACi are used chronically for KS or other neurodevelopmental disorders. The combination of in vivo ChIP-seq analyses and in vitro reporter allele performance with regard to H3K4me3 status may ultimately allow optimization in the selection of agent and dose for therapeutic purposes. This concept will be explored in future work.

The data (FIG. 6D, FIG. 25E, FIG. 27A, FIG. 27B, FIG. 27C, FIG. 27D, FIG. 27E, FIG. 28A, FIG. 28B, FIG. 28C, FIG. 28D, and FIG. 28E) demonstrate that ChIP (Chromatin Immunoprecipitation) based techniques have the potential of being a marker of the disease states (FIG. 6D, FIG. 27A) and thereby have diagnostic potential but could also act as biomarkers of therapeutic efficiency (FIG. 25E, FIG. 27B).

In conclusion, this work suggests that a postnatally ongoing and reversible deficiency of GCL H3K4me3 in association with adult neurogenesis underlies intellectual disability in a mouse model of KS. This work adds to the emerging view that multiple genetic etiologies of intellectual disability may be amenable to postnatal therapies (Guy et al. (2007) *Science* 315:1143-7; Das et al. (2013) *Sci. Transl. Med.* 5: 201ra120; Henderson et al. (2012) *Sci. Transl. Med.* 4:152ra128).

Example 2

Although Example 1 describes reporter alleles for two histone modifications (i.e. H3K4me3 and histone acetylation), the presently disclosed constructs may be applied to many additional histone modifications (see, e.g., FIG. 2 and FIG. 30). In FIG. 30, several additional histone modifications within the scope of the presently disclosed subject matter are shown, such as H3K9me3, H3K27me3, H3K36me3 and H3K20me3. Specifically, FIG. 30 shows additional histone modifications relating to H3 and H4 tails and types of acetylation and methylation. However, there are many additional histone modifications within the scope of the presently disclosed subject matter, including but not limited to phosphorylation, ubiquitylation, sumoylation, butyrylation, proprionylation, glycylation, citrullination, and ADP-ribosylation (see Table 3 below).

Table 3 shows various histone modifications and some of the readers that recognize these modifications (Gardner et al. (2011) *J. Mol Biol.* 409:36-46). In particular, Table 3 shows the typical amino acids (K, R, S, T) affected by modifications (column 2) and lists some of the known domains known to read particular marks (column 3). The reporter system of the presently disclosed subject matter could easily be expanded to work for any histone modification for which a specific reader domain is known. For example, although Example 1 described the use of the TAFII bromodomain and TAFIII homeodomain, there are many more specific reader domains that have been described (Gardner et al. (2011) *J. Mol Biol.* 409:36-46). Accordingly, with respect to the constructs described in Example 1, the histone domains and readers may be replaced with a tail and reader domain of a corresponding system. As additional specific reader domains are discovered for particular histone modifications, one of skill in the art would readily be able to incorporate such reader domains into the presently disclosed subject matter to cover additional histone modification systems.

TABLE 3

Typical amino acids affected by histone tail modifications and selected domains known to read particular marks (based on data from Gardner et al. (2011) *J. Mol Biol.* 409: 36-46).
Histone tail modifications

| | | |
|---|---|---|
| Acetylation | K | Bromodomain |
| Methylation | K, R | Chromodomain and others |
| Phosphorylation | S, T | 14-3-3, BIR, BRCT |
| Ubiquitylation | K | ? |
| Sumoylation | K | ? |
| Butyrylation | K | ? |
| Propionylation | K | ? |
| Glycylation | S, T | ? |
| Citrullination | R | ? |
| ADP-ribosylation | K | ? |

From Gardner K E, Allis C D, Strahl B D. J. Mol. Bio. 2011

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A fusion protein reporter comprising:
   a) a histone-modification-specific binding domain that is configured to bind to said histone polypeptide substrate when said histone polypeptide substrate is modified;
   b) a histone polypeptide substrate; and
   c) a flexible linker region, wherein the flexible linker region is flanked on one side by a region encoding a C-terminal portion of a circularly permutated fluorescent protein and on the other side by a region encoding the N-terminal portion of the circularly permutated fluorescent protein, and wherein said C-terminal portion of said circularly permutated fluorescent protein and said N-terminal portion of said circularly permutated fluorescent protein form a functional fluorescent protein when said histone-modification-specific binding domain binds to said histone polypeptide substrate.

2. The fusion protein reporter of claim 1, wherein the histone polypeptide is selected from the group consisting of H3 and H4.

3. The fusion protein reporter of claim 1, wherein the histone polypeptide is selected from the group consisting of the N-terminus of H3 and the N-terminus of H4, wherein said N-terminus retains the ability to bind with said histone-modification specific binding domain.

4. The fusion protein reporter of claim 1, wherein the histone modification is selected from the group consisting of acetylation, methylation, and phosphorylation.

5. The fusion protein reporter of claim 1, wherein the histone modification-specific binding domain is selected from the group consisting of a TBP associated factor II (TAFII) bromodomain and a TBP associated factor III (TAFIII) homeodomain.

6. The fusion protein reporter of claim 1, wherein the histone polypeptide is a polypeptide substrate for the histone-modification-specific binding domain.

7. The fusion protein reporter of claim 1, further comprising a targeting polypeptide associated with the fusion protein.

8. The fusion protein reporter of claim 7, wherein the targeting polypeptide comprises at least one nuclear localization sequence (NLS).

9. The fusion protein reporter of claim 8, wherein the targeting polypeptide comprises a repeated NLS.

10. The fusion protein reporter of claim 1, wherein the circularly permutated fluorescent protein comprises a circularly permutated green fluorescent protein (GFP).

11. An expression vector comprising an expression cassette encoding a fusion protein reporter of claim 1.

12. A host cell transformed or transfected with the expression vector of claim 11.

13. A non-human transgenic animal, wherein the genome of the transgenic animal comprises an expression cassette encoding a fusion protein reporter of claim 1.

14. A method for producing a cell specific screening assay for test agents, comprising:
 a) providing a transgenic animal of claim 13;
 b) crossing the transgenic animal with a compatible animal, wherein the compatible animal is an animal model of a disease, thereby producing a hybrid;
 c) isolating a disease relevant cell type that comprises the fusion protein reporter of claim 1 from the hybrid; and
 d) utilizing the isolated disease relevant cell types in a high throughput screening assay for test agents that inhibit a histone modification activity in said disease relevant cell types.

15. A method of determining the level of histone modification activity in a biological sample comprising:
 a) contacting a biological sample with a fusion protein reporter of claim 1; and
 b) monitoring the level of in the biological sample as a measure of the level of histone modification activity in the biological sample.

16. The method of claim 15, wherein the biological sample is selected from the group consisting of cells and tissues.

17. A method of monitoring the onset, progression, or regression of a histone-modification disorder in a subject comprising:
 a) contacting a first biological sample obtained from a subject with a fusion protein reporter of claim 1;
 b) determining the level of fluorescence in the first biological sample;
 c) contacting a subsequent second biological sample obtained from the subject with the fusion protein reporter;
 d) determining the amount of fluorescence in the second biological sample; and
 e) comparing the level of fluorescence in the first biological sample to the level of fluorescence in the second biological sample as a measure of the onset, regression or progression of a histone modification disorder in the subject.

18. The method of claim 17, further comprising administering after the first biological sample is obtained from the subject and before the second biological sample is obtained from the subject, a candidate pharmacological agent to the subject, wherein the measure of the onset, progression, or regression of a histone modification disorder in the subject is an indication of the effect of the candidate pharmacological agent on histone modification in the subject.

19. The method of claim 17, wherein the biological sample is selected from the group consisting of cells and tissues.

20. A method for evaluating the effect of candidate pharmacological agents on histone modification activity in a biological sample comprising:
 a) contacting a biological sample with a fusion protein reporter fusion protein reporter of claim 1;
 b) determining a first level of fluorescence in the biological sample;
 c) contacting the biological sample with a candidate pharmacological agent;
 d) determining a second level of fluorescence in the biological sample; and
 e) comparing the first level of fluorescence in the cell with the second level of fluorescence in the cell, wherein a relative increase or relative decrease in fluorescence indicates an effect of the candidate pharmacological agent on histone modification activity in the biological sample.

21. The method of claim 20, wherein the biological sample is selected from the group consisting of cells and tissues.

22. The method of claim 20, wherein the biological sample is a cell.

23. The method of claim 22, wherein the cell is undergoing cell division.

24. The method of claim 22, wherein the cell is a living cell.

25. A kit for diagnosing and/or monitoring treatment efficacy of a histone modification disorder, comprising:
 a) a container containing a fusion protein reporter fusion protein reporter of claim 1; and
 b) instructions for the use of the fusion protein reporter in the diagnosis and/or monitoring treatment efficacy of a histone-modification disorder.

26. The kit of claim 25, wherein the kit comprises reagents and/or instructions for chromatin immunoprecipitation (ChiP).

27. The kit of claim 26, wherein the kit comprises reagents and/or instructions for chromatin immunoprecipitation-sequencing (ChiP-seq).

* * * * *